US012612378B2

(12) United States Patent
Kim et al.

(10) Patent No.: US 12,612,378 B2
(45) Date of Patent: Apr. 28, 2026

(54) COMPOUND, PHOTOELECTRIC DEVICE, LIGHT ABSORPTION SENSOR, SENSOR-EMBEDDED DISPLAY PANEL, AND ELECTRONIC DEVICE

(71) Applicant: Samsung Electronics Co., Ltd., Suwon-si (KR)

(72) Inventors: Hyeongju Kim, Changwon-si (KR); Feifei Fang, Suwon-si (KR); Kyung Bae Park, Hwaseong-si (KR); Jeong Il Park, Seongnam-si (KR); Jisoo Shin, Suwon-si (KR); Sung Young Yun, Suwon-si (KR); Taejin Choi, Suwon-si (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 884 days.

(21) Appl. No.: 17/876,973

(22) Filed: Jul. 29, 2022

(65) Prior Publication Data

US 2023/0113862 A1 Apr. 13, 2023

(30) Foreign Application Priority Data

Jul. 30, 2021 (KR) ........................ 10-2021-0100798

(51) Int. Cl.

| | |
|---|---|
| ***H01L 51/54*** | (2006.01) |
| ***C07D 343/00*** | (2006.01) |
| ***C07D 345/00*** | (2006.01) |
| ***C07D 471/06*** | (2006.01) |
| ***C07D 495/04*** | (2006.01) |
| ***C07D 497/06*** | (2006.01) |
| ***C07D 517/04*** | (2006.01) |
| ***C07F 7/08*** | (2006.01) |
| ***H10K 30/50*** | (2023.01) |
| ***H10K 85/40*** | (2023.01) |
| ***H10K 85/60*** | (2023.01) |
| *H10K 39/32* | (2023.01) |
| *H10K 65/00* | (2023.01) |

(52) U.S. Cl.

CPC ......... *C07D 343/00* (2013.01); *C07D 345/00* (2013.01); *C07D 471/06* (2013.01); *C07D 495/04* (2013.01); *C07D 497/06* (2013.01); *C07D 517/04* (2013.01); *C07F 7/0816* (2013.01); *H10K 30/50* (2023.02); *H10K 85/40* (2023.02); *H10K 85/615* (2023.02); *H10K 85/621* (2023.02); *H10K 85/654* (2023.02); *H10K 85/657* (2023.02); *H10K 85/6576* (2023.02); *H10K 39/32* (2023.02); *H10K 65/00* (2023.02); *H10K 85/649* (2023.02)

(58) Field of Classification Search

None

See application file for complete search history.

(56) References Cited

U.S. PATENT DOCUMENTS

| | | | | |
|---|---|---|---|---|
| 9,252,371 | B1 | 2/2016 | Yagi et al. | |
| 9,490,442 | B2 | 11/2016 | Leem et al. | |
| 9,548,463 | B2 | 1/2017 | Yagi et al. | |
| 9,608,212 | B2 | 3/2017 | Ishibe et al. | |
| 11,145,822 | B2 | 10/2021 | Shin et al. | |
| 2019/0092743 | A1 * | 3/2019 | Nishide .................. | H10K 30/82 |
| 2021/0024544 | A1 * | 1/2021 | Shin ..................... | C07D 495/04 |

FOREIGN PATENT DOCUMENTS

| | | | |
|---|---|---|---|
| CN | 109912621 | A | 6/2019 |
| CN | 111393452 | A | 7/2020 |
| EP | 3770163 | A1 | 1/2021 |
| EP | 3848374 | A1 | 7/2021 |
| JP | 2018-002690 | A | 1/2018 |
| KR | 10-2015-0115477 | A | 10/2015 |
| KR | 10-2016-0011038 | A | 1/2016 |
| KR | 10-2016-0018029 | A | 2/2016 |
| KR | 10-2019-0044555 | A | 4/2019 |
| WO | WO-2017/208965 | A1 | 12/2017 |
| WO | WO-2019/052935 | A1 | 3/2019 |

OTHER PUBLICATIONS

Extended European Search Report dated Nov. 14, 2022 for corresponding European Application No. 22187944.8.

C. Dalinot et al. "Spirobifluorene based small push-pull molecules for organic photovoltaic applications", Dyes and Pigments (2017), 140, 62-69.

A. Nowak-Krol et al. "Modulation of band gap and p-versus n-semiconductor character of ADA dyes by core and acceptor group variation", Organic Chemistry Frontiers (2016), 3(5), 545-555.

* cited by examiner

*Primary Examiner* — Andrew K Bohaty

(74) *Attorney, Agent, or Firm* — Harness, Dickey & Pierce, P.L.C.

(57) ABSTRACT

A compound is represented by Chemical Formula 1.

[Chemical Formula 1]

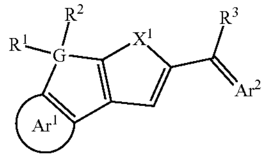

In Chemical Formula 1, G, $R^1$, $R^2$, $R^3$, $X^1$, $Ar^1$ and $Ar^2$ are each the same as in the specification.

23 Claims, 14 Drawing Sheets

COMPOUND, PHOTOELECTRIC DEVICE, LIGHT ABSORPTION SENSOR, SENSOR-EMBEDDED DISPLAY PANEL, AND ELECTRONIC DEVICE

CROSS-REFERENCE TO RELATED APPLICATION

This application claims priority to and the benefit of, under 35 U.S.C. § 119, Korean Patent Application No. 10-2021-0100798 filed in the Korean Intellectual Property Office on Jul. 30, 2021, the entire contents of which are incorporated herein by reference.

BACKGROUND

1. Field

Example embodiments relate to compounds, photoelectric devices, light absorption sensors, sensor-embedded display panels, and electronic devices.

2. Description of the Related Art

Recently, there is an increasing demand for a display device implementing a biometric recognition technology that authenticates the person by extracting specific biometric information or behavioral characteristic information of a person with an automated device, centering on finance, healthcare, and mobile device. Accordingly, research is being conducted on a display device including a sensor capable of biometric recognition.

SUMMARY

Such a sensor capable of biometric recognition, which may be disposed under a display panel of a display device or may be separately manufactured as a separate module and mounted outside the display device. When the sensor is disposed under the display panel, the sensor is configured to recognize an object recognized through the display panel, various films, and/or parts with improved performance and having improved integration overcoming limitations in terms of design and usability that may be associated with sensors manufactured and mounted as separate modules. Accordingly, a sensor-embedded display panel including a sensor capable of improving performance by being integrated with the display panel has been proposed.

The photoelectric device used in the sensor as described above is a device that converts light into an electrical signal using the photoelectric effect, and may include a photodiode and a phototransistor.

A sensor (e.g., an image sensor) including a photodiode has a higher resolution and a smaller pixel size. At present, a silicon photodiode is widely used, but it has a problem of deteriorated sensitivity since silicon photodiode has a smaller absorption area due to small pixels. Accordingly, an organic material that is capable of replacing silicon has been researched.

The organic material has a high extinction coefficient and selectively absorbs light in a particular wavelength region depending on a molecular structure, and thus may simultaneously replace a photodiode and a color filter and resultantly improve sensitivity and contribute to high integration.

Therefore, there is a growing interest in organic materials that can be used in these sensors.

Example embodiments provide a compound capable of selectively absorbing light in a green wavelength region and having excellent thermal stability.

Example embodiments also provide a photoelectric device capable of selectively absorbing light in a green wavelength region and maintaining excellent efficiency even in a process under a high temperature condition.

Example embodiments also provide a light absorption sensor including the photoelectric device.

Example embodiments also provide a sensor-embedded display panel including the photoelectric device or sensor.

Example embodiments also provide an electronic device including the photoelectric device or sensor.

According to some example embodiments, a compound may be represented by Chemical Formula 1.

[Chemical Formula 1]

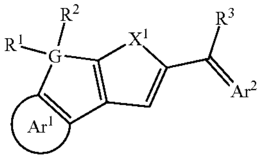

In Chemical Formula 1,

G may be C, Si, or Ge, $R^1$ and $R^2$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, or a cyano group (—CN), wherein $R^1$ and $R^2$ may each independently be present or are linked to each other to provide a spiro structure, $X^1$ may be O, S, Se, Te, S(═O), $S(=O)_2$, $SiR^aR^b$, $GeR^cR^d$, or $CR^eR^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide a separate spiro structure, $R^3$ may be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, pentafluorosulfanyl group ($-SF_5$), a hydroxyl group, a hydrazine group, a hydrazone group, a carboxyl group or a salt thereof, a sulfonic acid group or a salt thereof, a phosphoric acid group or a salt thereof, $-SiR^aR^bR^c$(wherein $R^a$, $R^b$, and $R^c$ may each independently be hydrogen or a substituted or unsubstituted C1 to C10 alkyl group), or any combination thereof, $Ar^1$ may be a substituted or unsubstituted C6 to C30 arene group, a substituted or unsubstituted C3 to C30 heteroarene group, or a condensed ring thereof, and $Ar^2$ may be a substituted or unsubstituted C6 to C30 hydrocarbon cyclic group including at least one functional group of C═O, C═S, C═Se, C═Te, or $C=CR^aR^b$, wherein $R^a$ and $R^b$ may each independently be hydrogen, a substituted or unsubstituted C1 to C10 alkyl group, a cyano group or a cyano-containing group; a substituted or unsubstituted C2 to C30 heterocyclic group including at least one functional group of C=O, C=S, C=Se, C=Te, or C=CR$^a$R$^b$, (wherein R$^a$ and R$^b$ may each independently be hydrogen, a substituted or unsubstituted C1 to C10 alkyl group, a cyano group, or a cyano-containing group); or a fused ring thereof.

In Chemical Formula 1, X$^1$ may be O, S, Se, or Te.

In Chemical Formula 1, Ar$^1$ may be one of moieties represented by Chemical Formula 2.

[Chemical Formula 2]

(1)

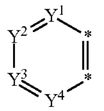

(2)

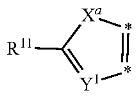

(3)

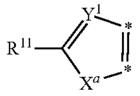

(4)

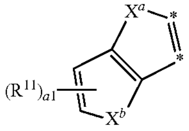

(5)

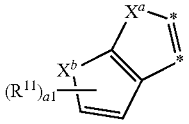

(6)

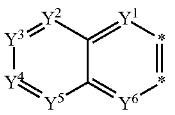

(7)

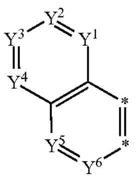

(8)

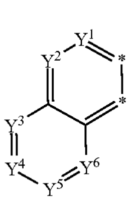

-continued (9)

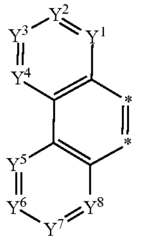

(10)

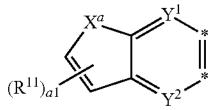

(11)

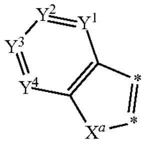

(12)

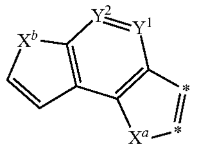

(13)

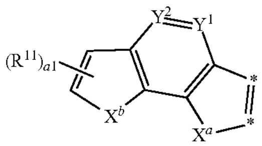

(14)

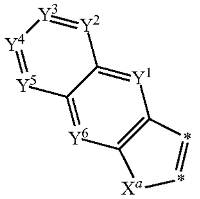

(15)

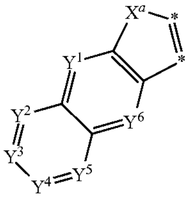

(16)

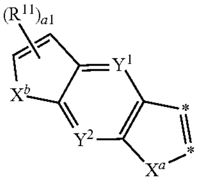

(17)

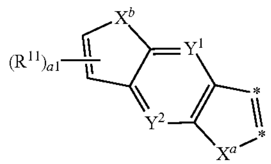

-continued (18)

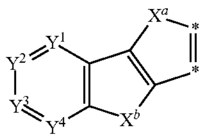

(19)

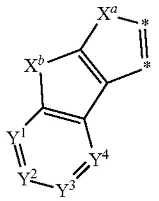

In Chemical Formula 2, $Y^1$ to $Y^8$ may each independently be N or $CR^p$, wherein $R^p$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to provide (e.g., establish, define, etc.) a substituted or unsubstituted C6 to C30 arene group, a substituted or unsubstituted C3 to C30 heteroarene group, or a condensed ring thereof, $X^a$ and $X^b$ may each independently be O, S, Se, Te, S(═O), $S(═O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ may each independently be hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ may each independently be present or at least one pair of $R^b$ and $R^c$, $R^d$ and $R^e$, or $R^f$ and $R^g$ may be linked to each other to provide a spiro structure, $R^{11}$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 may be an integer of 0 to 2, and

* may indicate a linking point that is linked to a pentagonal ring of Chemical Formula 1.

In Chemical Formula 1, $Ar^1$ may be one of moieties represented by Chemical Formula 2A.

[Chemical Formula 2A (1)

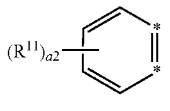

(2)

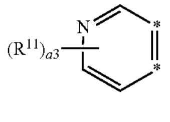

(3)

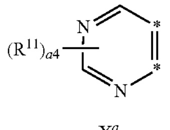

(4)

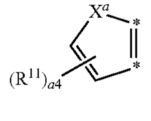

-continued (5)

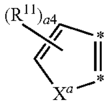

In Chemical Formula 2A, $X^a$ may be O, S, Se, Te, S(═O), $S(═O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ may each independently be hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ may each independently be present or at least one pair of $R^b$ and $R^c$, $R^d$ and $R^e$ and $R^f$ and $R^g$ may be linked to each other to provide a spiro structure, $R^{11}$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a2 may be an integer from 0 to 4, a3 may be an integer from 0 to 3, a4 may be an integer from 0 to 2, and

* indicates a linking point that is linked to a pentagonal ring of Chemical Formula 1.

In Chemical Formula 1, $Ar^1$ may be a substituted or unsubstituted benzene ring, a substituted or unsubstituted naphthalene ring, a substituted or unsubstituted anthracene ring, a substituted or unsubstituted indene ring, a substituted or unsubstituted phenanthrene ring, a substituted or unsubstituted fluorene ring, or a substituted or unsubstituted acenaphthylene ring.

In Chemical Formula 1, $Ar^1$ may be a substituted or unsubstituted thiophene ring, a substituted or unsubstituted selenophene ring, a substituted or unsubstituted tellurophene ring, a substituted or unsubstituted pyridine ring, a substituted or unsubstituted pyrimidine ring, a substituted or unsubstituted pyrazine ring, a substituted or unsubstituted indole ring, a substituted or unsubstituted quinoline ring, a substituted or unsubstituted isoquinoline ring, a substituted or unsubstituted quinoxaline ring, a substituted or unsubstituted quinazoline ring, a substituted or unsubstituted carbazole ring, a substituted or unsubstituted phenazine ring, or a substituted or unsubstituted phenanthroline ring.

In Chemical Formula 1, $Ar^1$ may be a C6 to C30 arene group substituted with an amine group, a C3 to C30 heteroarene group substituted with an amine group, or a condensed ring thereof.

In Chemical Formula 1, $Ar^1$ may be a C6 to C30 arene group unsubstituted with an electron withdrawing group represented by $Ar^2$, a C3 to C30 heteroarene group unsubstituted with the electron withdrawing group represented by $Ar^2$, or condensed rings thereof.

In Chemical Formula 1, the spiro structures may each independently a substituted or unsubstituted C5 to C30 hydrocarbon ring group or a substituted or unsubstituted C2 to C30 heterocyclic group.

The spiro structures in Chemical Formula 1 may each independently include a moiety represented by Chemical Formula 3.

[Chemical Formula 3]

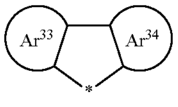

In Chemical Formula 3, $Ar^{33}$ and $Ar^{34}$ may each independently be a substituted or unsubstituted C6 to C30 arene group, a substituted or unsubstituted C3 to C30 heteroarene group, or a condensed ring thereof, and

* may indicate a linking point that is linked to Chemical Formula 1.

The spiro structures in Chemical Formula 1 may each independently include one of the moieties represented by Chemical Formula 4.

[Chemical Formula 4]

(1)

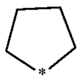

(2)

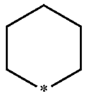

(3)

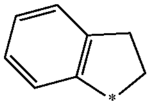

(4)

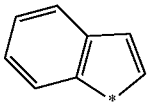

(5)

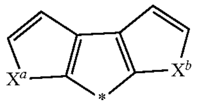

(6)

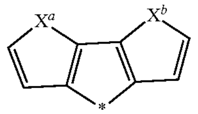

(7)

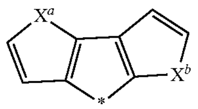

(8)

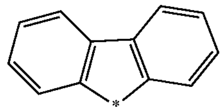

(9)

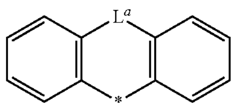

(10)

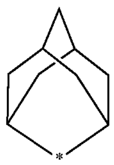

In Chemical Formula 4, $X^a$ and $X^b$ may each independently be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, or —$GeR^{dd}R^{ee}$—, wherein $R^{a1}$, $R^{a2}$, $R^b$, $R^c$, $R^d$, and $R^e$ may each independently be hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and each of $R^{bb}$ and $R^{cc}$ or $R^{dd}$ and $R^{ee}$ may be linked to each other to provide a ring structure, $L^a$ may be —O—, —S—, —Se—, —Te—, —$NR^{a1}$—, —$BR^{a2}$—, —$SiR^bR^c$—, —$GeR^dR^e$—, —$(CR^fR^g)_{n1}$—, —$(C(R^p)$=N))—, or a single bond, wherein $R^{a1}$, $R^{a2}$, $R^b$, $R^c$, $R^d$, $R^e$, $R^f$, $R^g$, and $R^p$ may each independently be hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and n1 of —$(CR^fR^g)_{n1}$— is 1 or 2, at least one hydrogen of each ring may be not replaced or may be replaced by at least one substituent of deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and

* may indicate a linking point that is linked to Chemical Formula 1.

In Chemical Formula 4, at least one CH present in an aromatic ring of at least one of the moieties (3), (4), (5), (6), (7), (8), or (9) may be replaced by N.

In Chemical Formula 1, $Ar^2$ may be a cyclic group represented by Chemical Formula 5.

[Chemical Formula 5]

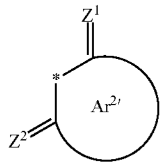

In Chemical Formula 5, $Ar^{2'}$ may be a substituted or unsubstituted C6 to C30 aryl group or a substituted or unsubstituted C3 to C30 heteroaryl group, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, and

* may indicate a linking point that is linked to Chemical Formula 1.

In Chemical Formula 1, $Ar^2$ may be a cyclic group represented by any one of Chemical Formulas 6A to 6G.

[Chemical Formula 6A]

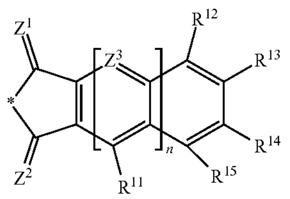

In Chemical Formula 6A, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen, deuterium, or a substituted or unsubstituted C1 to C10 alkyl group, $R^{11}$, $R^{12}$, $R^{13}$, $R^{14}$, and $R^{15}$ may each independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, wherein $R^{11}$, $R^{12}$, $R^{13}$, $R^{14}$, and $R^{15}$ may each independently be present or a pair of $R^{12}$ and $R^{13}$ or a pair of $R^{14}$ and $R^{15}$ may be linked to each other to provide an aromatic ring, n may be 0 or 1, and

* may indicate a linking point that is linked to Chemical Formula 1.

[Chemical Formula 6B]

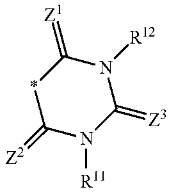

In Chemical Formula 6B, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $R^{11}$ and $R^{12}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* may indicate a linking point that is linked to Chemical Formula 1.

[Chemical Formula 6C]

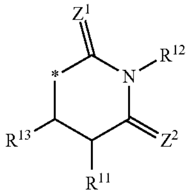

In Chemical Formula 6C, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* may indicate a linking point that is linked to Chemical Formula 1.

[Chemical Formula 6D]

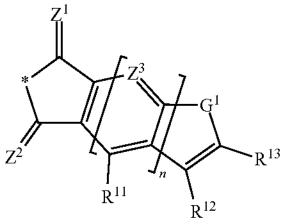

In Chemical Formula 6D, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen or a substituted or unsubstituted C1 to C10 alkyl group, $G^1$ may be O, S, Se, Te, $SiR^xR^y$, or $GeR^zR^w$, wherein $R^x$, $R^y$, $R^z$, and R* may each independently be hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, wherein $R^{12}$ and $R^{13}$ may each independently be present or a pair of $R^{12}$ and $R^{13}$ may be linked to each other to provide an aromatic ring, n may be 0 or 1, and

* may indicate a linking point that is linked to Chemical Formula 1.

[Chemical Formula 6E]

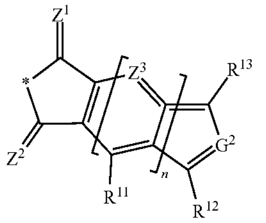

In Chemical Formula 6E, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen or a substituted or unsubstituted C1 to C10 alkyl group, $G^2$ may be O, S, Se, Te, $SiR^xR^y$, or $GeR^zR^w$, wherein $R^x$, $R^y$, $R^z$, and $R^w$ may each independently be hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, n may be 0 or 1, and

* may indicate a linking point that is linked to Chemical Formula 1.

[Chemical Formula 6F]

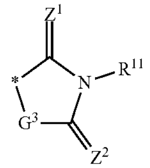

In Chemical Formula 6F, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $R^{11}$ may be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, $G^3$ may be O, S, Se, Te, $SiR^xR^y$, or $GeR^zR^w$, wherein $R^x$, $R^y$, $R^z$, and $R^w$ may each independently be hydrogen, deuterium, a halogen, a cyano group, a substituted or unsubstituted C1 to C20 alkyl group, or a substituted or unsubstituted C6 to C20 aryl group, and

* may indicate a linking point that is linked to Chemical Formula 1.

[Chemical Formula 6G]

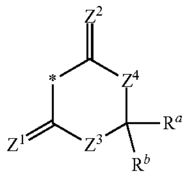

In Chemical Formula 6G, $R^a$ and $R^b$ may each independently be hydrogen, a substituted or unsubstituted C1 to C10 alkyl group, a cyano group, or a cyano-containing group, $Z^1$ to $Z^4$ may each independently be O, S, Se, Te, or $CR^cR^d$, wherein $R^c$ and $R^d$ may each independently be hydrogen, a substituted or unsubstituted C1 to C10 alkyl group, a cyano group, or a cyano-containing group, and

* may indicate a linking point that is linked to Chemical Formula 1.

A sublimation temperature of the compound represented by Chemical Formula 1 may be equal to or greater than about 100° C. and less than or equal to about 390° C.

According to some example embodiments, a photoelectric device (e.g., organic photoelectric device) includes a first electrode and a second electrode facing each other, and a light absorbing layer between the first electrode and the second electrode, wherein the light absorbing layer is configured to absorb light of a red wavelength spectrum, a green wavelength spectrum, a blue wavelength spectrum, an infrared wavelength spectrum, or any combination thereof, the light absorbing layer includes a p-type semiconductor and an n-type semiconductor, and one of the p-type semiconductor or the n-type semiconductor includes the compound represented by Chemical Formula 1.

According to some example embodiments, a light absorption sensor including the photoelectric device is provided.

The light absorption sensor may include a semiconductor substrate integrated with a plurality of first photo-sensing devices sensing light in a blue wavelength region and a plurality of second photo-sensing devices sensing light in a red wavelength region, and the photoelectric device on the semiconductor substrate and selectively sensing light in a green wavelength region.

The light absorbing layer may include an n-type semiconductor that includes the compound represented by Chemical Formula 1, and a p-type semiconductor that includes a compound represented by Chemical Formula 7.

[Chemical Formula 7]

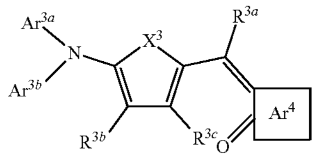

In Chemical Formula 7, $X^3$ may be O, S, Se, Te, S(═O), $S(═O)_2$, $SiR^aR^b$, $GeR^cR^d$, or $CR^eR^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide a spiro structure, $Ar^{3a}$ and $Ar^{3b}$ may each independently be a substituted or unsubstituted C6 to C30 aryl group or a substituted or unsubstituted C3 to C30 heteroaryl group, wherein $Ar^{3a}$ and $Ar^{3b}$ may each independently be present or are linked to each other to provide a fused ring, $Ar^4$ may be a substituted or unsubstituted C6 to C30 arene group, a substituted or unsubstituted C3 to C30 heteroarene group, or a fused ring of two or more thereof, and $R^{3a}$, $R^{3b}$, and $R^{3c}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ may each independently be present or are linked to each other to provide a ring, and $Ar^{3b}$ and $R^{3b}$ may be optionally linked to each other to provide a fused ring.

The p-type semiconductor may be represented by Chemical Formula 7A or Chemical Formula 7B.

[Chemical Formula 7A]

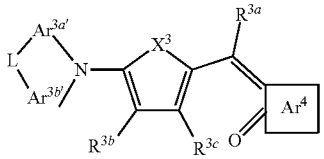

[Chemical Formula 7B]

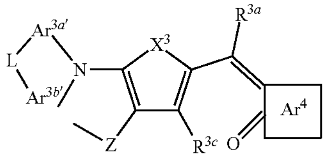

In Chemical Formula 7A and Chemical Formula 7B, $X^3$ may be O, S, Se, Te, S(=O), S(=O)$_2$, $SiR^aR^b$, $GeR^cR^d$, or $CR^eR^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide a spiro structure, $Ar^{3a\prime}$ and $Ar^{3b\prime}$ may each independently be a substituted or unsubstituted C6 to C30 arene group or a substituted or unsubstituted C3 to C30 heteroarene group, $Ar^4$ may be a substituted or unsubstituted C6 to C30 arene group, a substituted or unsubstituted C3 to C30 heteroarene group, or a fused ring of two or more thereof, L and Z may each independently be a single bond, O, S, Se, Te, S(=O), S(=O)$_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, wherein $R^f$, $R^g$, $R^h$, $R^i$, $R^j$, $R^k$, and $R^l$ may each independently be hydrogen, deuterium, a substituted or unsubstituted C1 to C20 alkyl group, or a substituted or unsubstituted C6 to C20 aryl group, and $R^{3a}$, $R^{3b}$, and $R^{3c}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ may each independently be present or are linked to each other to provide a ring.

The light absorbing layer may include a p-type semiconductor that includes the compound represented by Chemical Formula 1, and an n-type semiconductor that includes fullerene, a fullerene derivative, subphthalocyanine or subphthalocyanine derivative, thiophene or a thiophene derivative, or a compound represented by Chemical Formula 8.

[Chemical Formula 8]

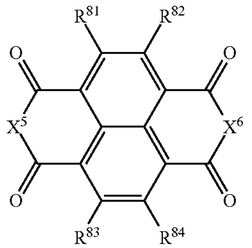

In Chemical Formula 8, $X^5$ and $X^6$ may each independently be O or $NR^a$, wherein $R^a$ may be hydrogen, a substituted or unsubstituted C1 to C30 alkyl group, a substituted or unsubstituted C6 to C30 aryl group, a substituted or unsubstituted C3 to C30 heterocyclic group, a halogen, or a cyano group, and $R^{81}$ to $R^{84}$ may each independently be hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

The first photo-sensing device and the second photo-sensing device may be stacked in a vertical direction in the semiconductor substrate.

The light absorption sensor may further include a color filter layer including a blue filter selectively transmitting light in a blue wavelength region and a red filter selectively transmitting light in a red wavelength region.

The light absorption sensor may include the photoelectric device, wherein the photoelectric device is a green photoelectric device configured to sense light in a green wavelength region, and a semiconductor substrate integrated with a plurality of first photo-sensing devices configured to sense light in a blue wavelength region and a plurality of second photo-sensing devices configured to sense light in a red wavelength region, wherein the photoelectric device is on the semiconductor substrate.

The light absorption sensor may include the photoelectric device, wherein the photoelectric device is a green photoelectric device configured to sense light in a green wavelength region, and the light absorption sensor may include a stack of the green photoelectric device, a blue photoelectric device configured to selectively absorb light in a blue wavelength region, and a red photoelectric device configured to selectively absorb light in a red wavelength region.

According to some example embodiments, a sensor-embedded display panel may include a substrate, a light emitting element disposed on the substrate and including a light emitting layer, and a light absorption sensor disposed on the substrate and comprising a light absorbing layer, the light absorbing layer being arranged in parallel with the light emitting layer along an in-plane direction of the substrate such that the light absorbing layer and the light emitting layer at least partially overlap in the in-plane direction, wherein the light absorbing layer is configured to absorb light of a red wavelength spectrum, a green wavelength spectrum, a blue wavelength spectrum, an infrared wavelength spectrum, or any combination thereof, the light absorbing layer includes a p-type semiconductor and an n-type semiconductor, and one of the p-type semiconductor or the n-type semiconductor includes the compound represented by Chemical Formula 1.

The light emitting element may include first, second and third light emitting elements configured to emit light of different wavelength spectra, and the light absorption sensor may be configured to absorb light emitted from at least one of the first, second, or third light emitting elements and then reflected by the recognition target to the light absorption sensor and to convert the absorbed light into an electrical signal.

The light emitting element and the light absorption sensor may each include a separate portion of a common electrode configured to apply a common voltage to the light emitting element and the light absorption sensor, and the sensor-embedded display panel may further include a first common auxiliary layer that is a single piece of material that extends continuously between the light emitting layer and the common electrode and between the light absorbing layer and the common electrode.

A difference between a LUMO energy level of the first common auxiliary layer and a LUMO energy level of the compound represented by Chemical Formula 1 may be less than or equal to about 1.2 eV.

The sensor-embedded display panel may further include a second common auxiliary layer that is a single piece of material that extends continuously between the light emitting layer and the substrate and between the light absorbing layer and the substrate.

The light emitting element may include first, second, and third light emitting elements configured to emit light of any one wavelength spectrum of the red wavelength spectrum, the green wavelength spectrum, or the blue wavelength spectrum, and the light absorbing layer may be configured to absorb light having a same wavelength spectrum as light emitted from at least one of the first, second, or third light emitting elements.

The sensor-embedded display panel may include a display area configured to display a color and a non-display area excluding the display area, and the light absorption sensor may be in the non-display area.

The display area may include a plurality of first subpixels configured to display light of the red wavelength spectrum and comprising the first light emitting element, a plurality of second subpixels configured to display light of the green wavelength spectrum and comprising the second light emitting element, and a plurality of third subpixels configured to display light of the blue wavelength spectrum and comprising the third light emitting element, and the light absorption sensor may be between at least two subpixels of a first subpixel of the plurality of first subpixels, a second subpixel of the plurality of second subpixels, or a third subpixel of the plurality of third subpixels.

The light absorbing layer may include the compound represented by Chemical Formula 1 as an n-type semiconductor and the compound represented by Chemical Formula 7 as a p-type semiconductor.

The p-type semiconductor may be represented by Chemical Formula 7A or Chemical Formula 7B.

The compound represented by Chemical Formula 1 may be included as a p-type semiconductor, and the n-type semiconductor may include fullerene, a fullerene derivative, subphthalocyanine or a subphthalocyanine derivative, thiophene or a thiophene derivative, or a compound represented by Chemical Formula 8.

According to some example embodiments, an electronic device including the sensor or a sensor-embedded display panel is provided.

In some example embodiments, a photoelectric device may include a first electrode and a second electrode facing each other, and a light absorbing layer between the first electrode and the second electrode. The light absorbing layer may include a compound represented by Chemical Formula 1.

The light absorbing layer may further include a compound represented by Chemical Formula 7.

The light absorbing layer may further include a compound represented by Chemical Formula 8.

The compound represented by Chemical Formula 1 has excellent light absorption in the whole green wavelength region, and thus may be suitably used in a photoelectric device or a sensor, particularly a sensor-embedded display panel.

DETAILED DESCRIPTION

Figure 1:
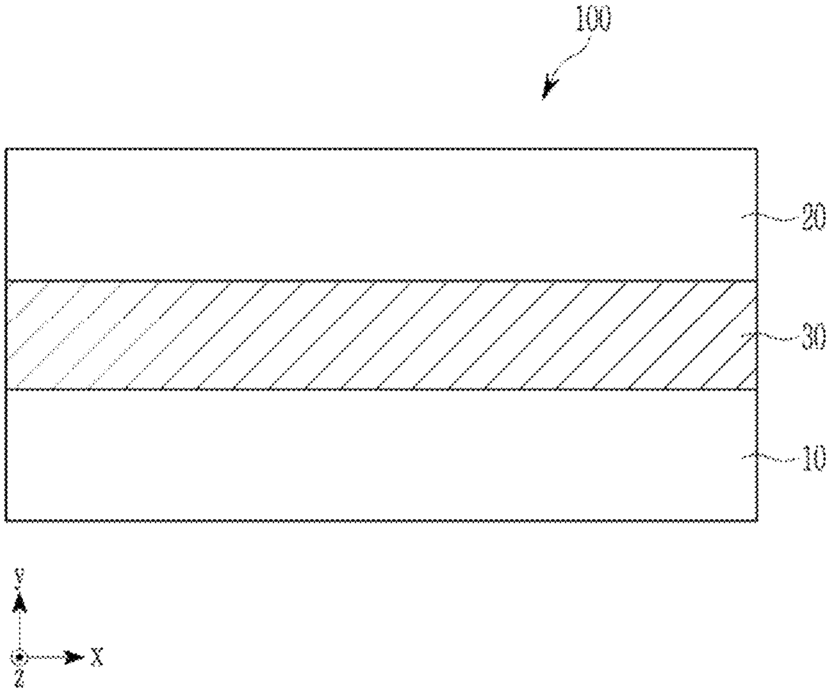
FIG. 1 is a cross-sectional view illustrating a photoelectric device according to some example embodiments.

Hereinafter, example embodiments will be described in detail so that a person skilled in the art would understand the same. However, a structure that is actually applied may be implemented in various different forms and is not limited to the example embodiments described herein.

In the drawings, the thickness of layers, films, panels, regions, etc., are exaggerated for clarity. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the example embodiments, and the same or similar constituent elements are indicated by the same reference numeral throughout the specification.

As used herein, "at least one of A, B, or C," "one of A, B, C, or any combination thereof" and "one of A, B, C, and any combination thereof" refer to each constituent element, and any combination thereof (e.g., A; B; C; A and B; A and C; B and C; or A, B, and C).

Hereinafter, the terms "lower" and "upper" are used for better understanding and ease of description, but do not limit the location relationship.

As used herein, when a definition is not otherwise provided, "substituted" refers to replacement of hydrogen of a compound or a functional group by a substituent selected from a halogen (F, Br, Cl, or I), a hydroxy group, a nitro group, a cyano group, an amine group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and any combination thereof.

As used herein, when a definition is not otherwise provided, "hetero" refers to one including 1 to 4 heteroatoms selected from N, O, S, Se, Te, Si, and P.

As used herein, when a definition is not otherwise provided, "alkyl group" may be a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, when a definition is not otherwise provided, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, when a definition is not otherwise provided, "aryl group" refers to a substituent in which all ring-forming elements have p-orbitals which form conjugation, and it may be a monocyclic, polycyclic or fused-ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. As used herein, when a definition is not otherwise provided, the cyano-containing group also refers to a divalent group such as $=CR^{x'}-(CR^xR^y)_p-CR^{y'}(CN)_2$ wherein $R^x$, $R^y$, $R^{x'}$, and $R^{y'}$ may each independently be hydrogen or a C1 to C10 alkyl group and p is an integer of 0 to 10 (or 1 to 10). As a monovalent functional group, specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, when a definition is not otherwise provided, "hydrocarbon cyclic group" may be a C3 to C30 hydrocarbon cyclic group. The hydrocarbon cyclic group may be an arene group (e.g., a C6 to C30 arene group, a C6 to C20 arene group, or a C6 to C10 arene group), an alicyclic hydrocarbon cyclic group (e.g., a C3 to C30 cycloalkyl group, a C5 to C30 cycloalkyl group, a C3 to C20 cycloalkyl group, or a C3 to C10 cycloalkyl group) or a fused ring thereof. For example the fused ring thereof may refer to a fused ring of an aromatic ring (arene ring) and a non-aromatic ring (alicyclic ring), for example a fused ring of at least one aromatic ring (arene ring) such as a C6 to C30 arene group, a C6 to C20 arene group, or a C6 to C10 arene group and at least one non-aromatic ring (alicyclic ring) such as a C3 to C30 cycloalkyl group, a C3 to C20 cycloalkyl group, or a C3 to C10 cycloalkyl group.

As used herein, when a definition is not otherwise provided, "heterocyclic group" may be a C2 to C30 heterocyclic group. The heterocyclic group refers to a cyclic group including 1 to 3 heteroatoms selected from N, O, S, Se, Te, P, and Si instead of carbon atom(s) in a cyclic group selected from an arene group (e.g., a C6 to C30 arene group, a C6 to C20 arene group, or a C6 to C10 arene group), an alicyclic hydrocarbon cyclic group (e.g., a C3 to C30 cycloalkyl group, a C3 to C20 cycloalkyl group, or a C3 to C10 cycloalkyl group), or a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P, and Si in a cyclic group.

As used herein, when a definition is not otherwise provided, "aromatic hydrocarbon group" includes a C6 to C30 aryl group such as a phenyl group, a naphthyl group, a C6 to C30 arylene group, and the like, but is not limited thereto.

As used herein, when a definition is not otherwise provided, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited thereto.

As used herein, when a definition is not otherwise provided, “aromatic ring” refers to a C5 to C10 cyclic group (e.g., C6 aryl group) providing a conjugated structure or a C2 to C10 heterocyclic group (e.g., C2 to C4 heteroaryl group) providing a conjugated structure.

As used herein, when a definition is not otherwise provided, the energy level is the highest occupied molecular orbital (HOMO) energy level or the lowest unoccupied molecular orbital (LUMO) energy level.

It will further be understood that when an element is referred to as being “on” another element, it may be above or beneath or adjacent (e.g., horizontally adjacent) to the other element. It will be understood that elements and/or properties thereof (e.g., structures, surfaces, directions, or the like), which may be referred to as being “perpendicular,” “parallel,” “coplanar,” or the like with regard to other elements and/or properties thereof (e.g., structures, surfaces, directions, or the like) may be “perpendicular,” “parallel,” “coplanar,” or the like or may be “substantially perpendicular,” “substantially parallel,” “substantially coplanar,” respectively, with regard to the other elements and/or properties thereof. Elements and/or properties thereof (e.g., structures, surfaces, directions, or the like) that are “substantially perpendicular” with regard to other elements and/or properties thereof will be understood to be “perpendicular” with regard to the other elements and/or properties thereof within manufacturing tolerances and/or material tolerances and/or have a deviation in magnitude and/or angle from “perpendicular,” or the like with regard to the other elements and/or properties thereof that is equal to or less than 10% (e.g., a. tolerance of ±10%). Elements and/or properties thereof (e.g., structures, surfaces, directions, or the like) that are “substantially parallel” with regard to other elements and/or properties thereof will be understood to be “parallel” with regard to the other elements and/or properties thereof within manufacturing tolerances and/or material tolerances and/or have a deviation in magnitude and/or angle from “parallel,” or the like with regard to the other elements and/or properties thereof that is equal to or less than 10% (e.g., a. tolerance of ±10%). Elements and/or properties thereof (e.g., structures, surfaces, directions, or the like) that are “substantially coplanar” with regard to other elements and/or properties thereof will be understood to be “coplanar” with regard to the other elements and/or properties thereof within manufacturing tolerances and/or material tolerances and/or have a deviation in magnitude and/or angle from “coplanar,” or the like with regard to the other elements and/or properties thereof that is equal to or less than 10% (e.g., a. tolerance of ±10%). It will be understood that elements and/or properties thereof may be recited herein as being “identical” to, “the same” or “equal” as other elements, and it will be further understood that elements and/or properties thereof recited herein as being “identical” to, “the same” as, or “equal” to other elements may be “identical” to, “the same” as, or “equal” to or “substantially identical” to, “substantially the same” as or “substantially equal” to the other elements and/or properties thereof. Elements and/or properties thereof that are “substantially identical” to, “substantially the same” as or “substantially equal” to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same. While the term “same,” “equal” or “identical” may be used in description of some example embodiments, it should be understood that some imprecisions may exist. Thus, when one element is referred to as being the same as another element, it should be understood that an element or a value is the same as another element within a desired manufacturing or operational tolerance range (e.g., ±10%). It will be understood that elements and/or properties thereof described herein as being the “substantially” the same and/or identical encompasses elements and/or properties thereof that have a relative difference in magnitude that is equal to or less than 10%. Further, regardless of whether elements and/or properties thereof are modified as “substantially,” it will be understood that these elements and/or properties thereof should be construed as including a manufacturing or operational tolerance (e.g., ±10%) around the stated elements and/or properties thereof. When the terms “about” or “substantially” are used in this specification in connection with a numerical value, it is intended that the associated numerical value include a tolerance of ±10% around the stated numerical value. Moreover, when the words “about” and “substantially” are used in connection with geometric shapes, it is intended that precision of the geometric shape is not required but that latitude for the shape is within the scope of the inventive concepts. Further, regardless of whether numerical values or shapes are modified as “about” or “substantially,” it will be understood that these values and shapes should be construed as including a manufacturing or operational tolerance (e.g., ±10%) around the stated numerical values or shapes. When ranges are specified, the range includes all values therebetween such as increments of 0.1%.

As used herein, when a definition is not otherwise provided, a work function or energy level is expressed as an absolute value from a vacuum level. In addition, when the work function or the energy level is referred to be deep, high, or large, it may have a large absolute value based on “0 eV” of the vacuum level while when the work function or the energy level is referred to be shallow, low, or small, it may have a small absolute value based on “0 eV” of the vacuum level. In addition, a difference between the work function and/or the energy level may be a value obtained by subtracting a small value of the absolute value from a large value of the absolute value.

As used herein, when a definition is not otherwise provided, the HOMO energy level may be evaluated by the amount of photoelectrons emitted according to energy by irradiating UV light onto a thin film using AC-2 (Hitachi) or AC-3 (Riken Keiki Co., LTD.).

As used herein, when a definition is not otherwise provided, the LUMO energy level is obtained as follow: an energy bandgap is obtained using a UV-Vis spectrometer (Shimadzu Corporation), and then the LUMO energy level is calculated from the energy bandgap and the measured HOMO energy level.

Hereinafter, a compound according to some example embodiments is described. The compound is represented by Chemical Formula 1.

[Chemical Formula 1]

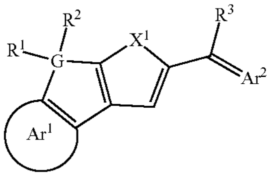

In Chemical Formula 1,

G may be C, Si, or Ge, $R^1$ and $R^2$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, or a cyano group (—CN), wherein $R^1$ and $R^2$ may each independently be present or are linked to each other to provide (e.g., establish, define, etc.) a spiro structure, $X^1$ may be O, S, Se, Te, S(═O), S(═O)$_2$, SiR$^a$R$^b$, GeR$^c$R$^d$, or CR$^e$R$^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide (e.g., establish, define, etc.) a separate spiro structure, $R^3$ may be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, pentafluorosulfanyl group (—SF$_5$), a hydroxyl group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein $R^a$, $R^b$, and $R^c$ may each independently be hydrogen or a substituted or unsubstituted C1 to C10 alkyl group), or any combination thereof, $Ar^1$ may be a substituted or unsubstituted C6 to C30 arene group, a substituted or unsubstituted C3 to C30 heteroarene group, or a condensed ring thereof, and $Ar^2$ may be a substituted or unsubstituted C6 to C30 hydrocarbon cyclic group including at least one functional group of C═O, C═S, C═Se, C═Te, or C═CR$^a$R$^b$, wherein $R^a$ and $R^b$ may each independently be hydrogen, a substituted or unsubstituted C1 to C10 alkyl group, a cyano group or a cyano-containing group; a substituted or unsubstituted C2 to C30 heterocyclic group including at least one functional group of C═O, C═S, C═Se, C═Te, or C═CR$^a$R$^b$, (wherein $R^a$ and $R^b$ may each independently be hydrogen, a substituted or unsubstituted C1 to C10 alkyl group, a cyano group, or a cyano-containing group), or a fused ring thereof.

The compound represented by Chemical Formula 1 includes an electron donor moiety of at least three aromatic rings and an electron acceptor moiety represented by $Ar^2$. In Chemical Formula 1, the electron donor moiety induces a planar structure to improve charge mobility of the compound.

In Chemical Formula 1, $X^1$ may be O, S, Se, or Te.

In Chemical Formula 1, $Ar^1$ may be one of moieties represented by Chemical Formula 2.

[Chemical Formula 2]

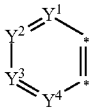

(1)

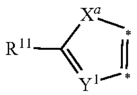

(2)

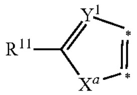

(3)

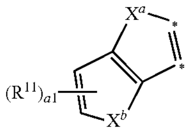

(4)

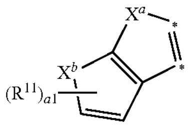

(5)

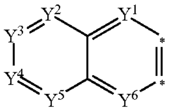

(6)

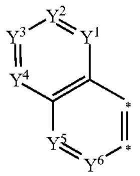

(7)

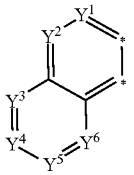

(8)

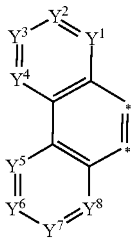

(9)

-continued (10)

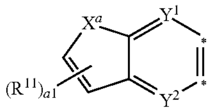

(11)

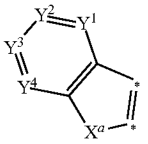

(12)

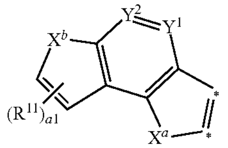

(13)

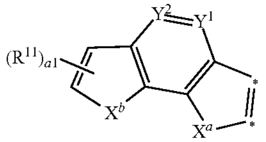

(14)

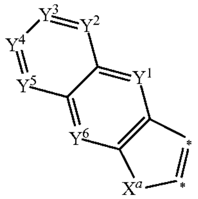

(15)

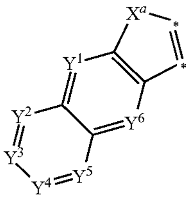

(16)

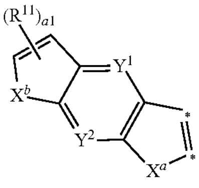

(17)

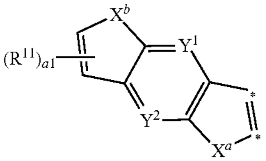

(18)

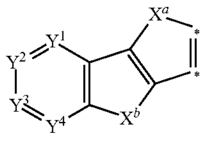

-continued (19)

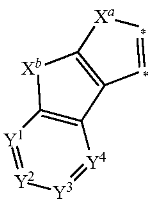

In Chemical Formula 2, $Y^1$ to $Y^8$ may each independently be N or $CR^p$, wherein $R^p$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to provide a substituted or unsubstituted C6 to C30 arene group, a substituted or unsubstituted C3 to C30 heteroarene group, or a condensed ring thereof, $X^a$ and $X^b$ may each independently be O, S, Se, Te, S(=O), $S(=O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ may each independently be hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ may each independently be present or at least one pair of $R^b$ and $R^c$, $R^d$ and $R^e$, or $R^f$ and $R^g$ may be linked to each other to provide (e.g., establish, define, etc.) a spiro structure, $R^{11}$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 may be an integer of 0 to 2 (e.g., a1 may be 0, 1, or 2), and

* is (e.g., indicates) a point (e.g., a linking point) linked to the pentagonal ring of Chemical Formula 1 (i.e., the pentagonal ring including G in Chemical Formula 1).

In Chemical Formula 1, $Ar^1$ may be one of moieties represented by Chemical Formula 2A.

[Chemical Formula 2A]

(1)

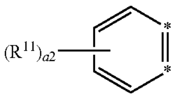

(2)

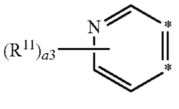

(3)

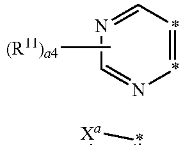

(4)

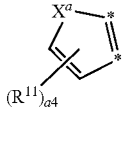

-continued (5)

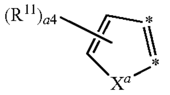

In Chemical Formula 2A, $X^a$ may be O, S, Se, Te, S(=O), $S(=O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ may each independently be hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ may each independently be present or at least one pair of $R^b$ and $R^c$, $R^d$ and $R^e$, or $R^f$ and $R^g$ may be linked to each other to provide (e.g., establish, define, etc.) a spiro structure, $R^{11}$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a2 may be an integer from 0 to 4 (e.g., a2 may be one of 0, 1, 2, 3, or 4), a3 may be an integer from 0 to 3 (e.g., a3 may be one of 0, 1, 2, or 3), a4 may be an integer from 0 to 2 (e.g., a4 may be one of 0, 1, or 2), and

* is (e.g., indicates) a point (e.g., a linking point) linked to a pentagonal ring of Chemical Formula 1 (i.e., the pentagonal ring including G in Chemical Formula 1).

In Chemical Formula 1, $Ar^1$ may be a substituted or unsubstituted benzene ring, a substituted or unsubstituted naphthalene ring, a substituted or unsubstituted anthracene ring, a substituted or unsubstituted indene ring, a substituted or unsubstituted phenanthrene ring, a substituted or unsubstituted fluorene ring, or a substituted or unsubstituted acenaphthylene ring. Here, "substituted" refers to replacement of hydrogen of the aromatic ring by a substituent of deuterium, a C1 to C30 alkyl group, a C1 to C30 alkoxy group, a C6 to C30 aryl group, a C3 to C30 heteroaryl group, a C2 to C30 acyl group, a halogen, a cyano group (—CN), a cyano-containing group, a nitro group, $—SiR^aR^bR^c$ (wherein $R^a$, $R^b$, and $R^c$ are each independently hydrogen or a substituted or unsubstituted C1 to C10 alkyl group), or any combination thereof.

In Chemical Formula 1, $Ar^1$ may be a substituted or unsubstituted thiophene ring, a substituted or unsubstituted selenophene ring, a substituted or unsubstituted tellurophene ring, a substituted or unsubstituted pyridine ring, a substituted or unsubstituted pyrimidine ring, a substituted or unsubstituted pyrazine ring, a substituted or unsubstituted indole ring, a substituted or unsubstituted quinoline ring, a substituted or unsubstituted isoquinoline ring, a substituted or unsubstituted quinoxaline ring, a substituted or unsubstituted quinazoline ring, a substituted or unsubstituted carbazole ring, a substituted or unsubstituted phenazine ring, or a substituted or unsubstituted phenanthroline ring. Here, "substituted" refers to replacement of hydrogen of the aromatic ring by a substituent of deuterium, a C1 to C30 alkyl group, a C1 to C30 alkoxy group, a C6 to C30 aryl group, a C3 to C30 heteroaryl group, a C2 to C30 acyl group, a halogen, a cyano group (—CN), a cyano-containing group, a nitro group, $—SiR^aR^bR^c$ (wherein $R^a$, $R^b$, and $R^c$ are each independently hydrogen or a substituted or unsubstituted C1 to C10 alkyl group), or any combination thereof.

In Chemical Formula 1, $Ar^1$ may be a C6 to C30 arene group substituted with an amine group (e.g., NRR', wherein R and R' may each independently be hydrogen, deuterium, a C1 to C20 alkyl group, or a C6 to C20 aryl group, or R and R' may be linked to each other to provide an N-containing C6 to C30 heteroaryl group (e.g., a substituted or unsubstituted carbazolyl group, a substituted or unsubstituted acridinyl group, and the like)), a C3 to C30 heteroarene group substituted with the amine group, or a condensed ring thereof.

In Chemical Formula 1, $Ar^1$ may not include an electron withdrawing group represented by $Ar^2$. $Ar^1$ may be a C6 to C30 arene group unsubstituted with an electron withdrawing group represented by $Ar^2$, a C3 to C30 heteroarene group unsubstituted with the electron withdrawing group represented by $Ar^2$, or condensed rings thereof. The electron withdrawing group may be a cyclic group represented by $Ar^2$ (a substituted or unsubstituted C6 to C30 hydrocarbon ring group having at least one functional group of C=O, C=S, C=Se, or C=Te, a substituted or unsubstituted C2 to C30 heterocyclic group having at least one functional group of C=O, C=S, C=Se, or C=Te, or a fused ring thereof). Accordingly, the structure of Chemical Formula 1 may have a donor-acceptor structure, and thereby the absorption wavelength may be adjusted in the whole range of the green wavelength (about 500 nm to about 580 nm, for example, about 520 nm to about 580 nm), and the deposition temperature may be lowered and the absorption coefficient may be increased. When an electron withdrawing group represented by $Ar^2$ is included as a substituent of $Ar^1$, a sublimation temperature is too high, and deposition stability and processability may be deteriorated.

In Chemical Formula 1, $R^1$ and $R^2$ may be independently present or may be linked to each other to provide (e.g., establish, define, etc.) a spiro structure. The spiro structure may be a substituted or unsubstituted C5 to C30 hydrocarbon ring group or a substituted or unsubstituted C2 to C30 heterocyclic group.

The substituted or unsubstituted C5 to C30 hydrocarbon cyclic group may be, for example, a substituted or unsubstituted C5 to C30 cycloalkyl group (e.g., a substituted or unsubstituted C3 to C20 cycloalkyl group or a substituted or unsubstituted C3 to C10 cycloalkyl group); or a fused ring of at least one substituted or unsubstituted C5 to C30 cycloalkyl group (e.g., a substituted or unsubstituted C3 to C20 cycloalkyl group or a substituted or unsubstituted C3 to C10 cycloalkyl group) and at least one substituted or unsubstituted C6 to C30 aryl group (e.g., a substituted or unsubstituted C6 to C20 aryl group or a substituted or unsubstituted C3 to C10 aryl group). Examples of the fused ring include a fluorenyl group, an indanyl group, and the like.

The substituted or unsubstituted C2 to C30 heterocyclic group may be for example a substituted or unsubstituted C2 to C30 heterocycloalkyl group (e.g., a substituted or unsubstituted C2 to C20 heterocycloalkyl group or a substituted or unsubstituted C2 to C10 heterocycloalkyl group). In addition, the substituted or unsubstituted C2 to C30 heterocyclic group may mean that the fused ring exemplified by the substituted or unsubstituted C5 to C30 hydrocarbon ring group includes at least one hetero atom. For example, the substituted or unsubstituted C2 to C30 heterocyclic group may be a fused ring of at least one substituted or unsubstituted C5 to C30 heterocycloalkyl group (e.g., a substituted or unsubstituted C3 to C20 heterocycloalkyl group or a substituted or unsubstituted C3 to C10 heterocycloalkyl group) and at least one substituted or unsubstituted C6 to C30 aryl group (e.g., a substituted or unsubstituted C6 to C20 aryl group or a substituted or unsubstituted C3 to C10 aryl group); a fused ring of at least one substituted or unsubstituted C5 to C30 cycloalkyl group (e.g., a substituted or unsubstituted C3 to C20 cycloalkyl group or a substituted or unsubstituted C3 to C10 cycloalkyl group) and at least one substituted or unsubstituted C6 to C30 heteroaryl group (e.g., a substituted or unsubstituted C6 to C20 heteroaryl group or a substituted or unsubstituted C3 to C10 heteroaryl group); a fused ring of at least one substituted or unsubstituted C5 to C30 heterocycloalkyl group (e.g., a substituted or unsubstituted C3 to C20 heterocycloalkyl group or a substituted or unsubstituted C3 to C10 heterocycloalkyl group) and at least one substituted or unsubstituted C6 to C30 heteroaryl group (e.g., a substituted or unsubstituted C6 to C20 heteroaryl group or a substituted or unsubstituted C3 to C10 heteroaryl group).

In Chemical Formula 1, $R^1$ and $R^2$ may be independently present or may be linked to each other to provide (e.g., establish, define, etc.) a spiro structure. The spiro structure (and/or the separate spiro structure provided by at least one pair of $R^b$ and $R^c$, $R^d$ and $R^e$, or $R^f$ and $R^g$ linked to each other when $X^1$ of Chemical Formula 1 and $X^a$ and $X^b$ of Chemical Formula 2 are each independently $SiR^bR^c$, $GeR^dR^e$, or $CR^fR^g$) may comprise a moiety represented by Chemical Formula 3.

[Chemical Formula 3]

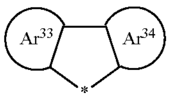

In Chemical Formula 3, $Ar^{33}$ and $Ar^{34}$ may each independently be a substituted or unsubstituted C6 to C30 arene group, a substituted or unsubstituted C3 to C30 heteroarene group, or a condensed ring thereof, and

* indicates a linking point that is linked to Chemical Formula 1.

In Chemical Formula 1, $R^1$ and $R^2$ may be independently present or may be linked to each other to provide (e.g., establish, define, etc.) a spiro structure. The spiro structure (and/or the separate spiro structure provided by at least one pair of $R^b$ and $R^c$, $R^d$ and $R^e$, or $R^f$ and $R^g$ linked to each other when $X^1$ of Chemical Formula 1 and $X^a$ and $X^b$ of Chemical Formula 2 are each independently $SiR^bR^c$, $GeR^dR^e$, or $CR^fR^g$) may include one of the moieties represented by Chemical Formula 4.

[Chemical Formula 4]

(1)

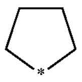

(2)

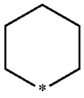

(3)

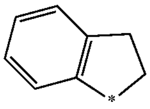

(4)

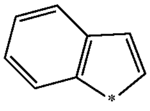

-continued (5)

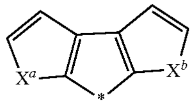

(6)

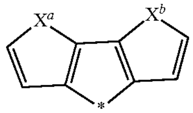

(7)

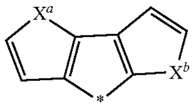

(8)

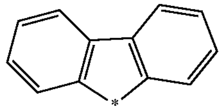

(9)

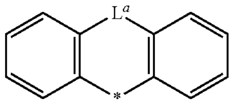

(10)

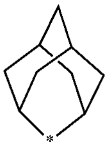

In Chemical Formula 4, $X^a$ and $X^b$ may each independently be —O—, —S—, —Se—, —Te—, —S(═O)—, —S(═O)$_2$—, —NR$^{a1}$—, —BR$^{a2}$—, —SiR$^b$R$^c$—, —SiR$^{bb}$R$^{cc}$—, -GeR$^d$R$^e$—, or —GeR$^{dd}$R$^{ee}$—, wherein $R^{a1}$, $R^{a2}$, $R^b$, $R^c$, $R^d$, and $R^e$ may each independently be hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and each pair of $R^{bb}$ and $R^{cc}$ or $R^{dd}$ and $R^{ee}$ may be linked to each other to provide (e.g., establish, define, etc.) a ring structure, $L^a$ may be —O—, —S—, —Se—, —Te—, —NR$^{a1}$—, —BR$^{a2}$—, —SiR$^b$R$^c$—, —GeR$^d$R$^e$—, —(CR$^f$R$^g$)$_{n1}$—, —(C(R$^p$)═N))—, or a single bond, wherein $R^{a1}$, $R^{a2}$, $R^b$, $R^c$, $R^d$, $R^e$, $R^f$, $R^g$, and $R^p$ may each independently be hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and n1 of —(CR$^f$R$^g$)$_{n1}$— is 1 or 2, at least one hydrogen of each ring may be not replaced (e.g., may be present) or may be replaced by at least one substituent of deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and

* indicates a linking point that is linked to Chemical Formula 1.

In Chemical Formula 4, at least one CH present in an aromatic ring of at least one of the moiety (3), (4), (5), (6), (7), (8), or (9) may be replaced by nitrogen (N).

In Chemical Formula 1, $Ar^2$ may be a cyclic group represented by Chemical Formula 5.

[Chemical Formula 5]

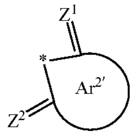

In Chemical Formula 5, $Ar^{2\prime}$ may be a substituted or unsubstituted C6 to C30 aryl group or a substituted or unsubstituted C3 to C30 heteroaryl group, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group. In some example embodiments, when both $Z^1$ and $Z^2$ are $CR^aR^b$, at least one of $Z^1$ or $Z^2$ may include a cyano group or a cyano-containing group, and

* may indicate a linking point that is linked to Chemical Formula 1.

In Chemical Formula 1, $Ar^2$ may be a cyclic group represented by one of Chemical Formula 6A to Chemical Formula 6G.

[Chemical Formula 6A]

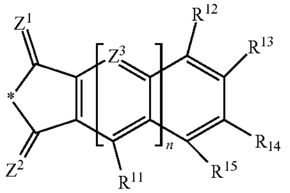

In Chemical Formula 6A, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen, deuterium, or a substituted or unsubstituted C1 to C10 alkyl group, $R^{11}$, $R^{12}$, $R^{13}$, $R^{14}$, and $R^{15}$ may be the same or different and may each independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, wherein $R^{11}$, $R^{12}$, $R^{13}$, $R^{14}$, and $R^{15}$ may each independently be present or a pair of $R^{12}$ and $R^{13}$ or a pair of $R^{14}$ and $R^{15}$ may be linked to each other to provide (e.g., establish, define, etc.) an aromatic ring, n may be 0 or 1, and

* indicates a linking point that is linked to Chemical Formula 1.

In some example embodiments, when both $Z^1$ and $Z^2$ of Chemical Formula 6A are $CR^aR^b$, at least one of $Z^1$ or $Z^2$ may include a cyano group or a cyano-containing group.

[Chemical Formula 6B]

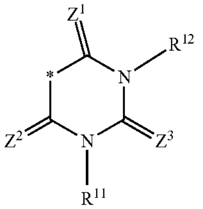

In Chemical Formula 6B, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be O, S, Se, Te, or $C(R^a)(CN)$, wherein $R^a$ may be hydrogen, a cyano group (—CN), or a C1 to C10 alkyl group, $R^{11}$ and $R^{12}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* indicates a linking point that is linked to Chemical Formula 1.

In some example embodiments, when both $Z^1$ and $Z^2$ of Chemical Formula 6B are $CR^aR^b$, at least one of $Z^1$ or $Z^2$ may include a cyano group or a cyano-containing group.

[Chemical Formula 6C]

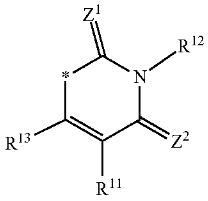

In Chemical Formula 6C, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* indicates a linking point that is linked to Chemical Formula 1.

In some example embodiments, when both $Z^1$ and $Z^2$ of Chemical Formula 6C are $CR^aR^b$, at least one of $Z^1$ or $Z^2$ may include a cyano group or a cyano-containing group.

[Chemical Formula 6D]

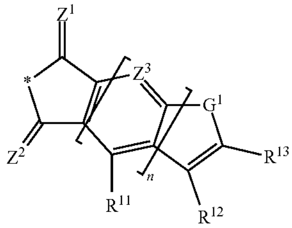

In Chemical Formula 6D, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen or a substituted or unsubstituted C1 to C10 alkyl group, $G^1$ may be O, S, Se, Te, $SiR^xR^y$ and $GeR^zR^w$, wherein $R^x$, $R^y$, $R^z$, and $R^w$ may each independently be hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, wherein $R^{12}$ and $R^{13}$ may each independently be present or may be linked to each other to provide (e.g., establish, define, etc.) a fused aromatic ring, n may be 0 or 1, and

* indicates a linking point that is linked to Chemical Formula 1.

In some example embodiments, when both $Z^1$ and $Z^2$ of Chemical Formula 6D are $CR^aR^b$, at least one of $Z^1$ or $Z^2$ may include a cyano group or a cyano-containing group.

[Chemical Formula 6E]

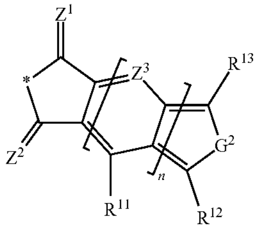

In Chemical Formula 6E, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $Z^3$ may be N or $CR^c$, wherein $R^c$ may be hydrogen or a substituted or unsubstituted C1 to C10 alkyl group, $G^2$ may be O, S, Se, Te, $SiR^xR^y$ and $GeR^zR^w$, wherein $R^x$, $R^y$, $R^z$, and $R^w$ may each independently be hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, n may be 0 or 1, and

* indicates a linking point that is linked to Chemical Formula 1.

In some example embodiments, when both $Z^1$ and $Z^2$ of Chemical Formula 6E are $CR^aR^b$, at least one of $Z^1$ or $Z^2$ may include a cyano group or a cyano-containing group.

[Chemical Formula 6F]

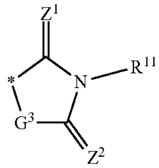

In Chemical Formula 6F, $Z^1$ and $Z^2$ may each independently be O, S, Se, Te, or $CR^aR^b$, wherein $R^a$ and $R^b$ may each independently be hydrogen, a substituted or unsubstituted C1 to C10 alkyl group, a cyano group, or a cyano-containing group, $R^{11}$ may be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, $G^3$ may be O, S, Se, Te, $SiR^xR^y$ and $GeR^zR^w$, wherein $R^x$, $R^y$, $R^z$ and $R^w$ may each independently be hydrogen, deuterium, a halogen, a cyano group, a substituted or unsubstituted C1 to C20 alkyl group, or a substituted or unsubstituted C6 to C20 aryl group, and

* indicates a linking point that is linked to Chemical Formula 1.

In some example embodiments, when both $Z^1$ and $Z^2$ of Chemical Formula 6F are $CR^aR^b$, at least one of $Z^1$ or $Z^2$ may include a cyano group or a cyano-containing group.

[Chemical Formula 6G]

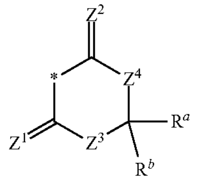

In Chemical Formula 6G, $R^a$ and $R^b$ may each independently be hydrogen, a substituted or unsubstituted C1 to C10 alkyl group, a cyano group, or a cyano-containing group, $Z^1$ to $Z^4$ may each independently be O, S, Se, Te, or $CR^cR^d$, wherein $R^c$ and $R^d$ may each independently be hydrogen, a substituted or unsubstituted C1 to C10 alkyl group, a cyano group, or a cyano-containing group.

In some example embodiments, when both $Z^1$ and $Z^2$ of Chemical Formula 6G are $CR^aR^b$, at least one of $Z^1$ or $Z^2$ may include a cyano group or a cyano-containing group.

The cyclic group represented by Chemical Formula 6A may be a cyclic group represented by Chemical Formula 6A-1 or Chemical Formula 6A-2.

[Chemical Formula 6A-1]

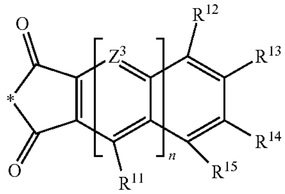

[Chemical Formula 6A-2]

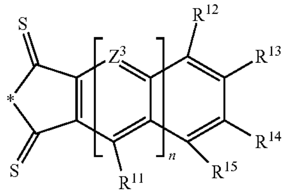

In Chemical Formula 6A-1 and Chemical Formula 6A-2, $Z^3$, $R^{11}$, n, $R^{12}$, $R^{13}$, $R^{14}$, and $R^{15}$ are the same as $Z^3$, $R^{11}$, n, $R^{12}$, $R^{13}$, $R^{14}$, and $R^{15}$, respectively, in Chemical Formula 6A, and

* indicates a linking point that is linked to Chemical Formula 1.

The cyclic group represented by Chemical Formula 6A may be a cyclic group represented by Chemical Formula 6A-3 when $R^{12}$ and $R^{13}$ and/or $R^{14}$ and $R^{15}$ are independently linked to form a fused aromatic ring.

[Chemical Formula 6A-3]

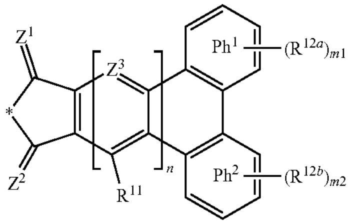

In Chemical Formula 6A-3, $Z^1$, $Z^2$, $Z^3$, $R^{11}$, and n are the same as $Z^1$, $Z^2$, $Z^3$, $R^{11}$, and n, respectively, in Chemical Formula 6A, $R^{12a}$ and $R^{12b}$ may each independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, m1 and m2 are independently an integer of 0 to 4 (e.g., one of 0, 1, 2, 3, or 4),

* indicates a linking point that is linked to Chemical Formula 1, and

Ph1 and Ph2 refer to fused phenylene rings and one of Ph1 or Ph2 may be optionally omitted.

The cyclic group represented by Chemical Formula 6B may be, for example, a cyclic group represented by Chemical Formula 6B-1, Chemical Formula 6B-2, or Chemical Formula 6B-3.

[Chemical Formula 6B-1]

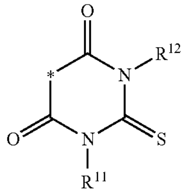

[Chemical Formula 6B-2]

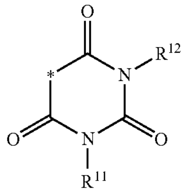

[Chemical Formula 6B-3]

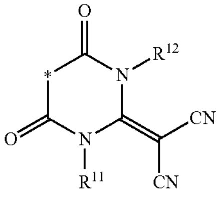

In Chemical Formulas 6B-1, 6B-2, and 6B-3, $R^{11}$ and $R^{12}$ are the same as $R^{11}$ and $R^{12}$, respectively, in Chemical Formula 6B, and * indicates a linking point that is linked to Chemical Formula 1.

The cyclic group represented by Chemical Formula 6C may be, for example, a cyclic group represented by Chemical Formula 6C-1 or Chemical Formula 6C-2.

[Chemical Formula 6C-1]

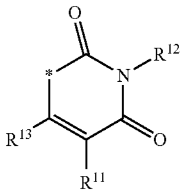

[Chemical Formula 6C-2]

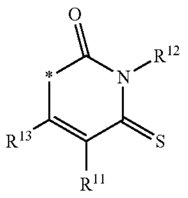

In Chemical Formulas 6C-1 and 6C-2, $R^{11}$ to $R^{13}$ are the same as $R^{11}$ to $R^{13}$, respectively, in Chemical Formula 6C, and * indicates a linking point that is linked to Chemical Formula 1.

Specific examples of the compound of Chemical Formula 1 may include one of the compounds of Group 1, but is not limited thereto.

[Group 1]
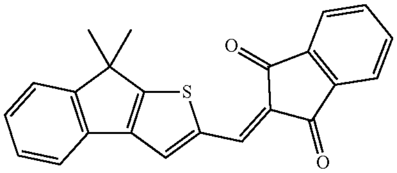
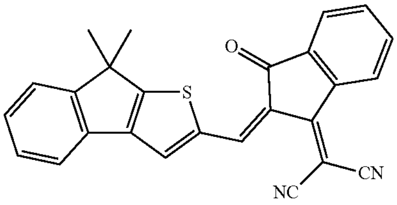
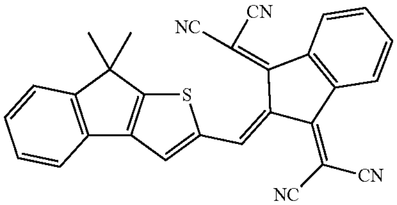
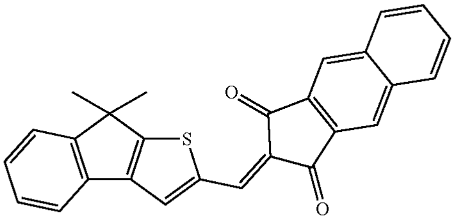
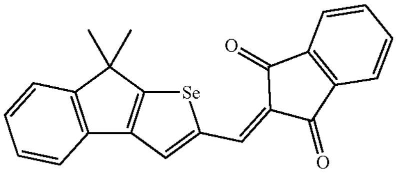
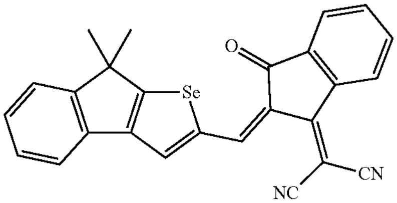
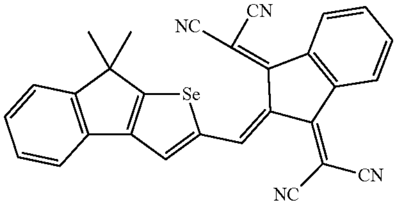
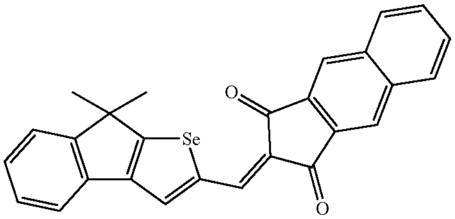
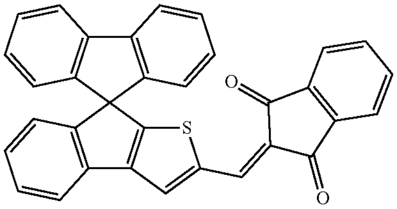
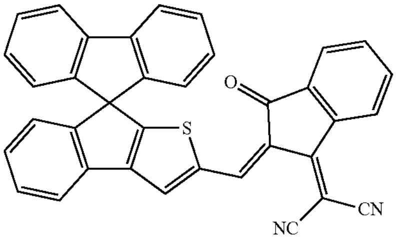
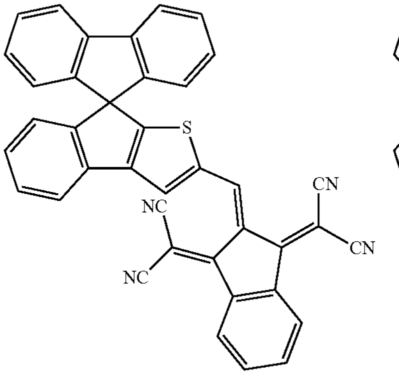
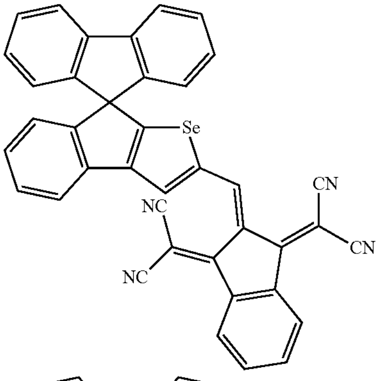
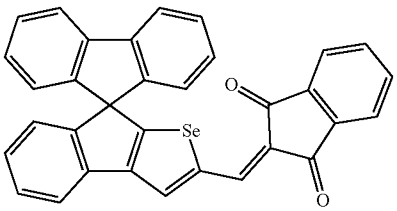
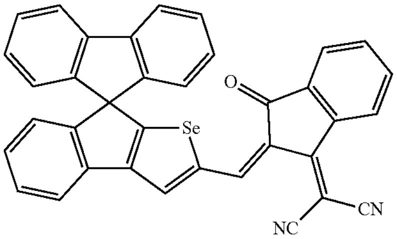

-continued
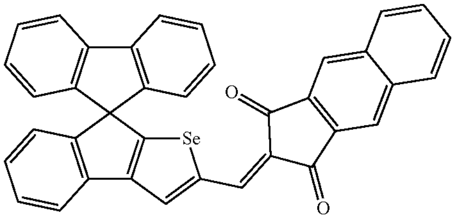
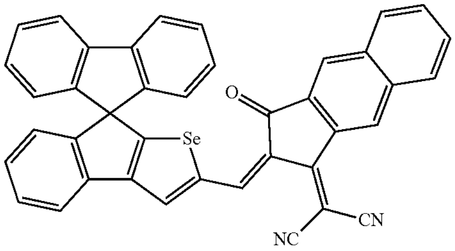
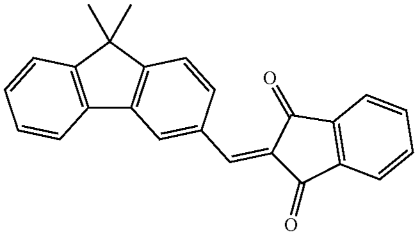
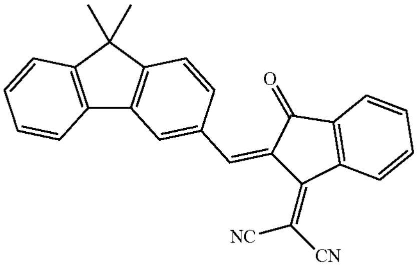
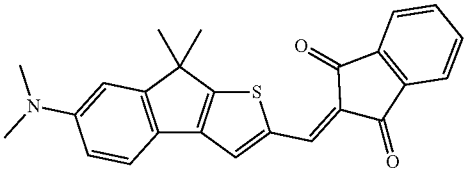
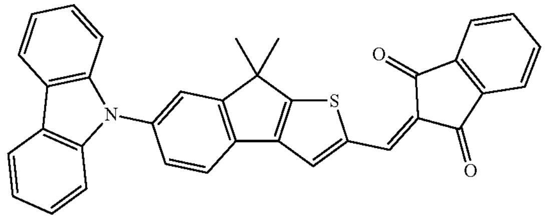
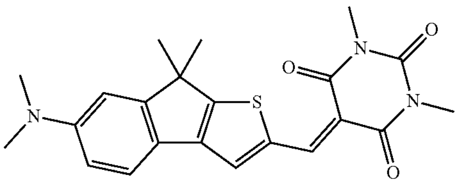
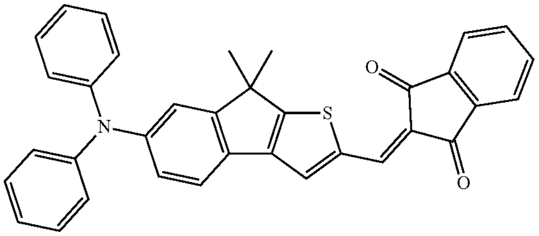
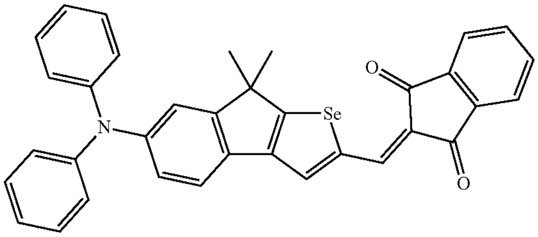
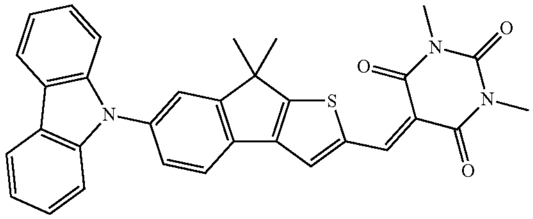
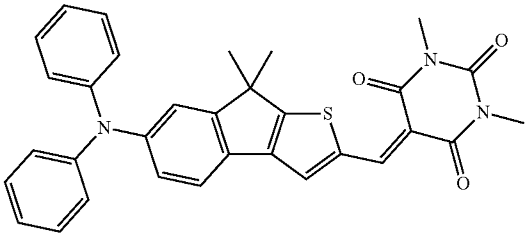
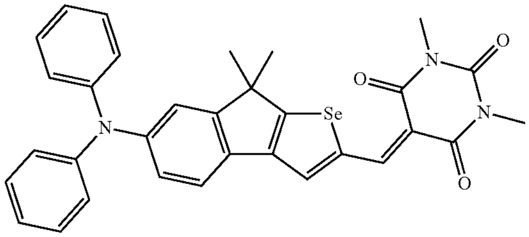
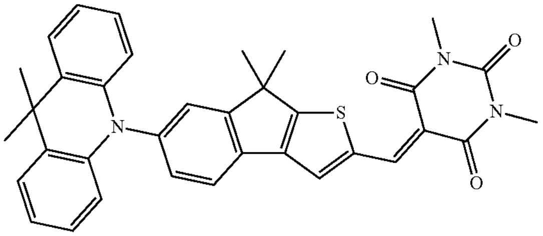

-continued
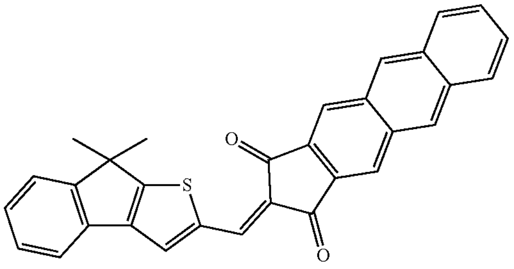
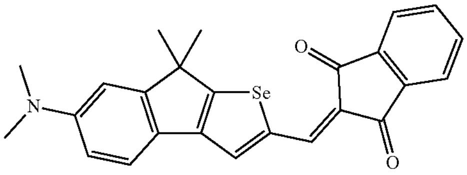
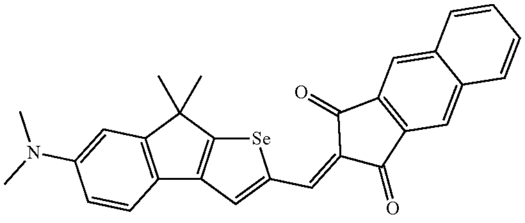
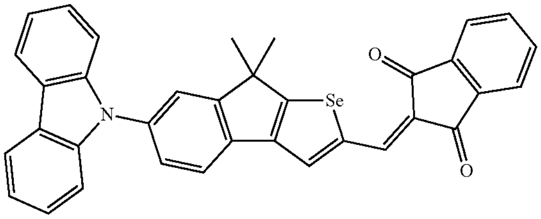
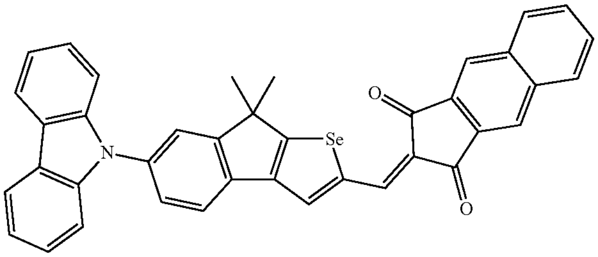
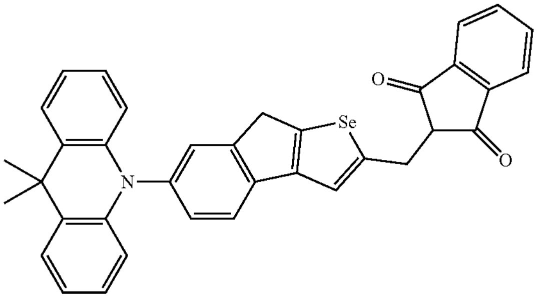
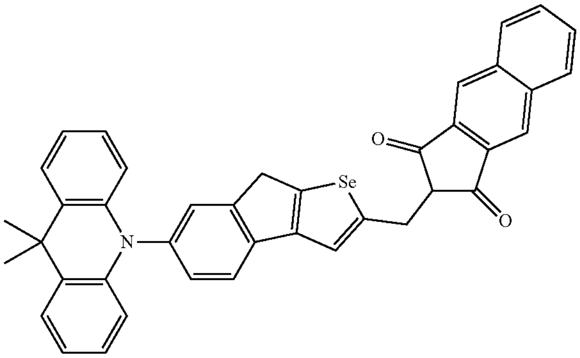
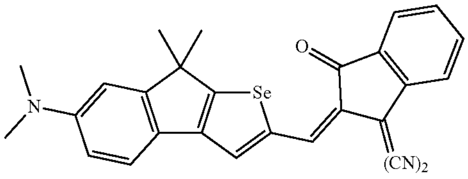
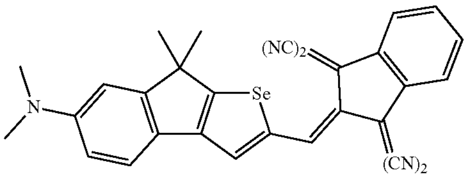
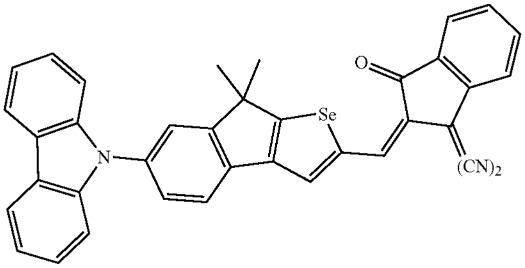
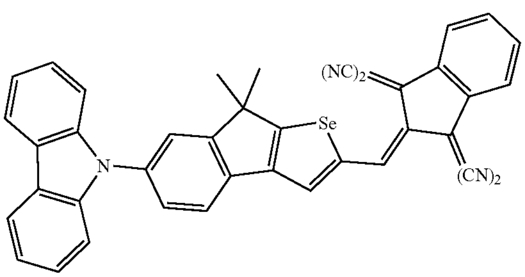
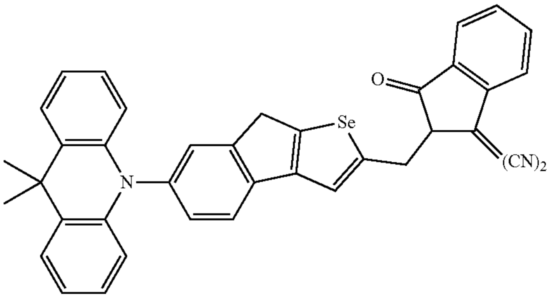

-continued
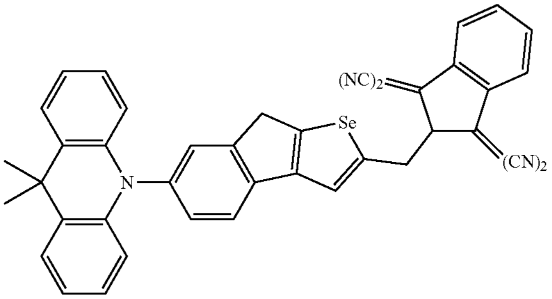
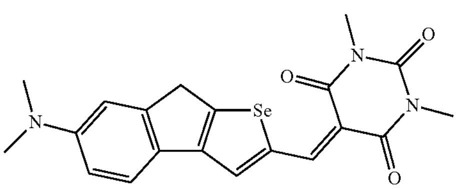
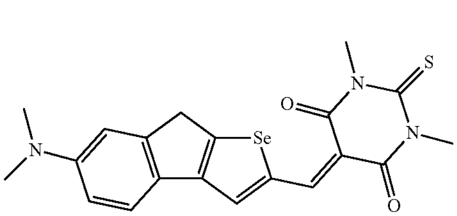
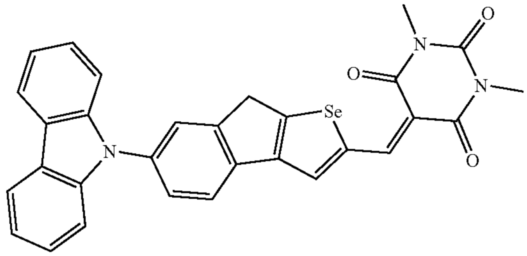
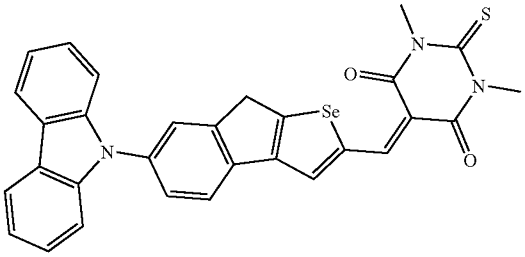
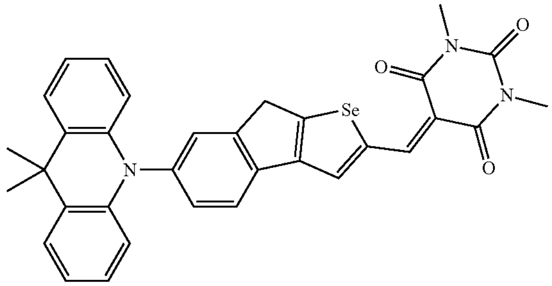
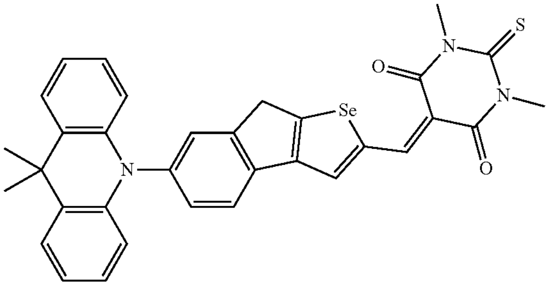
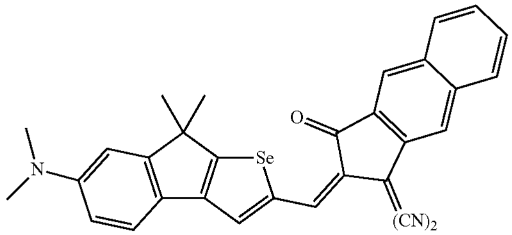
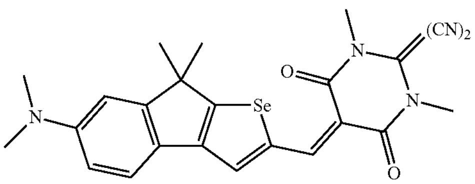
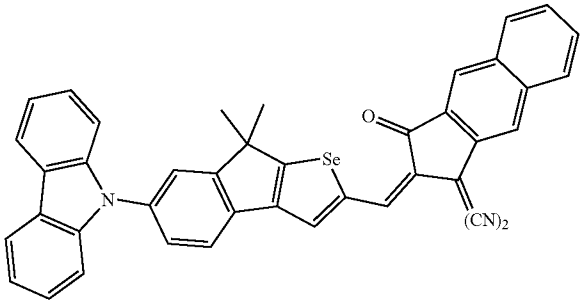

-continued

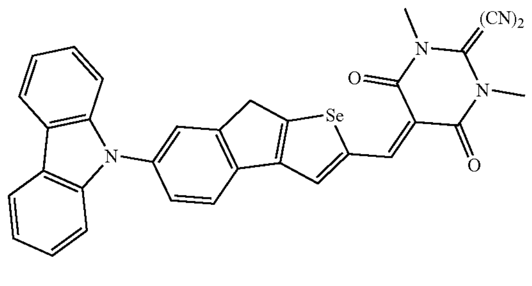

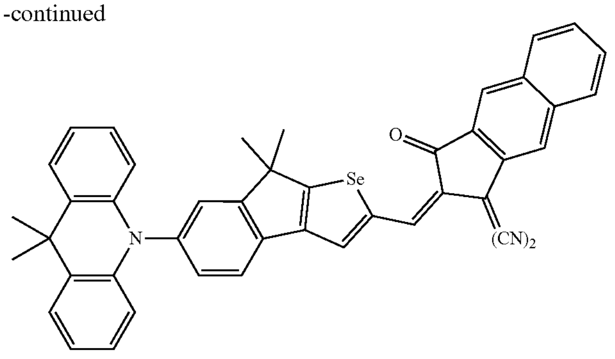

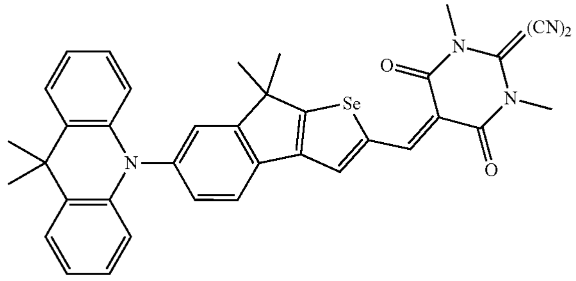

In Group 1, at least one hydrogen of each ring may be not replaced (e.g., may be present) or may be replaced by a substituent of a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, or any combination thereof.

In Group 1, the compounds in which $X^1$ may be S or Se are shown, but compounds in which $X^1$ may be O, Te, S(═O), S(═O)$_2$, Si$R^aR^b$, Ge$R^cR^d$, or C$R^eR^f$, wherein $R^a$, $R^b$, $R^c$, $R^d$, $R^e$, and $R^f$ are each independently hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ are each independently present or at least one pair of $R^a$ and $R^b$, $R^c$ and $R^d$, or $R^e$ and $R^f$ is linked to each other to provide a separate spiro structure, may also be shown in the same manner.

Also, in Group 1, the compounds in which $Ar^2$ is a cyclic group represented by Chemical Formula 6A or a cyclic group represented by Chemical Formula 6B are shown, but compounds in which $Ar^2$ is a cyclic group represented by Chemical Formula 6C to Chemical Formula 6G may also be shown in the same manner.

The compound represented by Chemical Formula 1 is a compound that selectively absorbs light in a green wavelength region, and may have a maximum absorption wavelength (Amax) in a wavelength range of greater than or equal to about 500 nm and less than or equal to about 600 nm, for example, greater than or equal to about 510 nm and less than or equal to about 580 nm, or greater than or equal to about 520 nm and less than or equal to about 555 nm in a thin film state.

The compound represented by Chemical Formula 1 has an absorption curve having a full width at half maximum (FWHM) of about 50 nm to about 150 nm, for example about 50 nm to about 120 nm, or about 50 nm to about 100 nm in a thin film state. By having the full width at half maximum in the above range, selectivity for the whole green wavelength region may be increased. The thin film may be a thin film deposited under vacuum conditions.

In some example embodiments, the sublimation temperature (temperature obtained by vacuum deposition, also referred to as "deposition temperature") of the compound represented by Chemical Formula 1 may be less than or equal to about 390° C., for example, about 100° C. to about 390° C. Due to the sublimation temperature in the above range, there is little possibility of impurity mixing when forming a thin film by deposition. The sublimation temperature may be confirmed by thermogravimetric analysis (TGA), and may be, for example, a temperature at which a weight loss of 10% relative to an initial weight occurs during thermogravimetric analysis at a pressure of 10 Pa or less.

In addition, a micro lens array (MLA) needs to be formed to concentrate light after manufacturing an organic photoelectric device during manufacture of an image sensor. Formation of this micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal vibration due to a heat treatment, but a material having a firm molecule structure may not have the thermal vibration and be prevented from the deterioration by the heat treatment. The compound represented by Chemical Formula 1 has a conjugated structure in the donor moiety and thus may be stably maintained during the MLA heat treatment and secure process stability.

The compound represented by Chemical Formula 1 may be an n-type semiconductor or a p-type semiconductor. A compound having a relatively shallower LUMO energy level and/or relatively shallower HOMO energy level may be used as the p-type semiconductor. The compound may have a HOMO energy level in the range of about 4.5 eV to about 6.5 eV and an energy bandgap of greater than or equal to about 2.0 eV, for example, about 2.0 eV to about 3.0 eV. In this case, the LUMO energy level is located between about 2.5 eV and about 4.5 eV. By adjusting the HOMO and LUMO energy levels of the compound used in combination with the compound of Chemical Formula 1, the compound of Chemical Formula 1 may be used as an n-type semiconductor or a p-type semiconductor.

For example, when the compound represented by Chemical Formula 1 is an n-type semiconductor (e.g., when a light absorbing layer includes an n-type semiconductor that includes and/or is the compound represented by Chemical Formula 1), the p-type semiconductor (e.g., a p-type semiconductor included in the same light absorbing layer) may include a compound represented by Chemical Formula 7. The composition including the n-type semiconductor including the compound represented by Chemical Formula 1 and the p-type semiconductor including the compound represented by Chemical Formula 7 has excellent absorption in the whole green wavelength region, so that the photoelectric device and the light absorption sensor including the same may exhibited improved photoelectric conversion efficiency and decreased dark current.

[Chemical Formula 7]

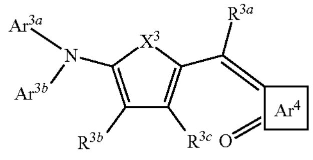

In Chemical Formula 7, $X^3$ may be O, S, Se, Te, S(=O), S(=O)$_2$, Si$R^aR^b$, Ge$R^cR^d$, or C$R^eR^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, and $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide a spiro structure, $Ar^{3a}$ and $Ar^{3b}$ may each independently be a substituted or unsubstituted C6 to C30 aryl group or a substituted or unsubstituted C3 to C30 heteroaryl group, wherein $Ar^{3a}$ and $Ar^{3b}$ may each independently be present or are linked to each other to provide a fused ring, $Ar^4$ may be a substituted or unsubstituted C6 to C30 arene group, a substituted or unsubstituted C3 to C30 heteroarene group, or a fused ring of two or more thereof, and $R^{3a}$, $R^{3b}$, and $R^{3c}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ may each independently be present or are linked to each other to provide a ring, and $Ar^{3b}$ and $R^{3b}$ may be optionally linked to each other to provide a fused ring.

For example, $Ar^{3a}$ and $Ar^{3b}$ may be linked to each other to provide a fused ring, and in this case, the compound represented by Chemical Formula 7 may further be represented by Chemical Formula 7A.

For example, $Ar^{3b}$ and $R^{3b}$ may be linked to each other to provide a fused ring, and in this case, the compound represented by Chemical Formula 7 may further be represented by Chemical Formula 7B.

[Chemical Formula 7A]

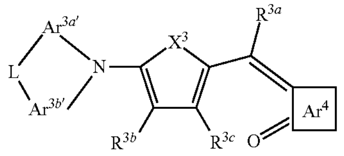

[Chemical Formula 7B]

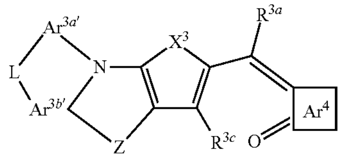

In Chemical Formula 7A and Chemical Formula 7B, $X^3$ may be O, S, Se, Te, S(=O), S(=O)$_2$, Si$R^aR^b$, Ge$R^cR^d$, or C$R^eR^f$, wherein $R^a$, $R^b$, $R^c$, $R^d$, $R^e$, and $R^f$ may each independently be hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ may each independently be present or at least one pair of $R^a$ and $R^b$, $R^c$ and $R^d$, or $R^e$ and $R^f$ may be linked to each other to provide (e.g., establish, define, etc.) a spiro structure (which may be different from any spiro structures included in the compound represented by Chemical Formula 1), $Ar^{3a'}$ and $Ar^{3b'}$ may each independently be a substituted or unsubstituted C6 to C30 arene group or a substituted or unsubstituted C3 to C30 heteroarene group, $Ar^4$ may be a substituted or unsubstituted C6 to C30 arene group, a substituted or unsubstituted C3 to C30 heteroarene group, or a fused ring of two or more thereof, L and Z may each independently be a single bond, O, S, Se, Te, S(=O), S(=O)$_2$, C$R^fR^g$, Si$R^hR^i$, Ge$R^jR^k$, N$R^l$, a substituted or unsubstituted C1 to C30 alkylene group, a substituted or unsubstituted C3 to C30 cycloalkylene group, a substituted or unsubstituted C6 to C30 arylene group, or any combination thereof, wherein $R^f$, $R^g$, $R^h$, $R^i$, $R^j$, $R^k$, and $R^l$ may each independently be hydrogen, deuterium, a substituted or unsubstituted C1 to C20 alkyl group, or a substituted or unsubstituted C6 to C20 aryl group, and $R^{3a}$, $R^{3b}$, and $R^{3c}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ may each independently be present or are linked to each other to provide a ring.

For example, the compound represented by Chemical Formula 7 may be one of compounds in Groups 2A, 2B, or 2C, but is not limited thereto.

[Group 2A]
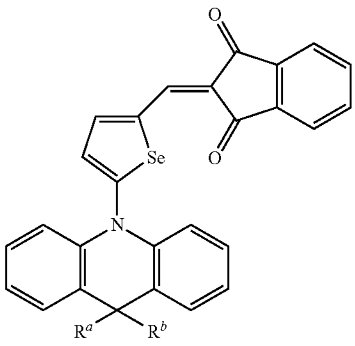
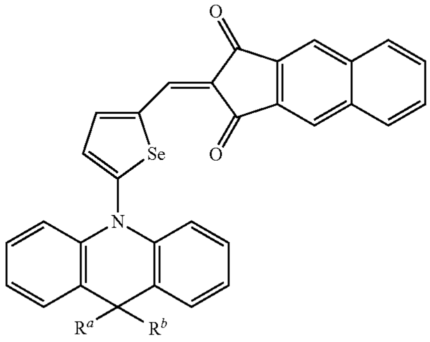
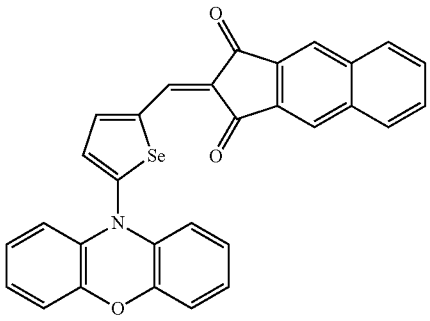
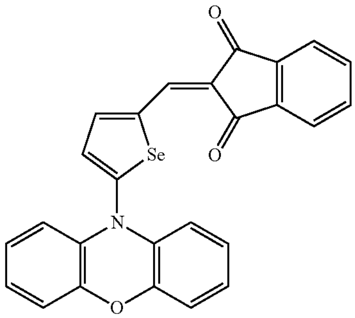
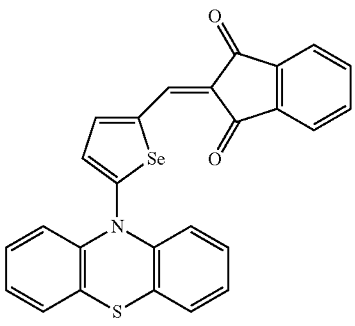
-continued
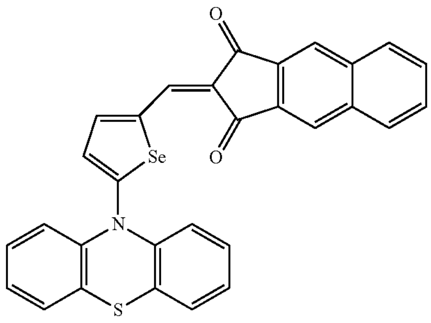
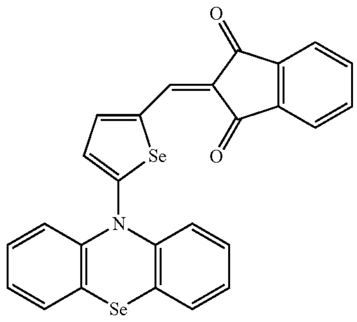
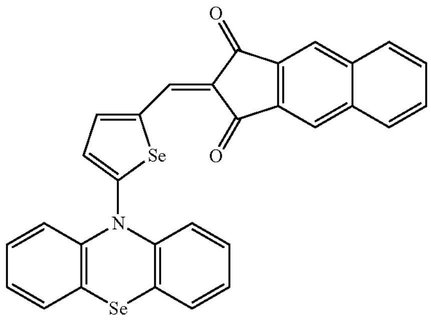
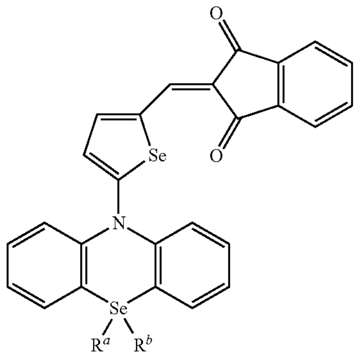
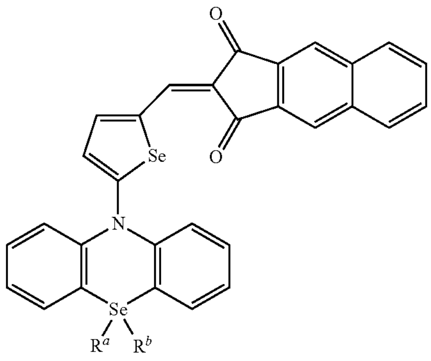

-continued
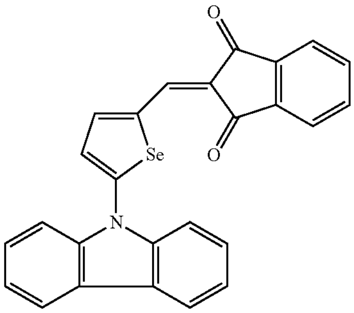
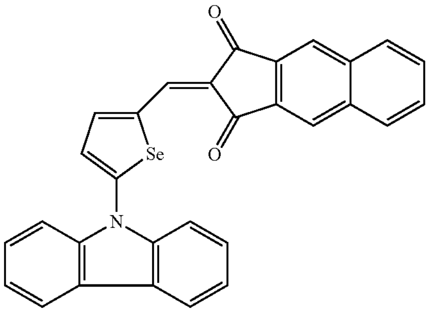
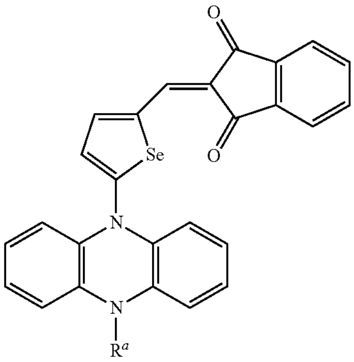
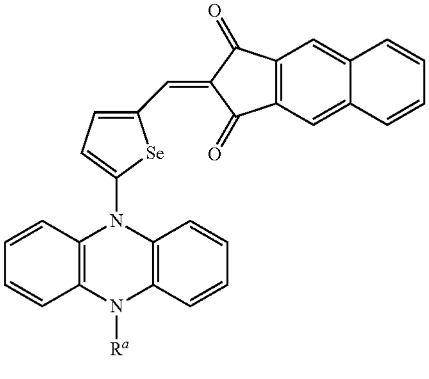
-continued
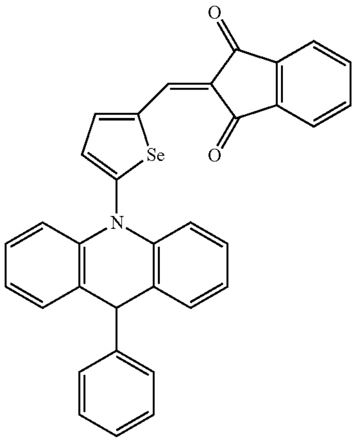
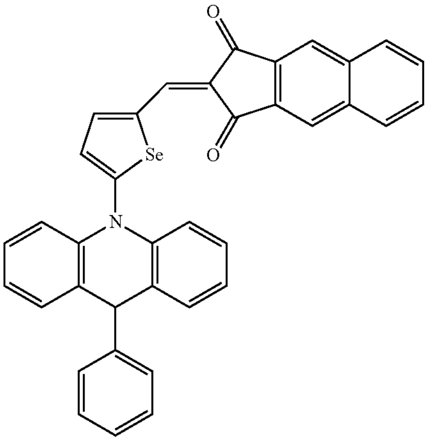
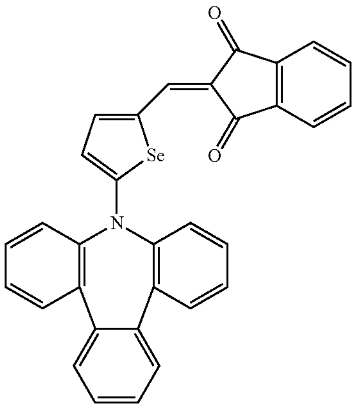
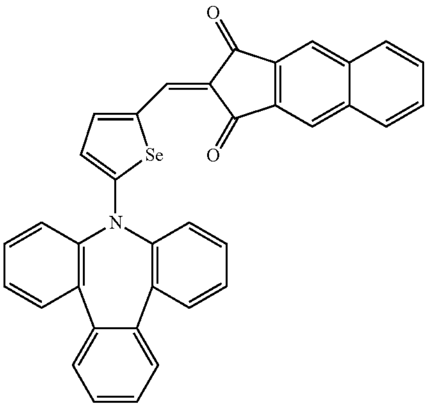

-continued
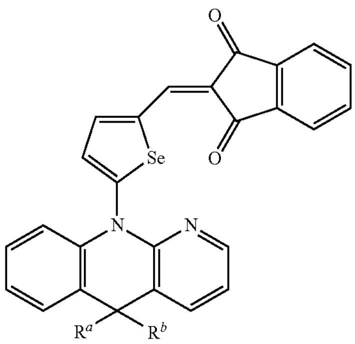
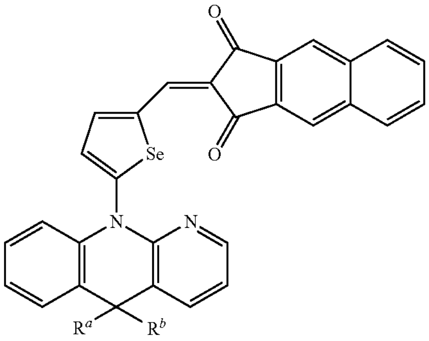
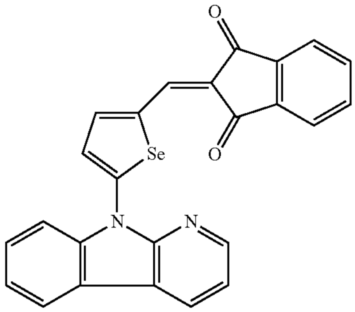
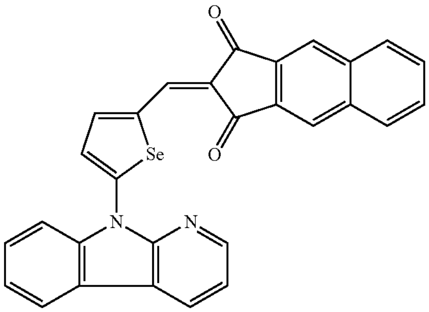
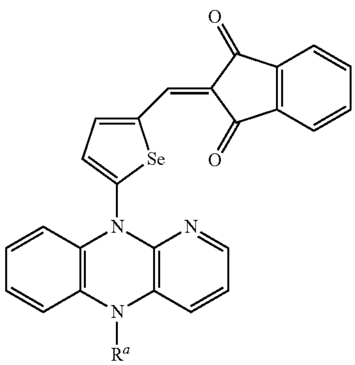
-continued
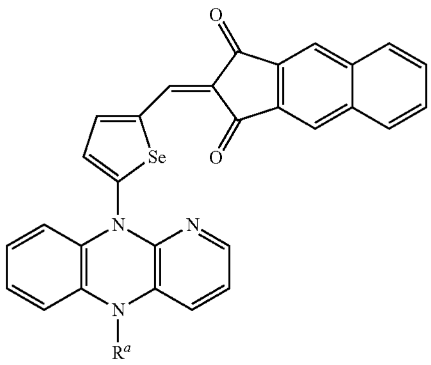
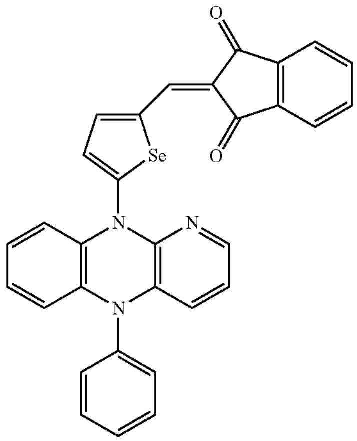
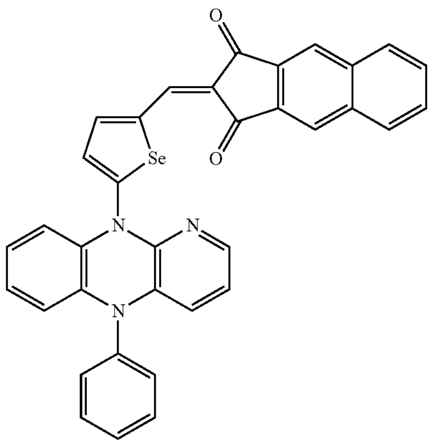
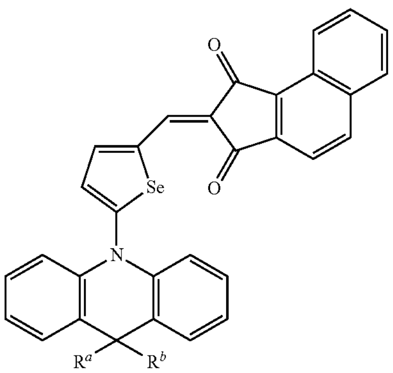

-continued
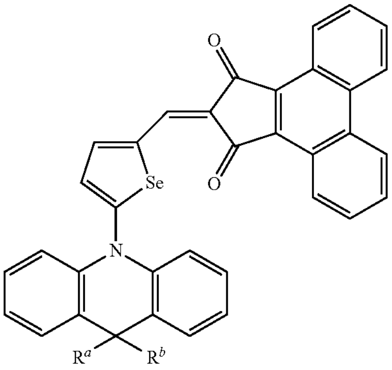
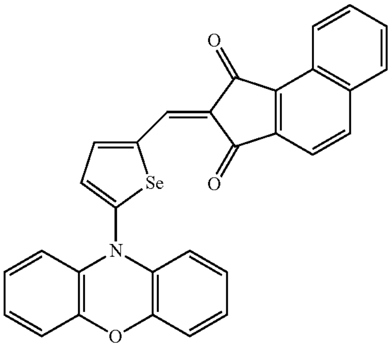
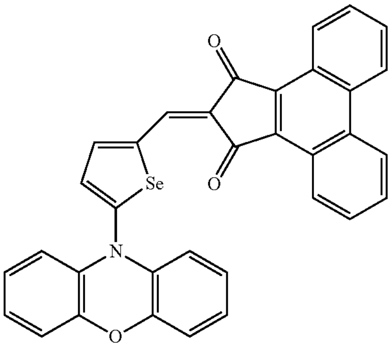
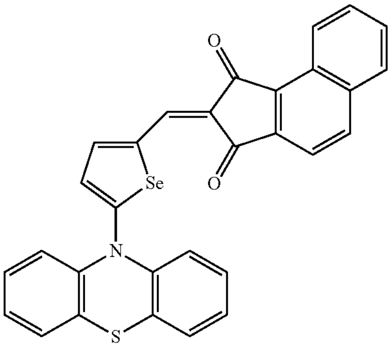
-continued
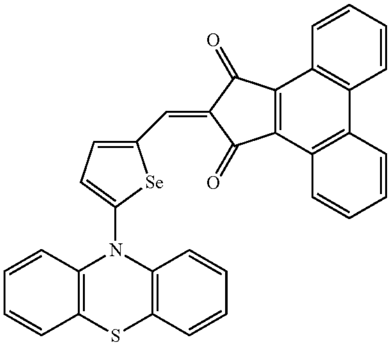
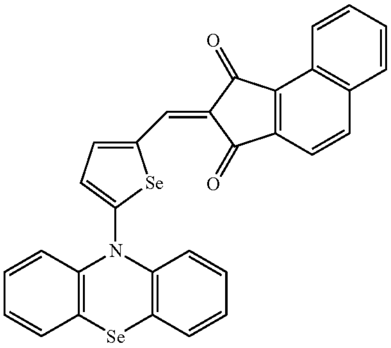
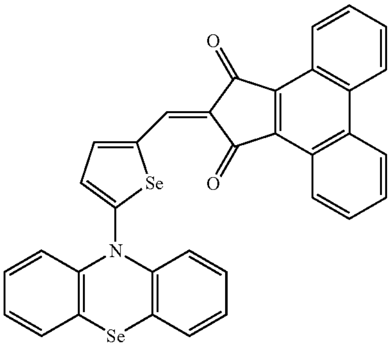
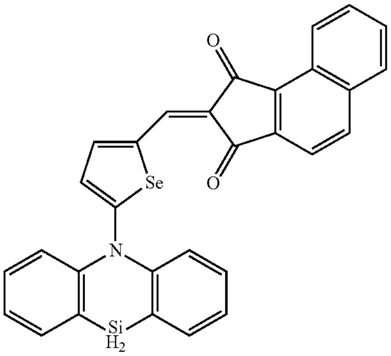

-continued
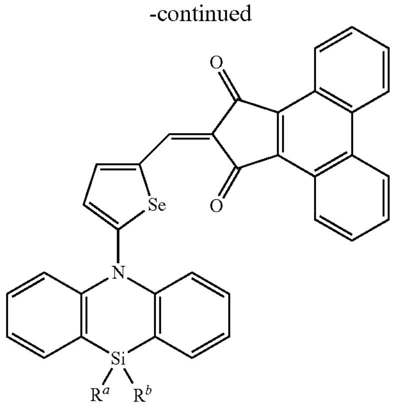
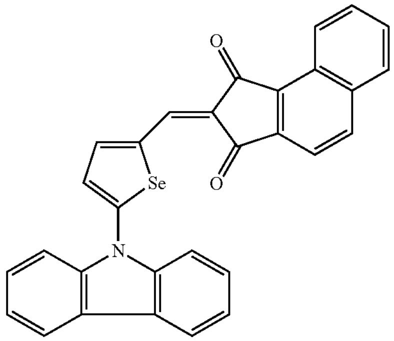
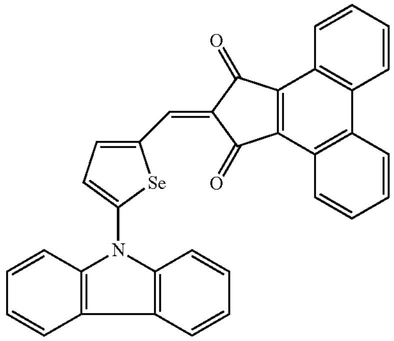
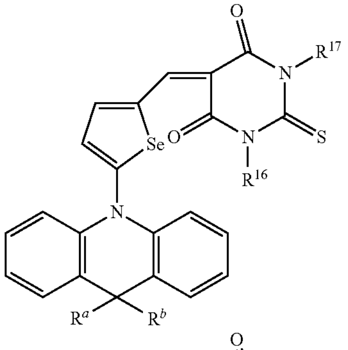
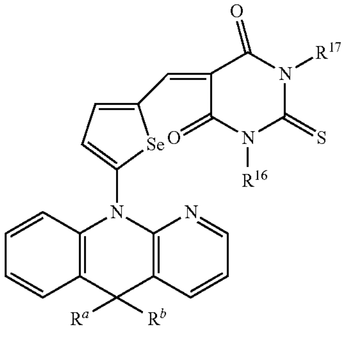
-continued
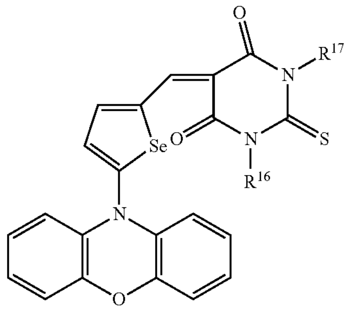
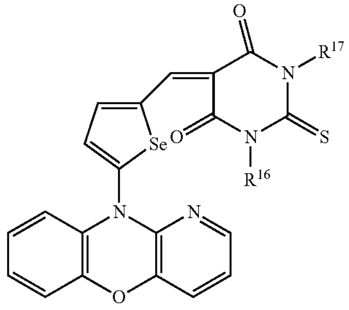
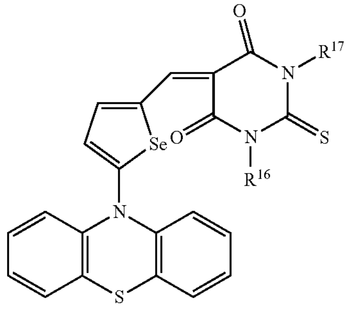
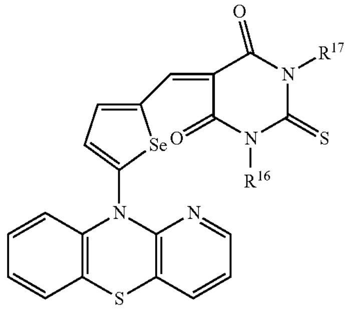
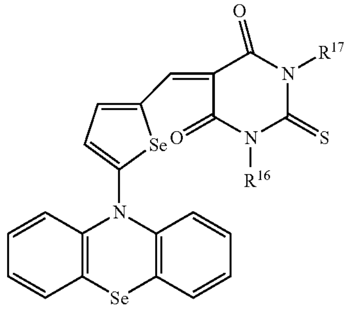

-continued
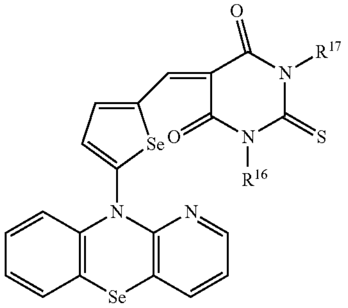
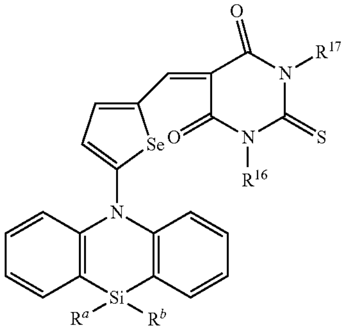
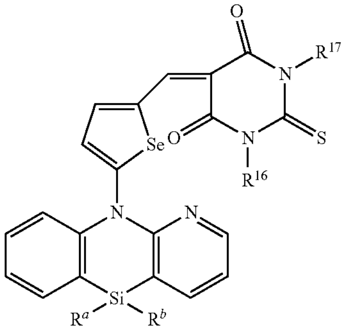
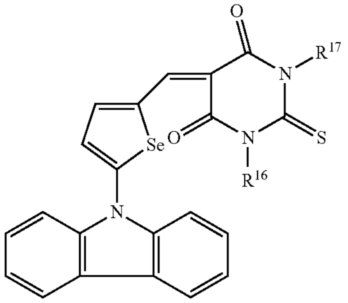
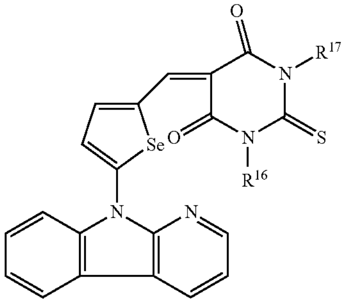
-continued
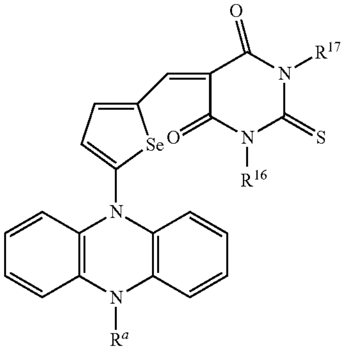
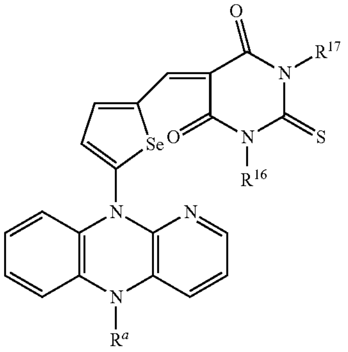
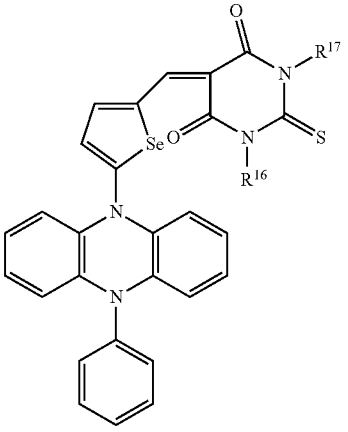
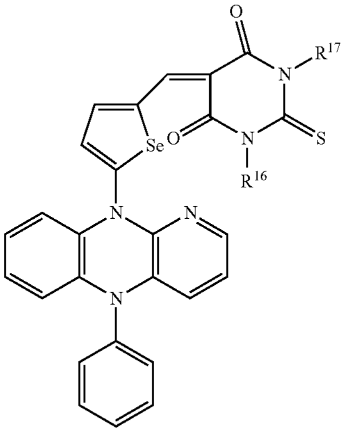

-continued
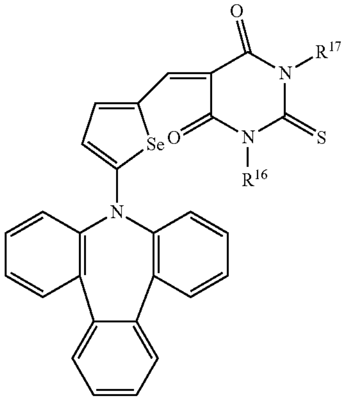
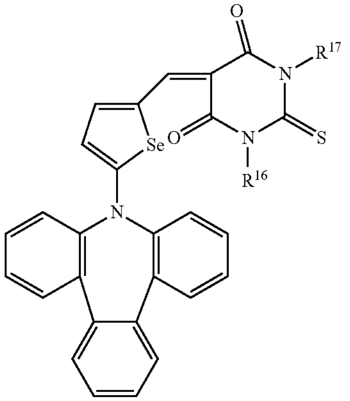
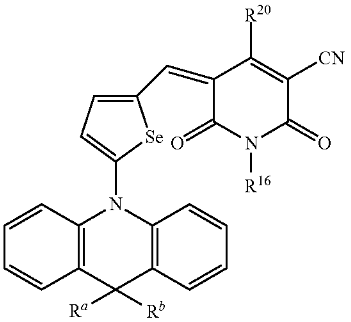
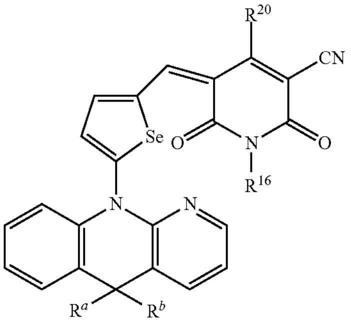
-continued
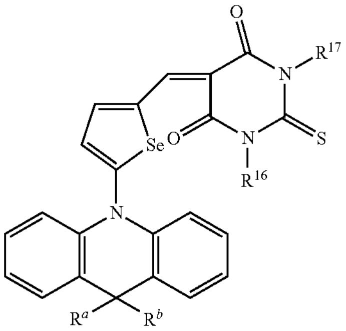
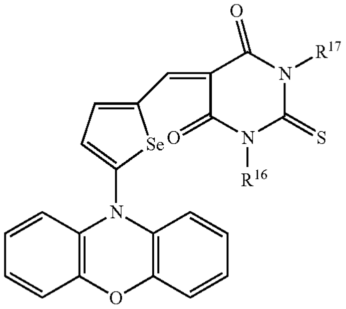
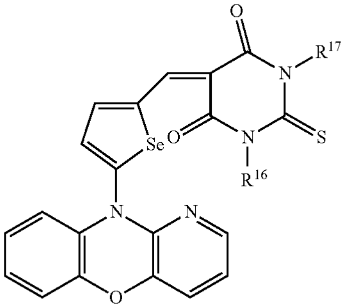
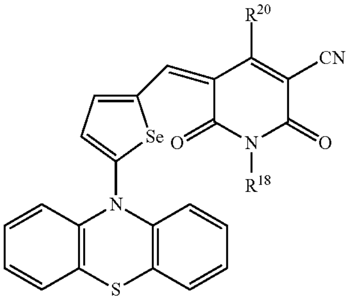
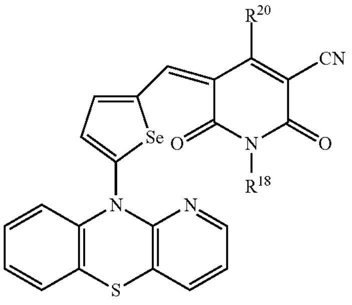

-continued
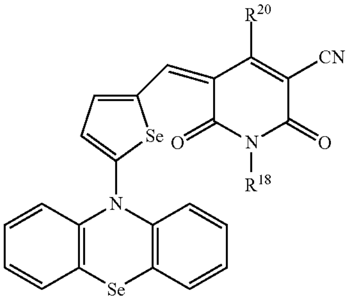
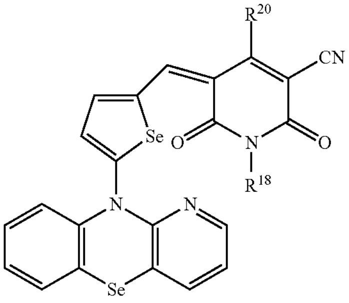
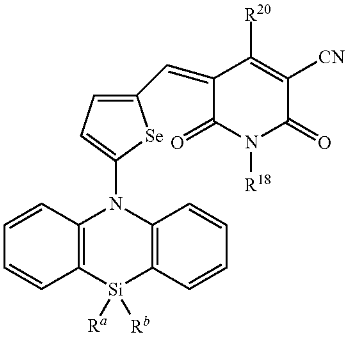
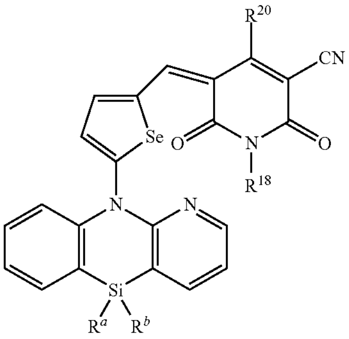
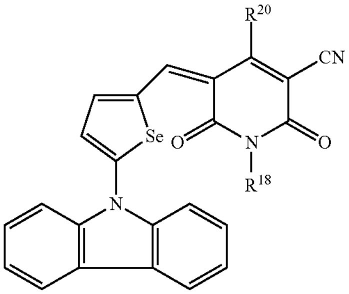
-continued
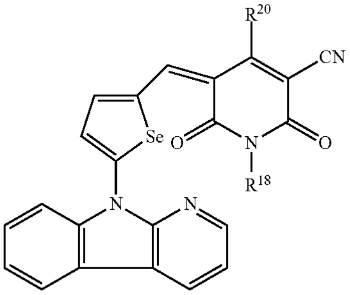
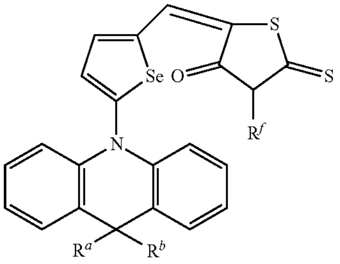
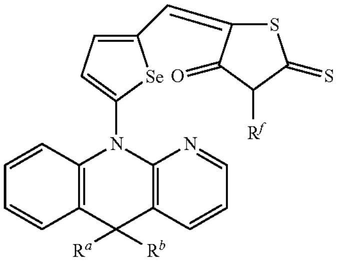
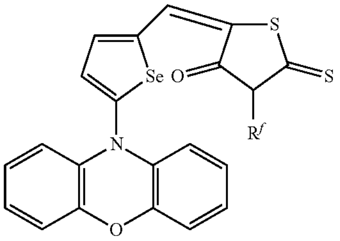
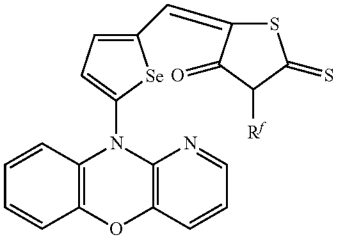
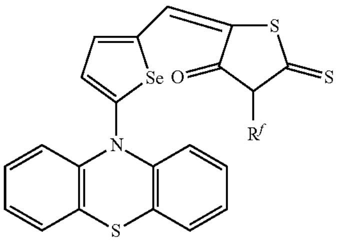

-continued

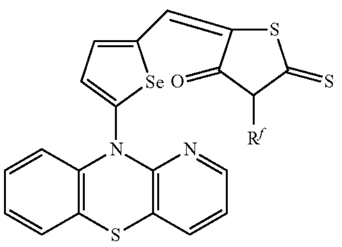

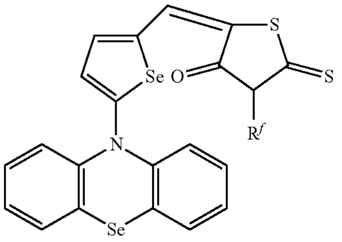

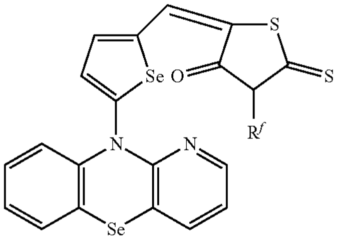

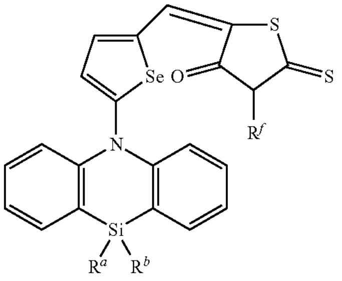

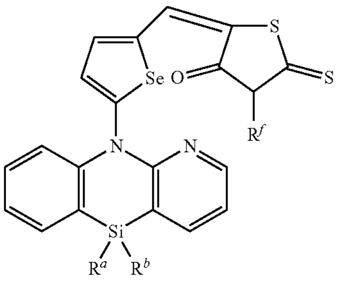

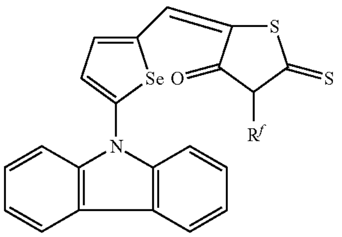

-continued

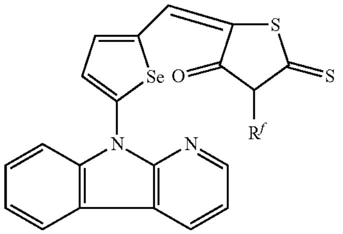

In Group 2A, at least one hydrogen of each aromatic ring or heteroaromatic ring may be present (e.g., may not be replaced) or may be replaced by a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, or any combination thereof, and $R^a$, $R^b$, $R^f$, $R^{16}$, $R^{17}$, $R^{18}$, and $R^{20}$ may each independently be hydrogen or a substituted or unsubstituted C1 to C6 alkyl group.

[Group 2B]

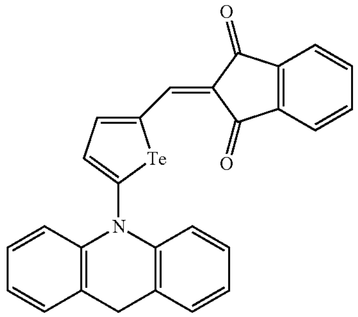

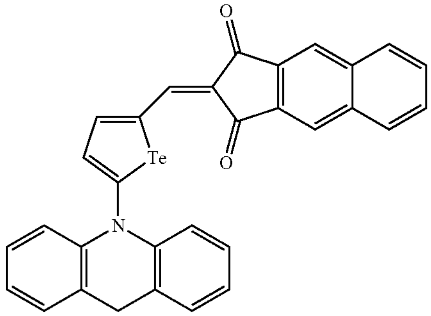

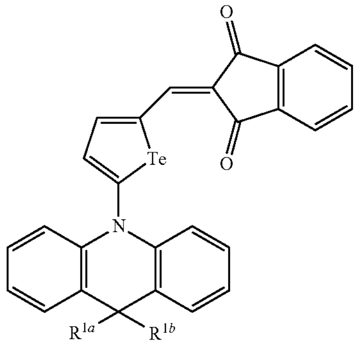

-continued
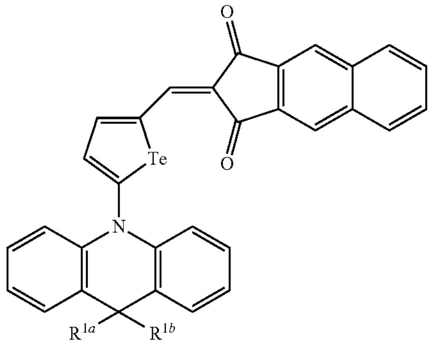
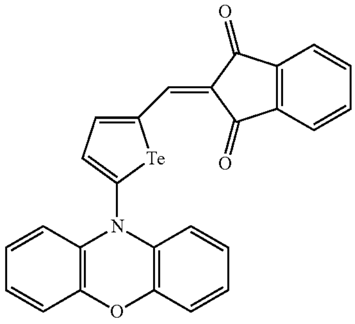
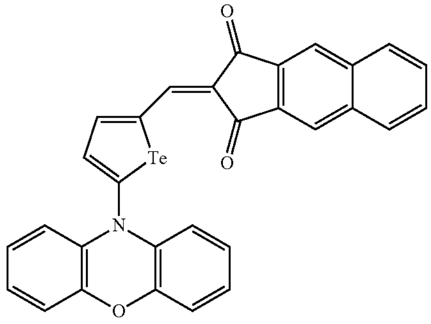
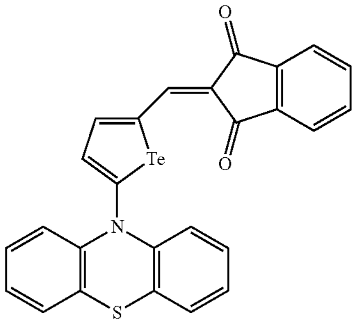
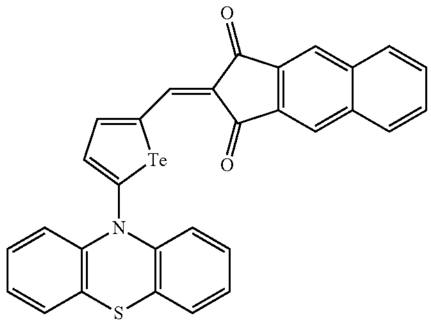
-continued
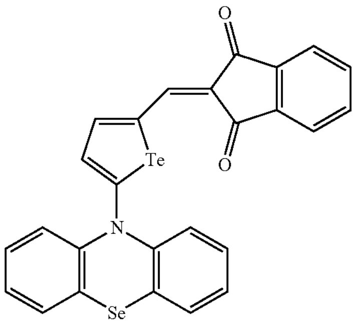
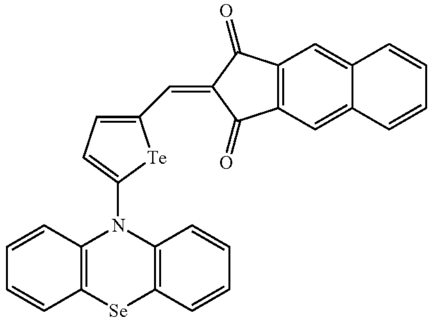
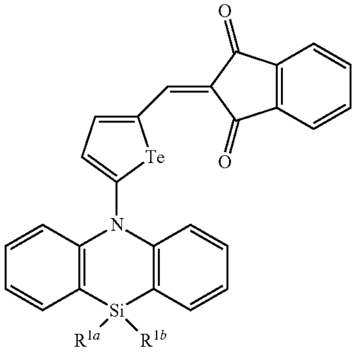
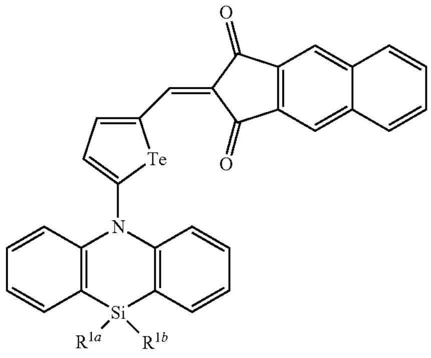
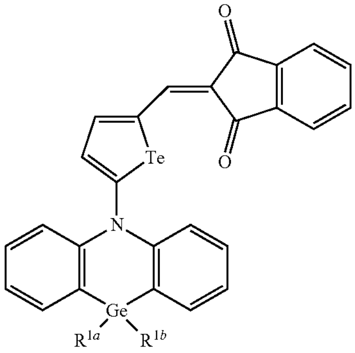

-continued
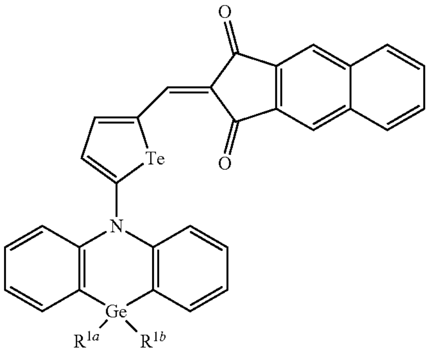
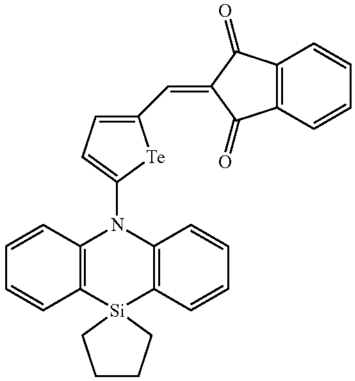
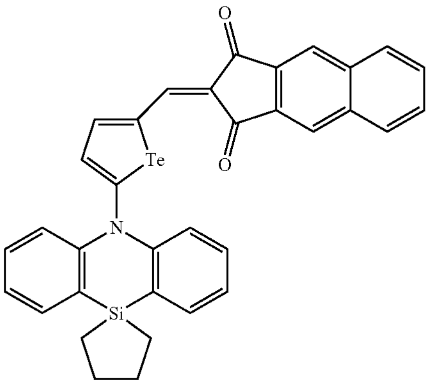
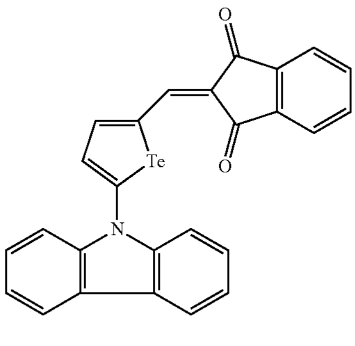
-continued
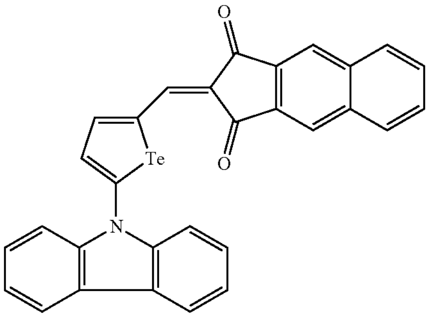
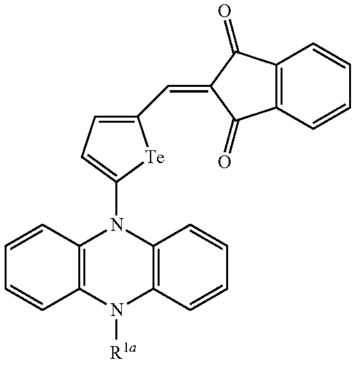
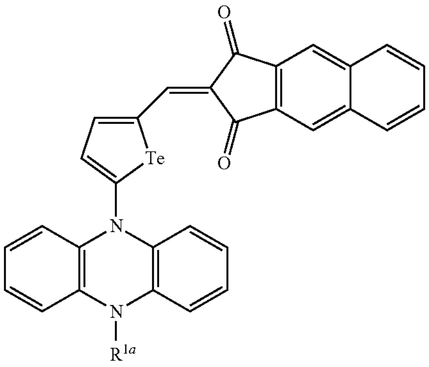
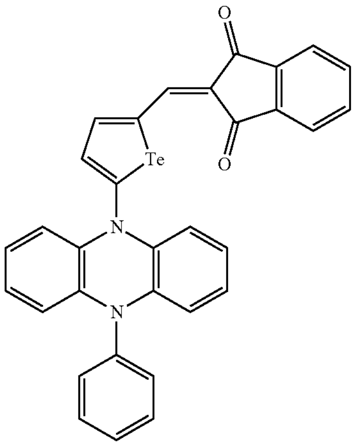

-continued
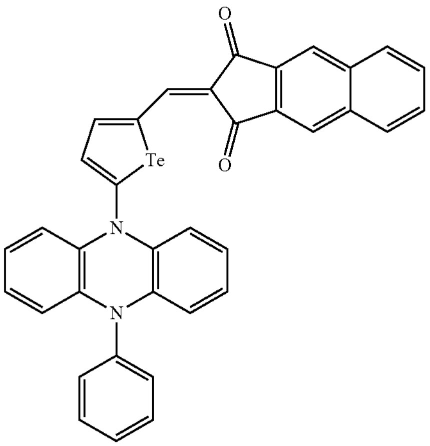
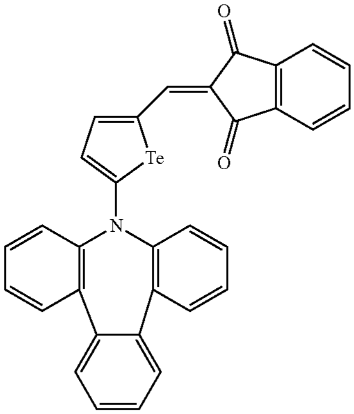
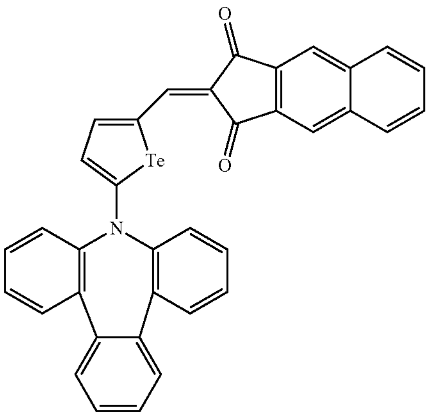
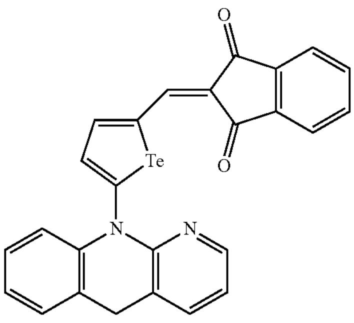
-continued
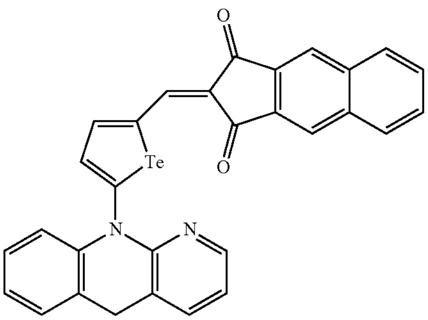
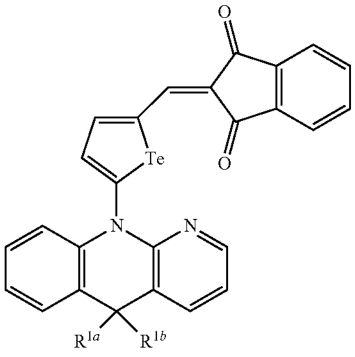
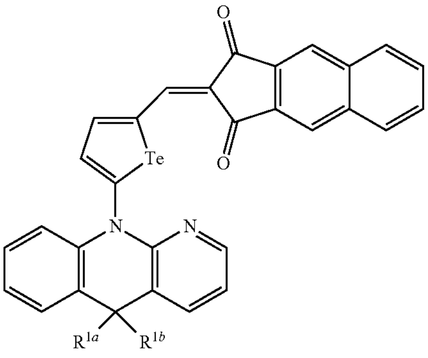
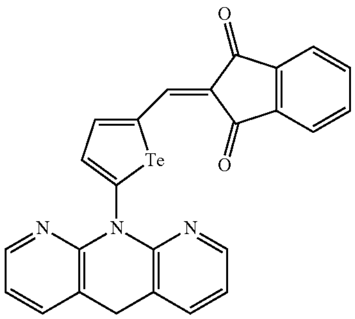
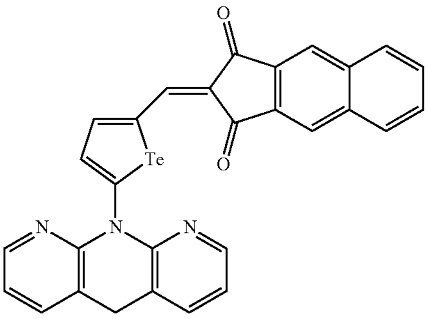

-continued
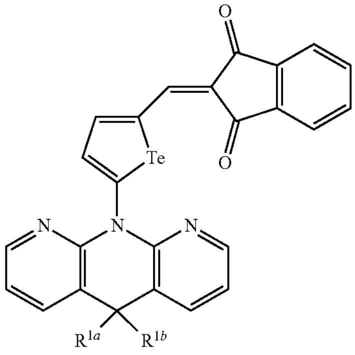
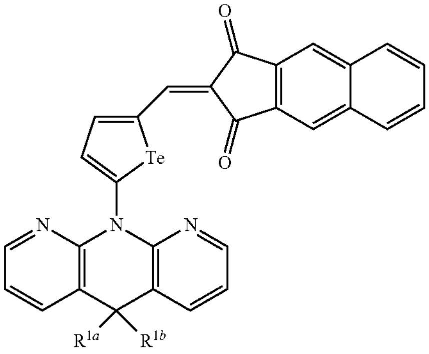
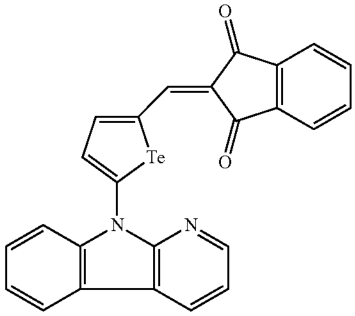
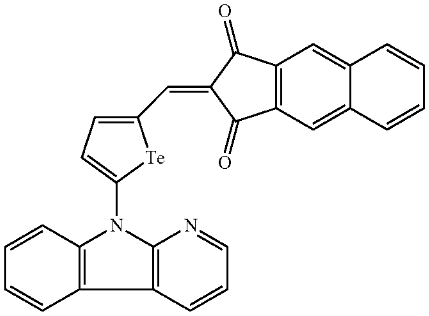
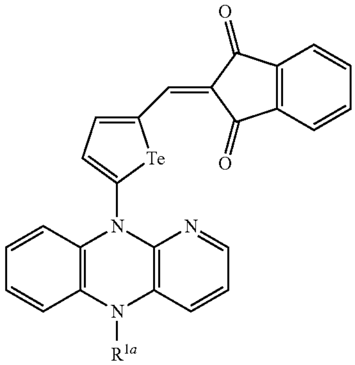
-continued
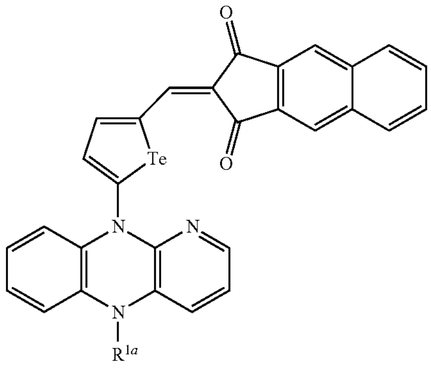
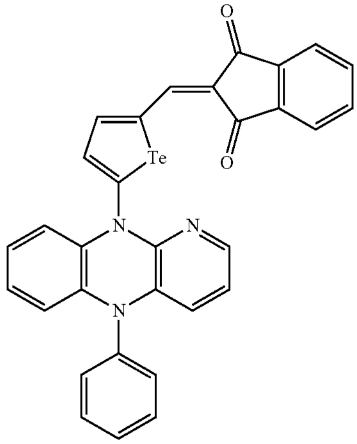
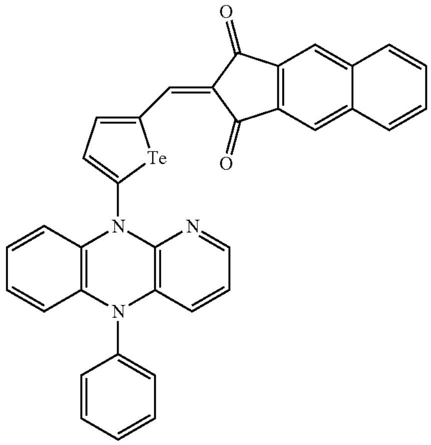
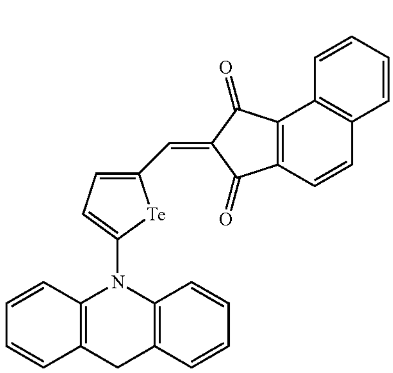

-continued
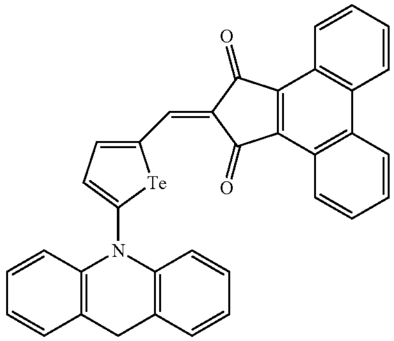
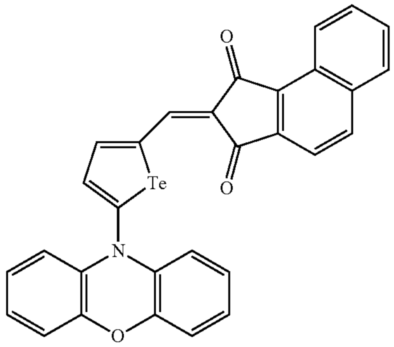
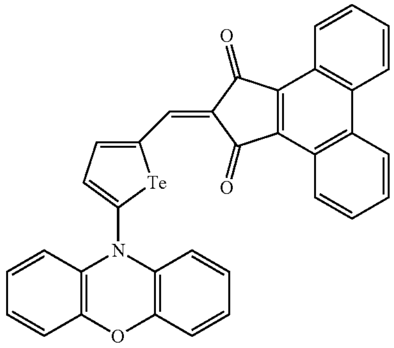
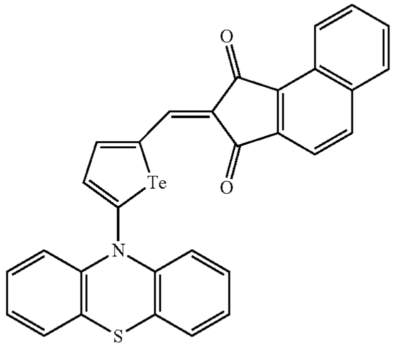
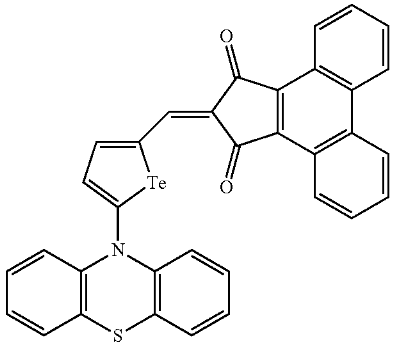
-continued
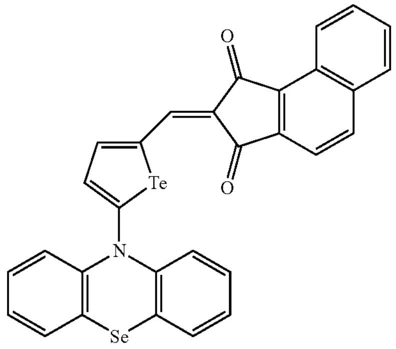
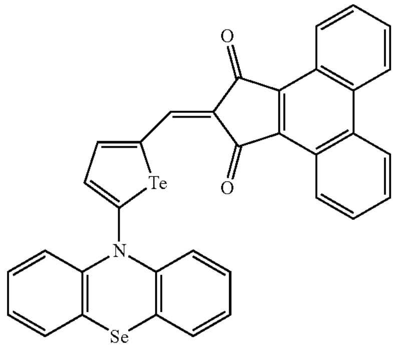
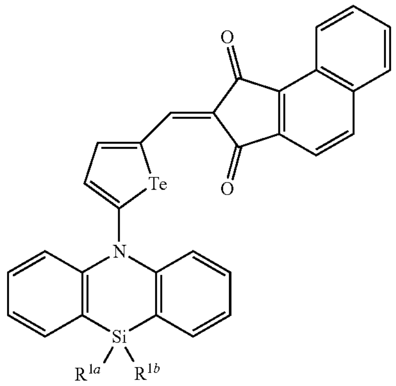
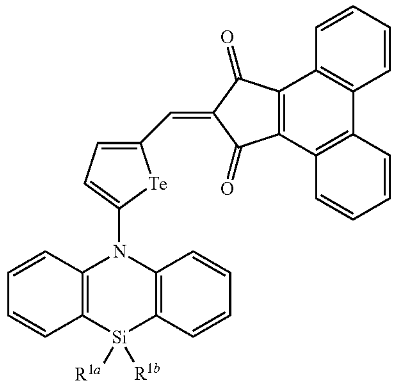

-continued
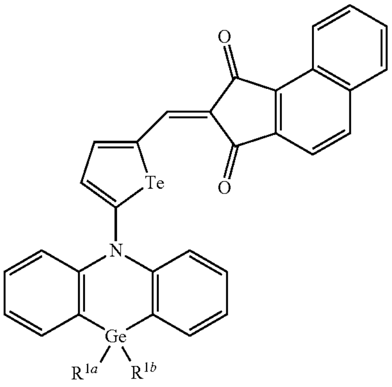
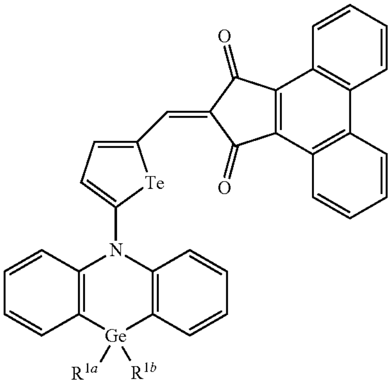
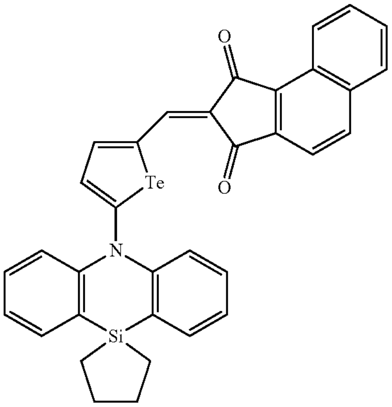
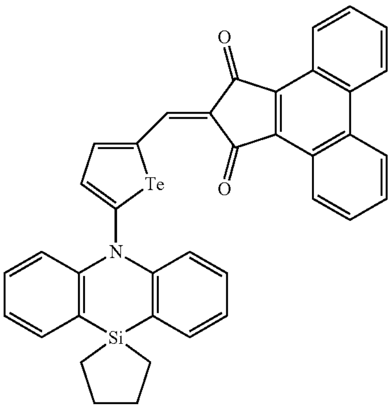
-continued
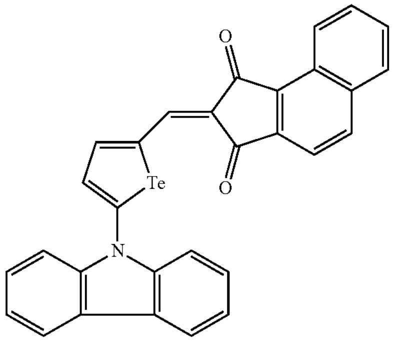
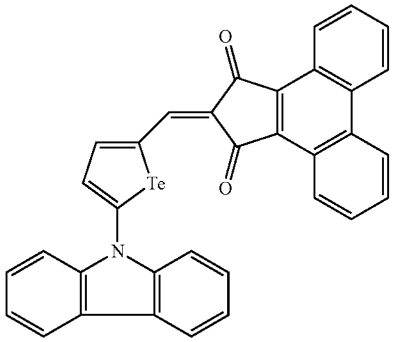
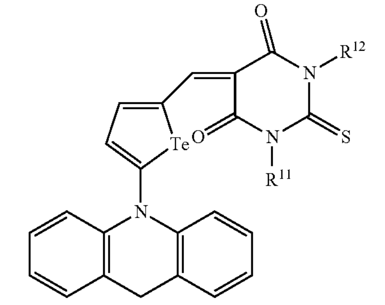
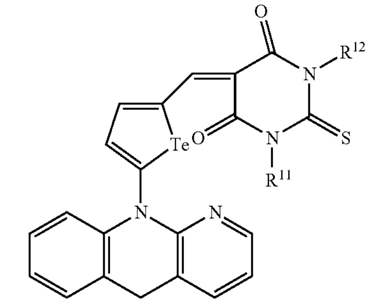
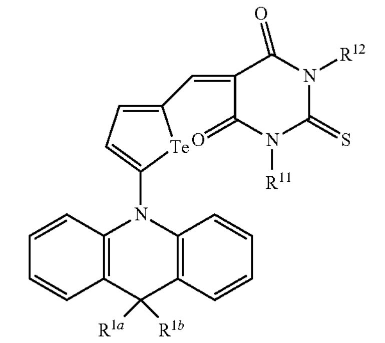

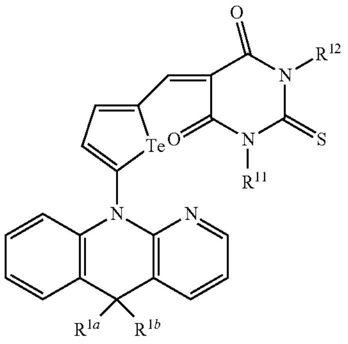
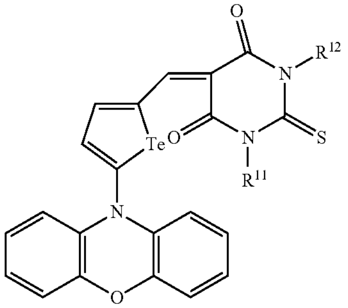
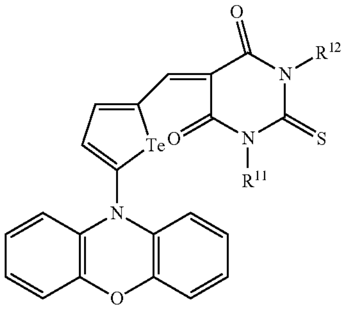
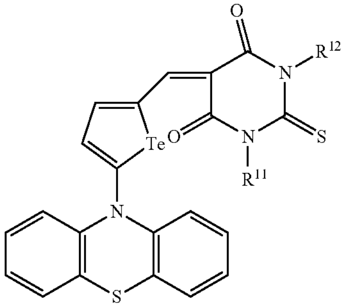
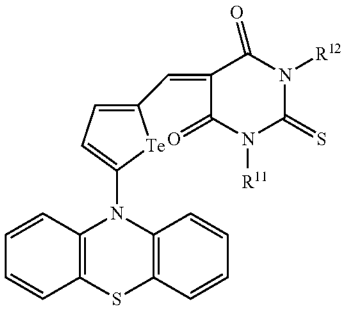
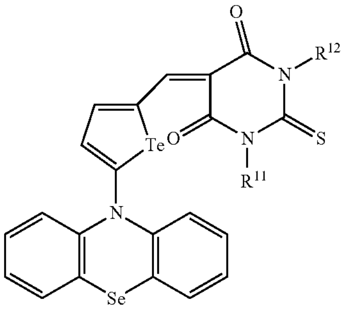
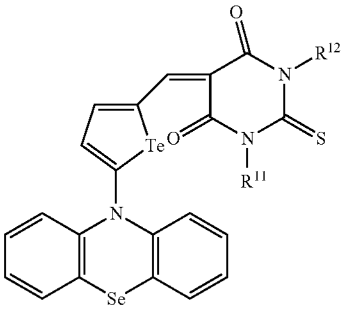
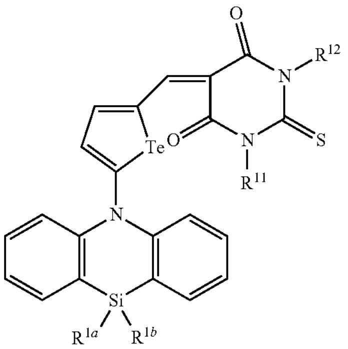
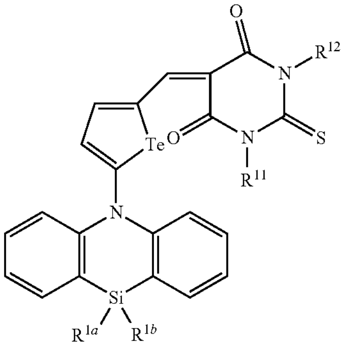
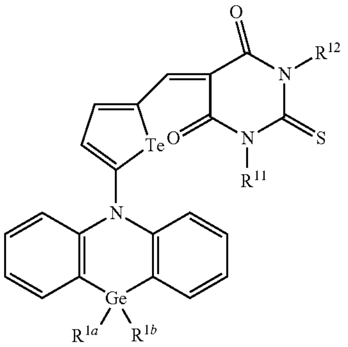

-continued
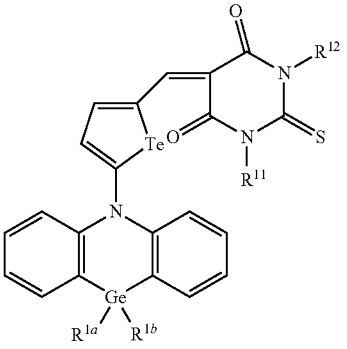
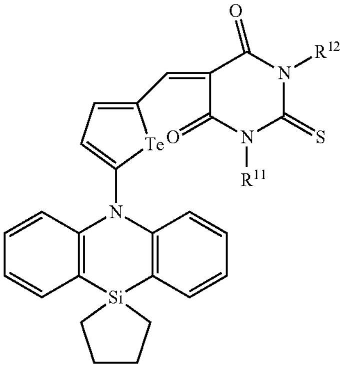
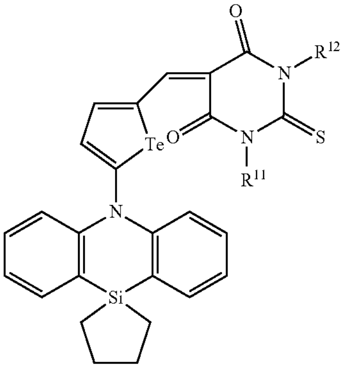
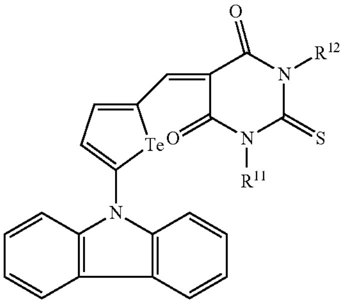
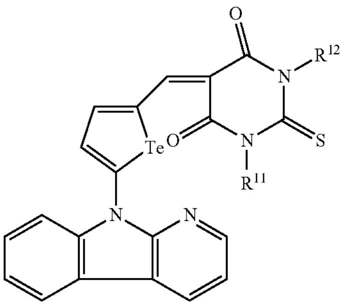
-continued
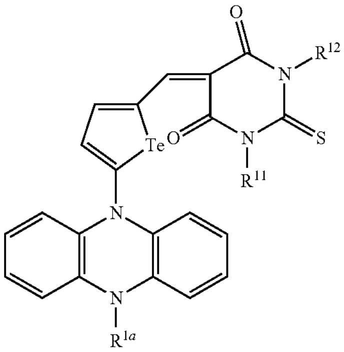
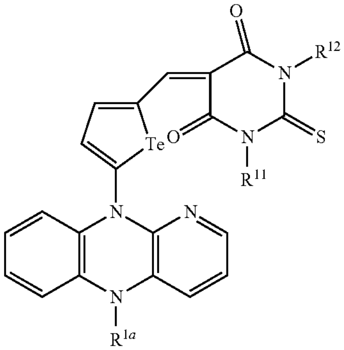
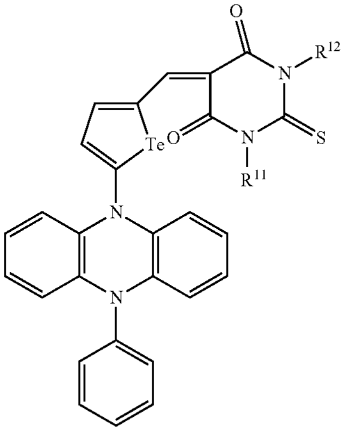
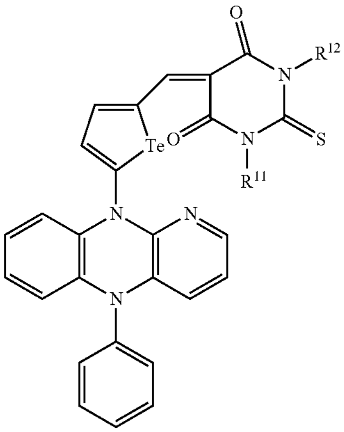

-continued
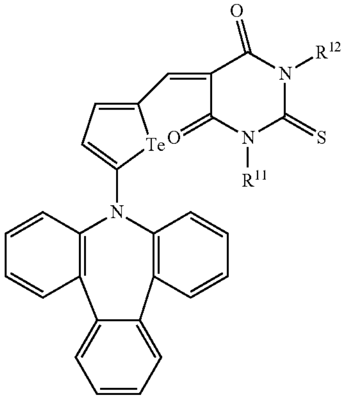
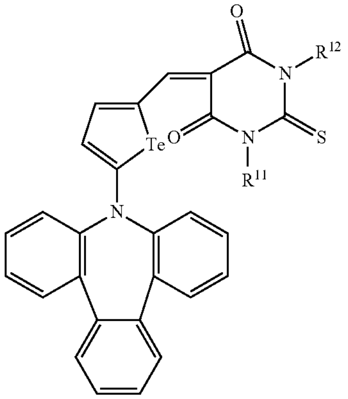
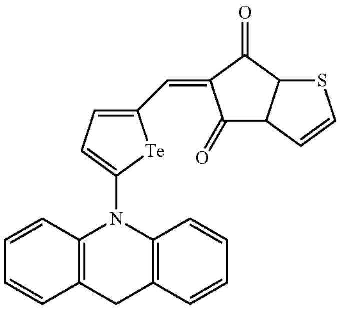
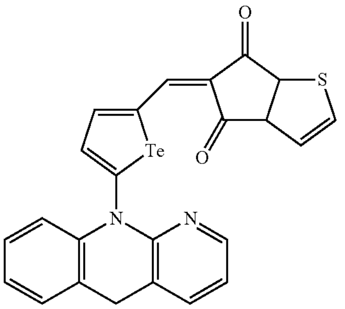
-continued
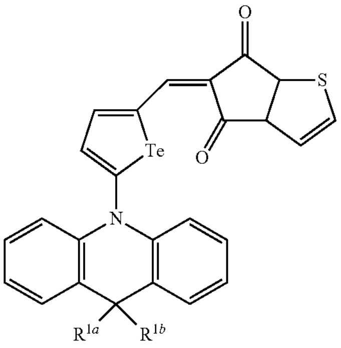
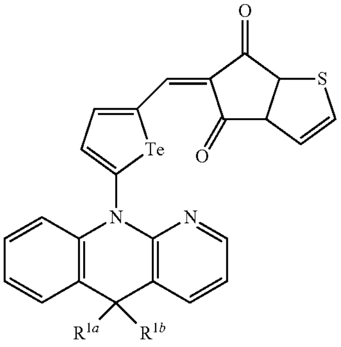
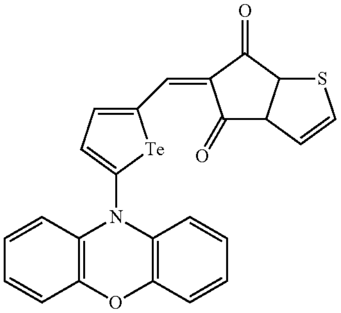
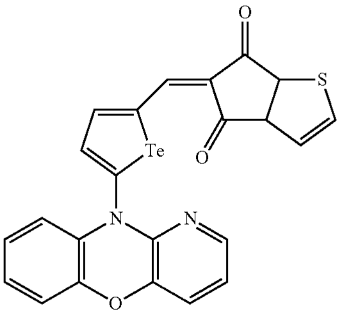
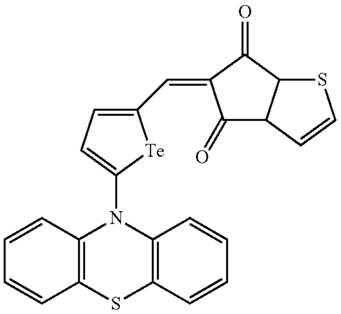

-continued
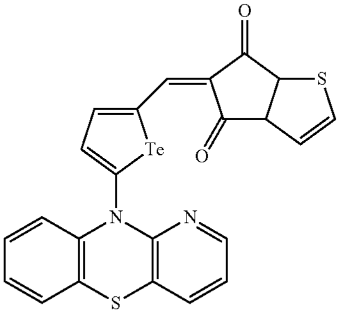
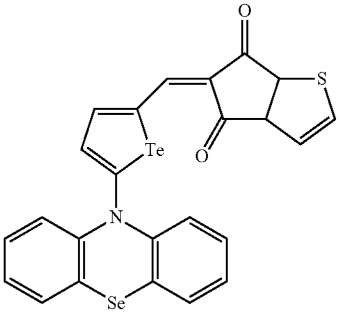
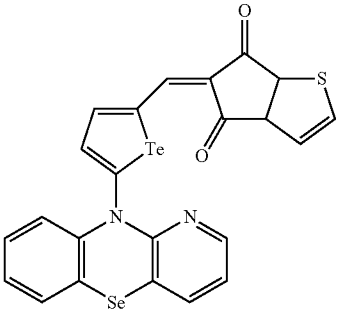
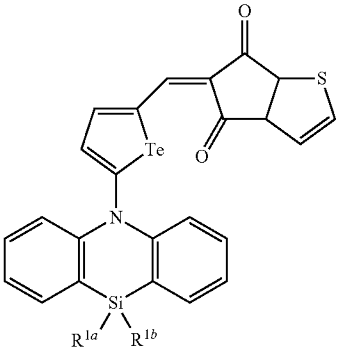
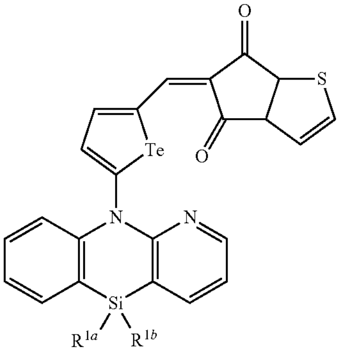
-continued
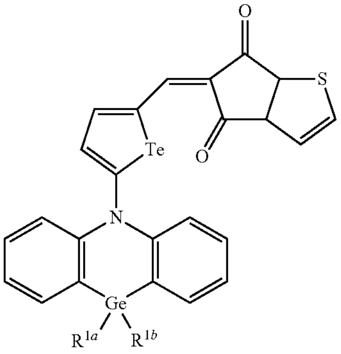
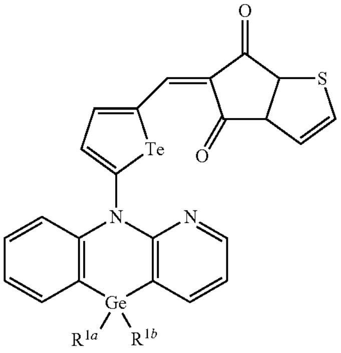
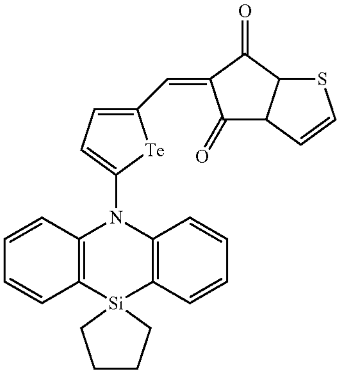
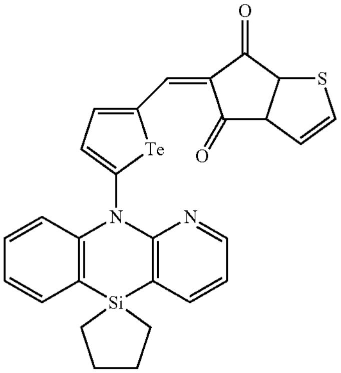

-continued
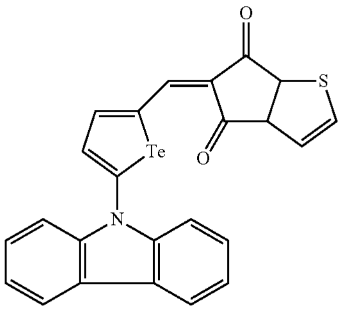
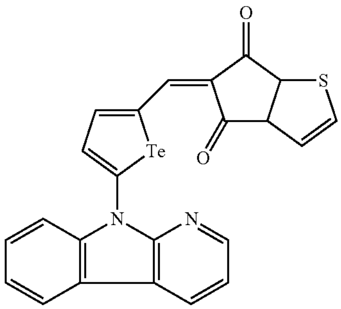
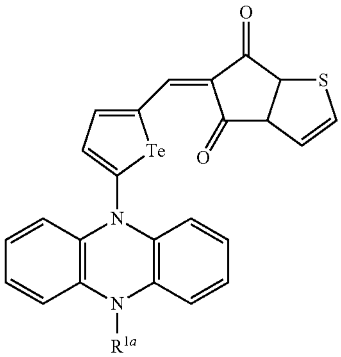
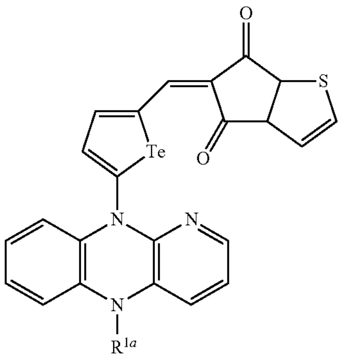
-continued
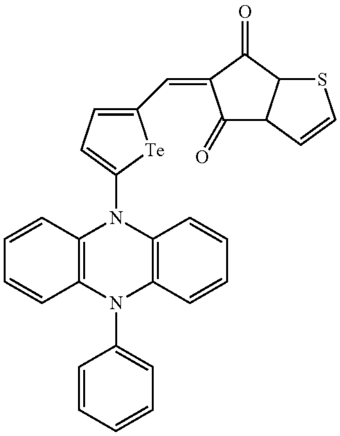
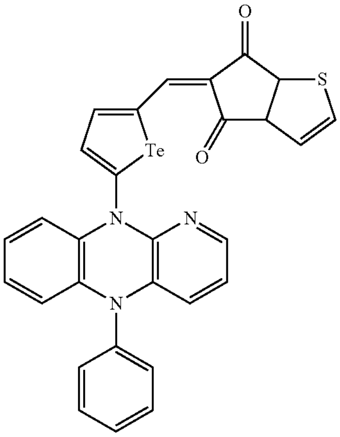
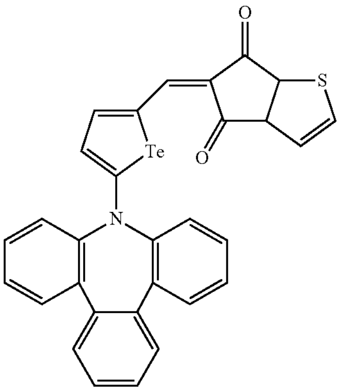
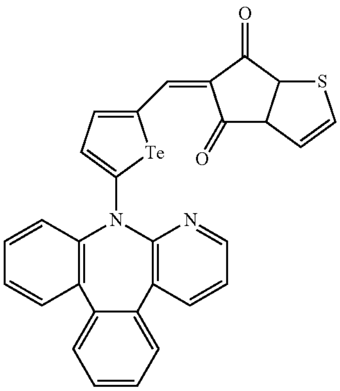

-continued
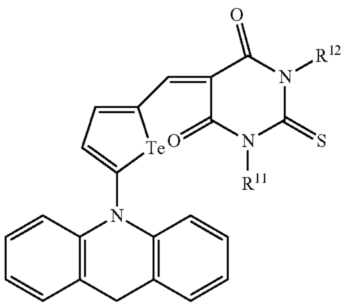
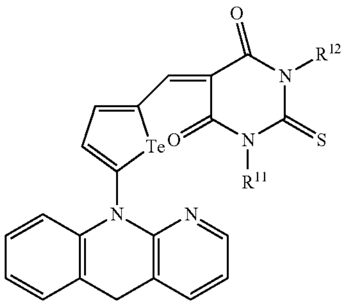
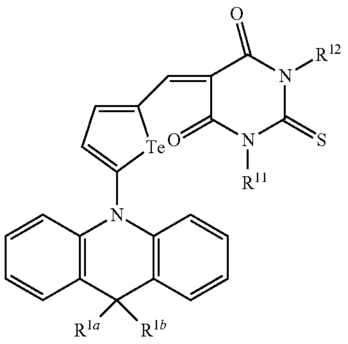
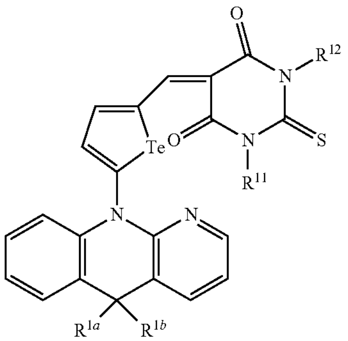
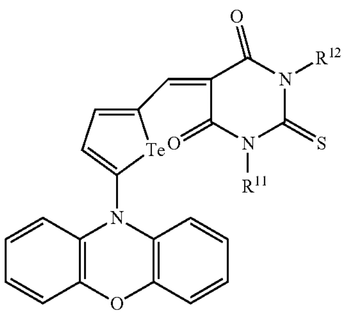
-continued
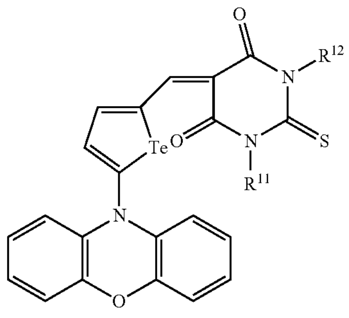
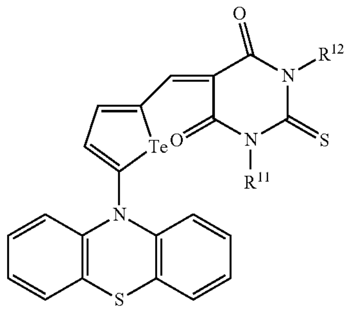
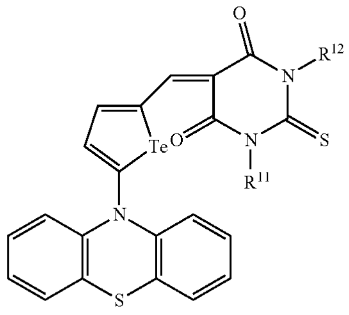
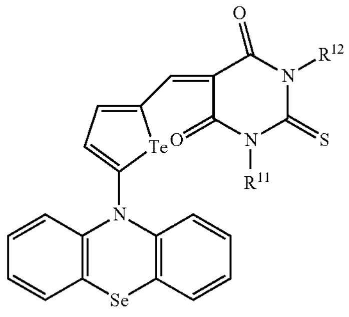
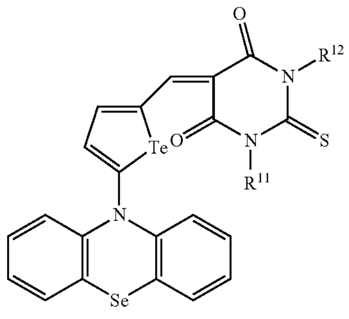

-continued
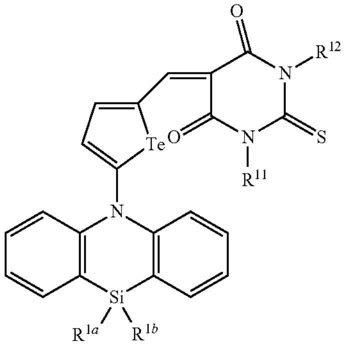
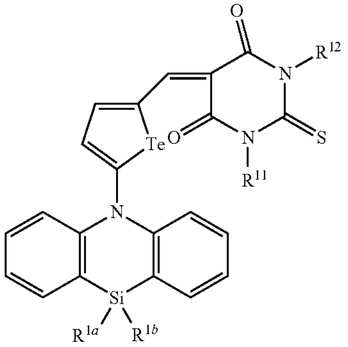
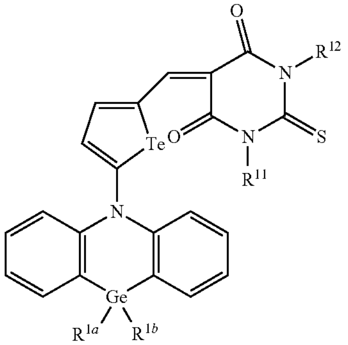
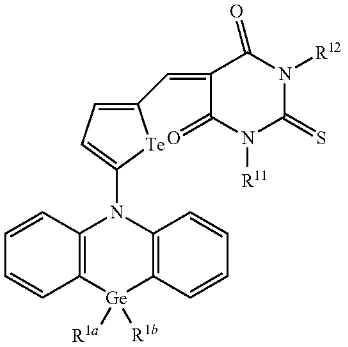
-continued
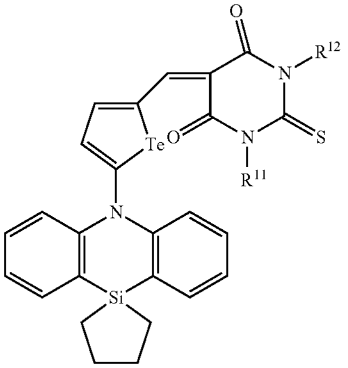
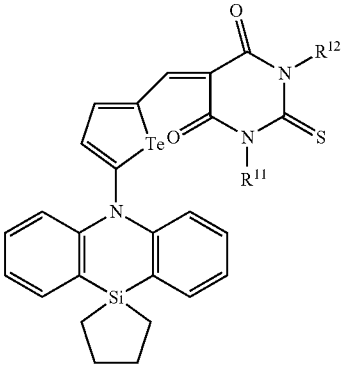
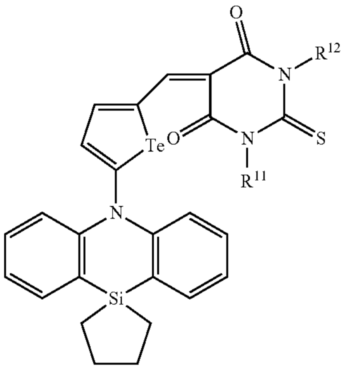
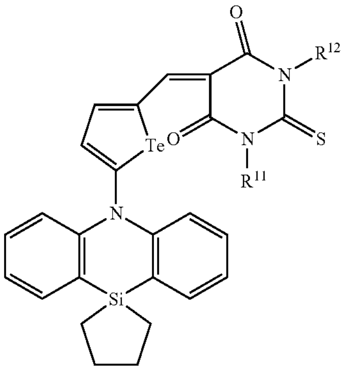

-continued
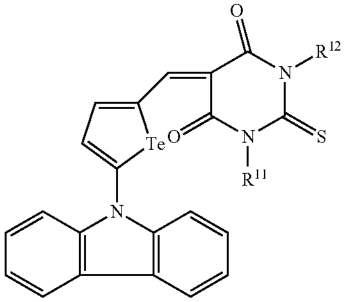
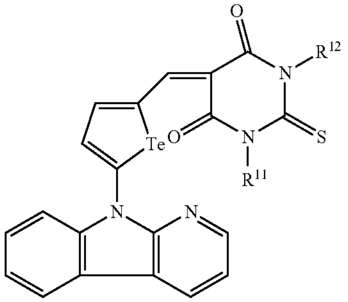
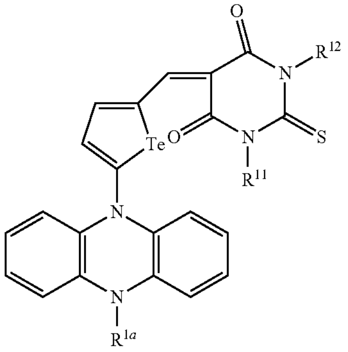
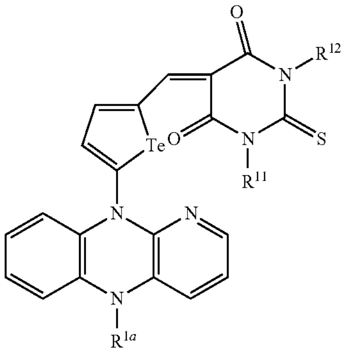
-continued
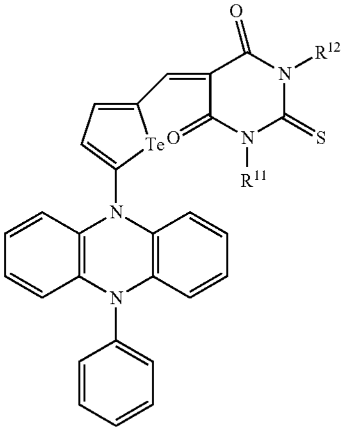
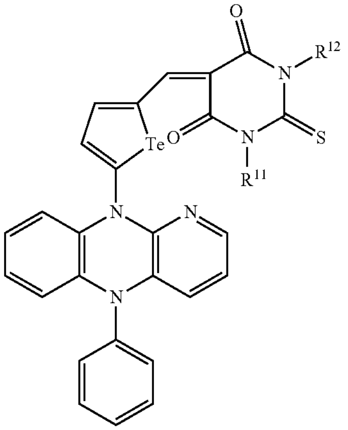
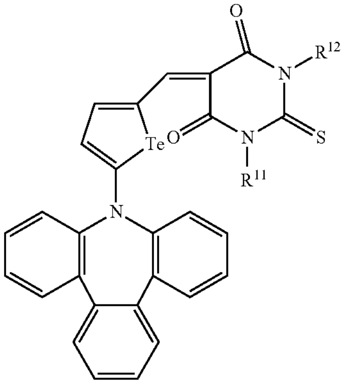
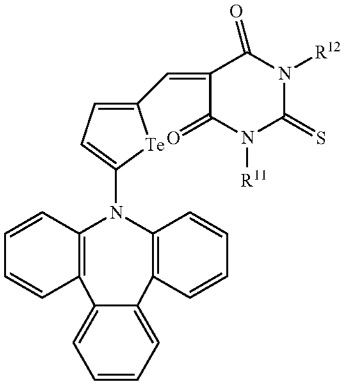

-continued
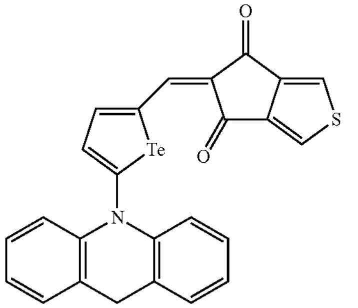
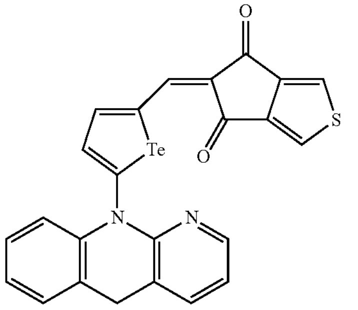
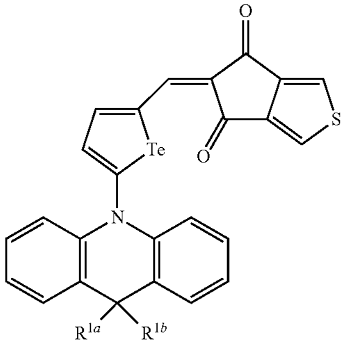
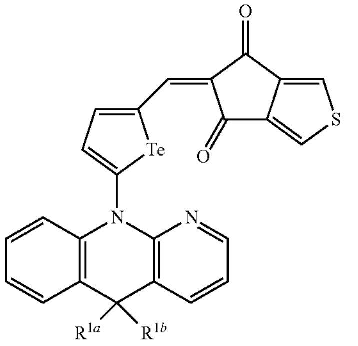
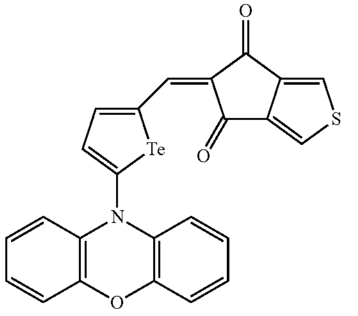
-continued
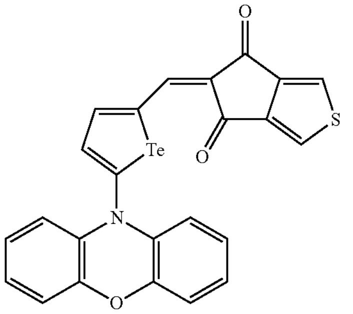
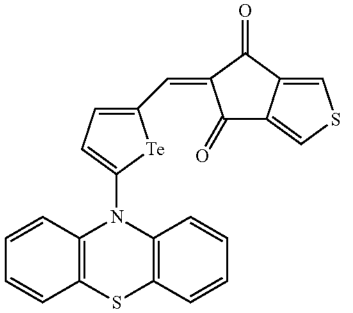
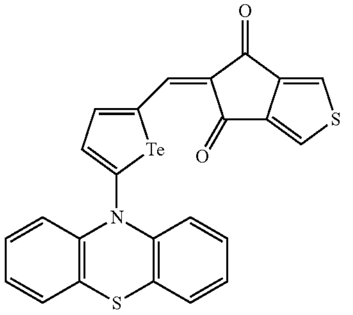
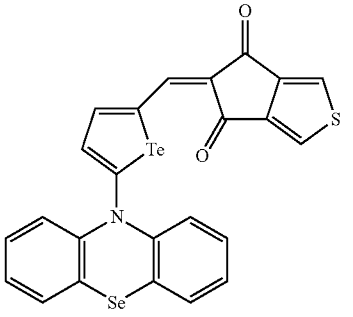
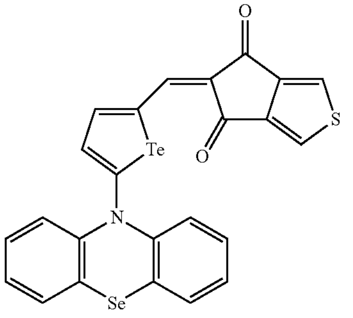

-continued
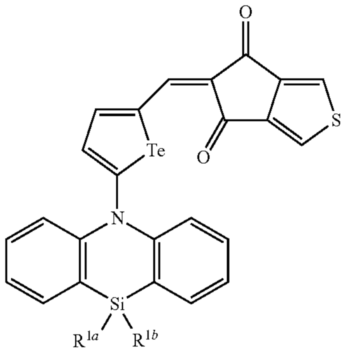
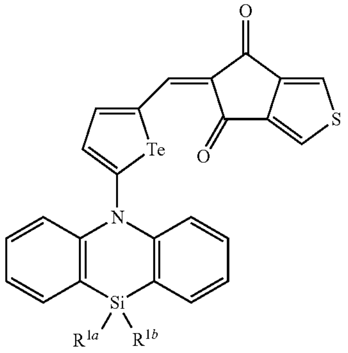
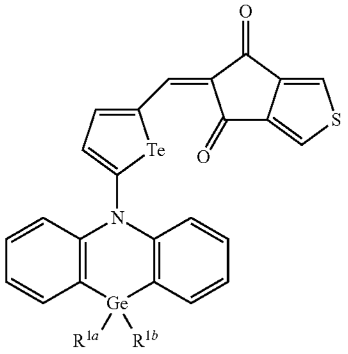
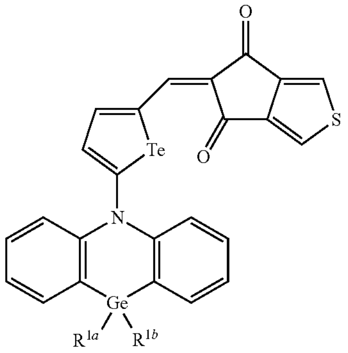
-continued
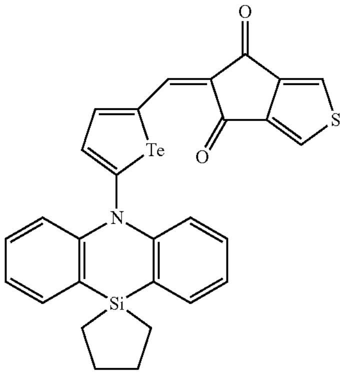
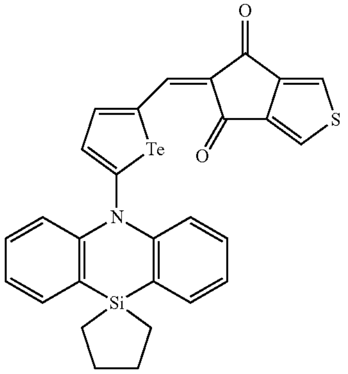
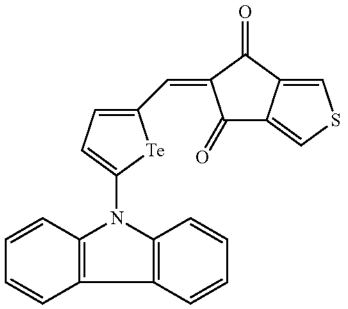
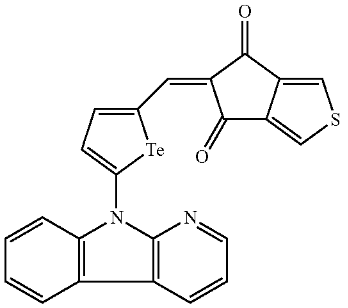
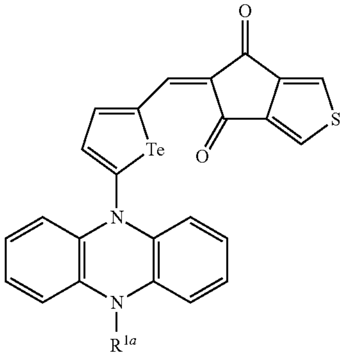

-continued

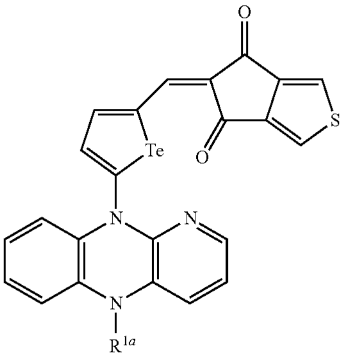

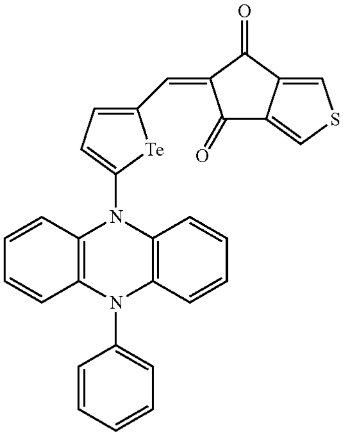

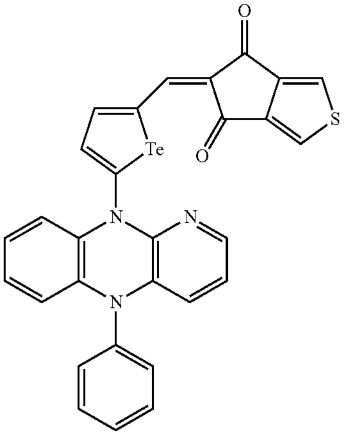

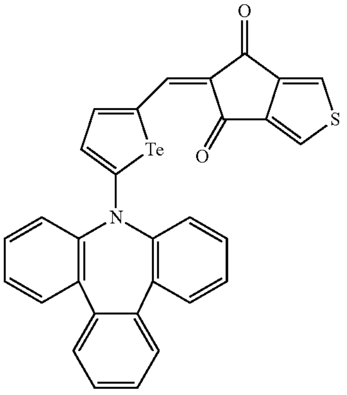

-continued

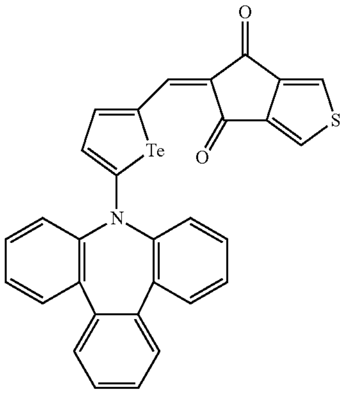

In Group 2B3, at least one hydrogen of each aromatic ring or heteroaromatic ring may be present (e.g., may not be replaced) or may be replaced by a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, or any combination thereof, and $R^{1a}$, $R^{1b}$, $R^{11}$, and $R^{12}$ may each independently be hydrogen or a C1 to C6 alkyl group.

[Group 2C]

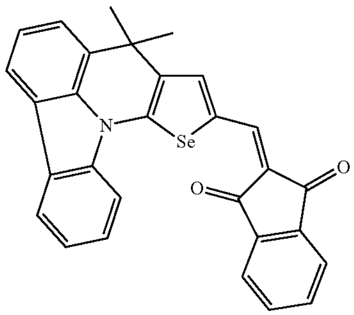

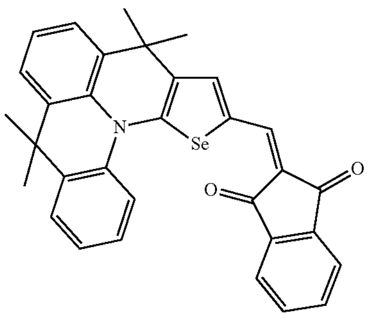

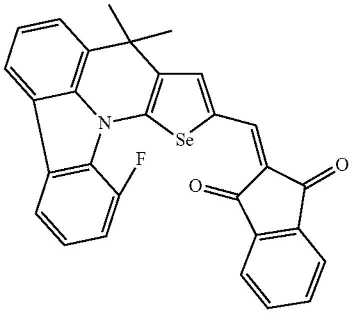
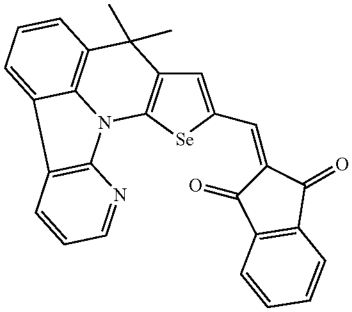
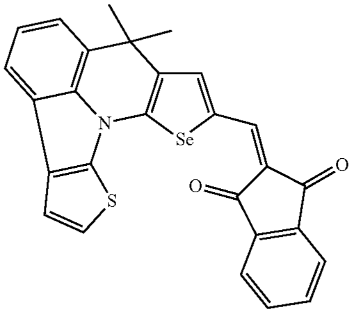
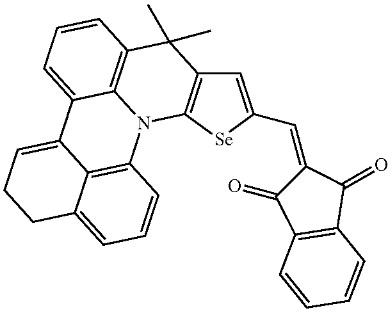
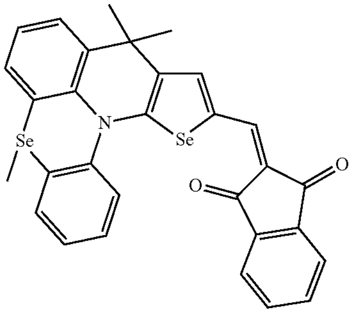
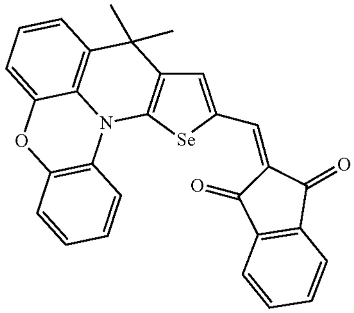
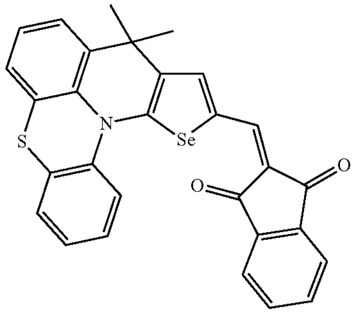
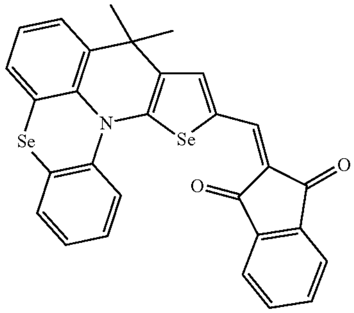
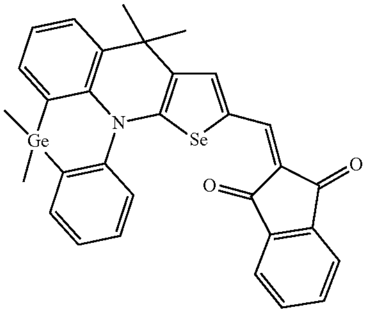
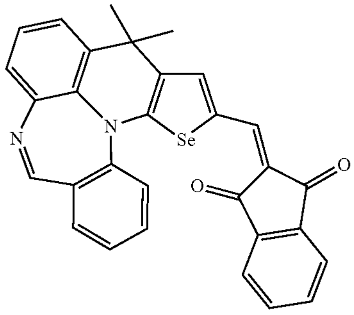

-continued
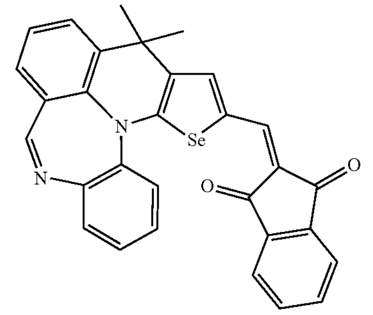
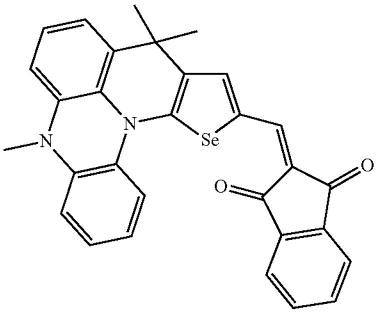
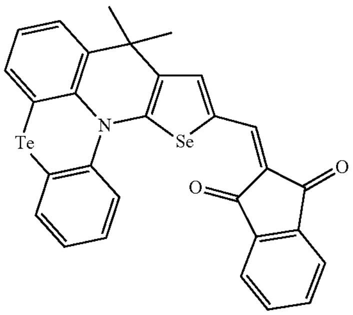
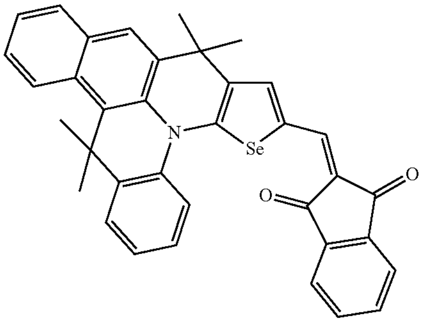
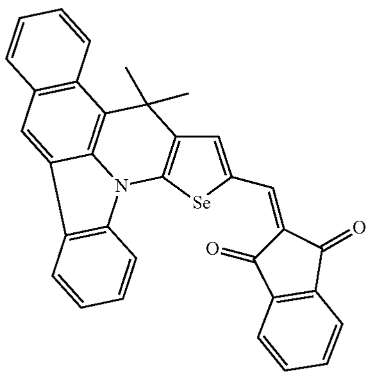
-continued
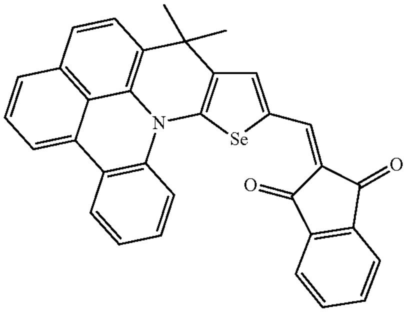
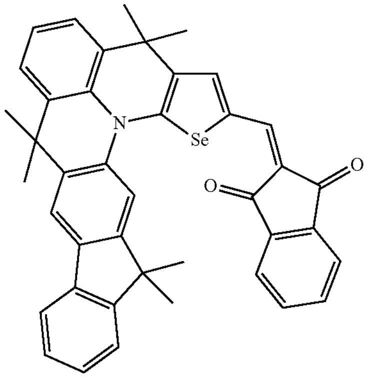
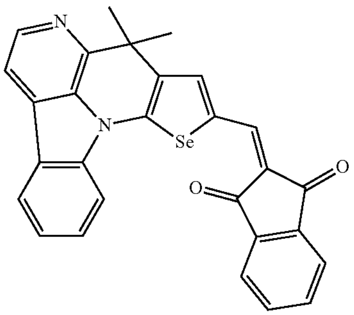
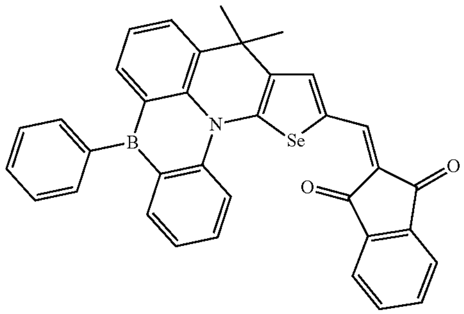
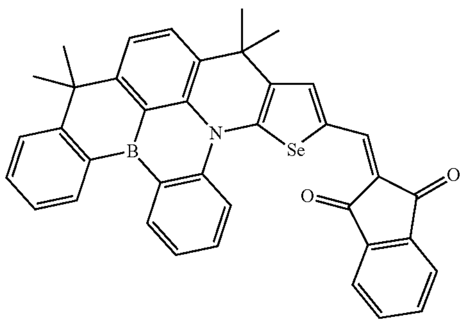

-continued
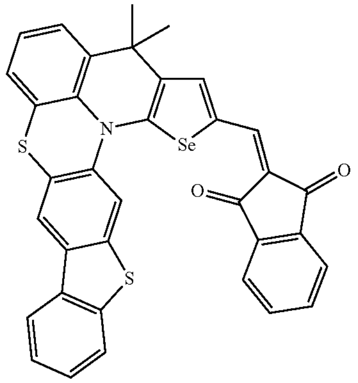
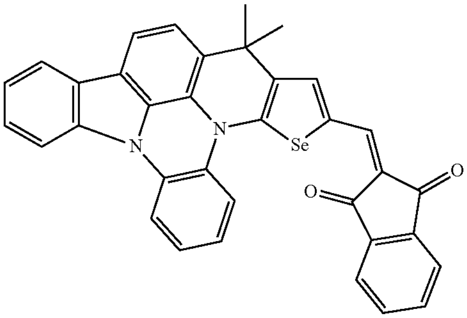
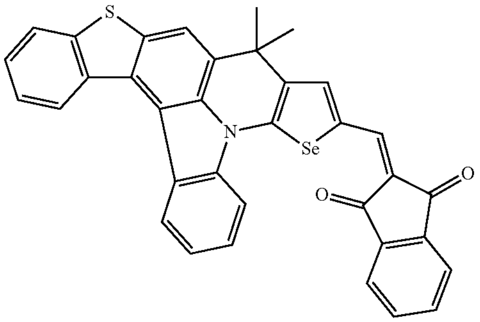
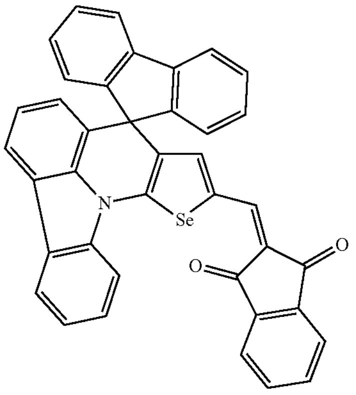
-continued
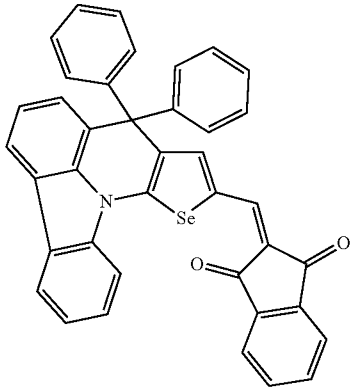
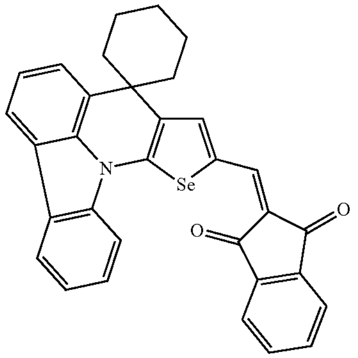
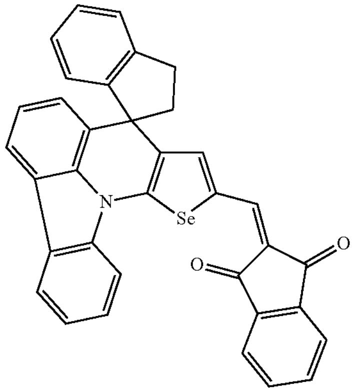
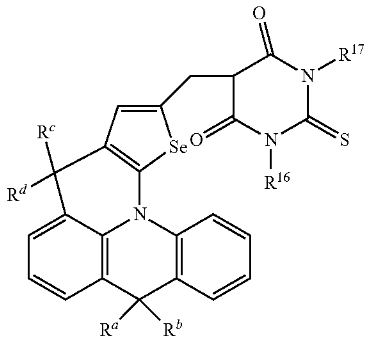

-continued
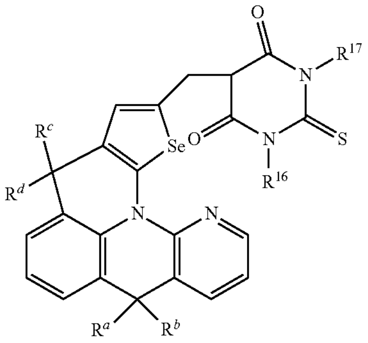
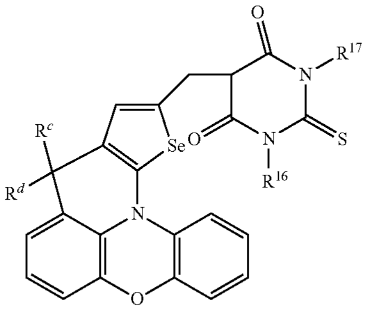
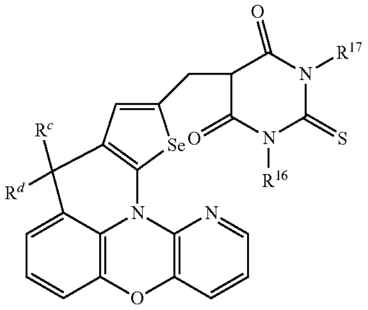
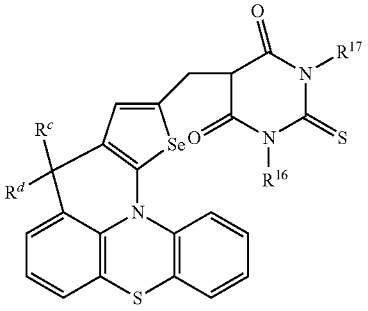
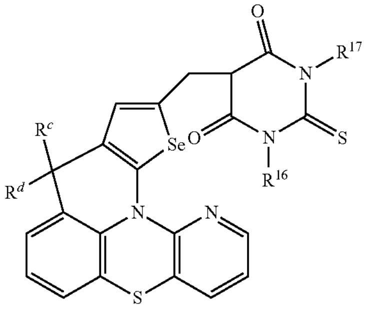
-continued
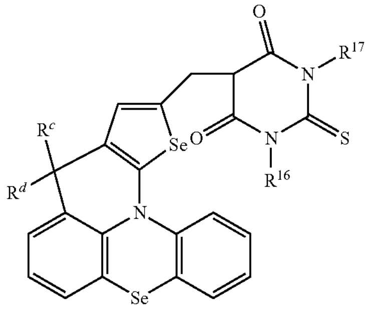
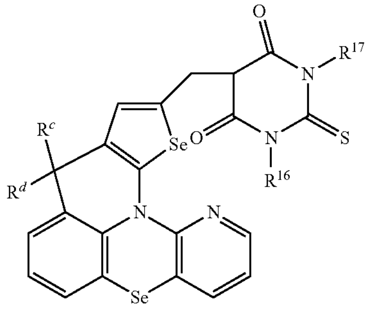
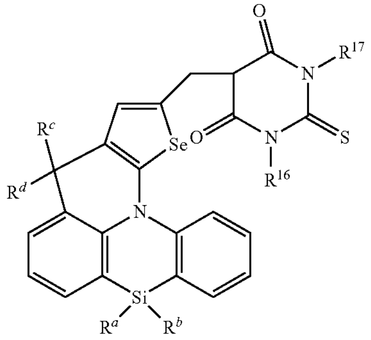
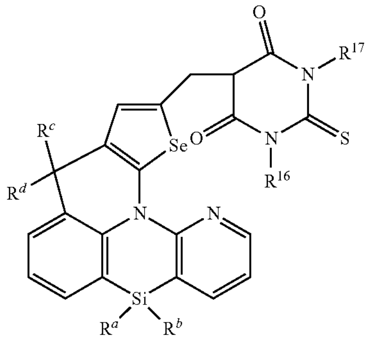
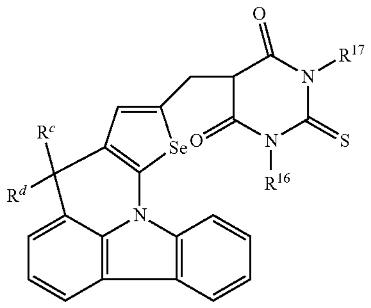

-continued

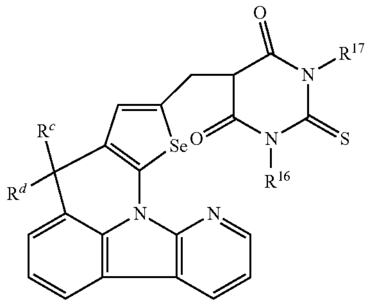

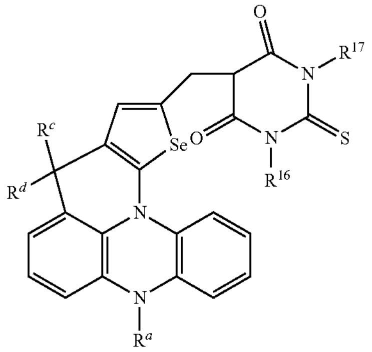

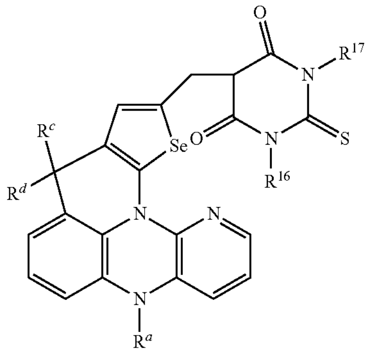

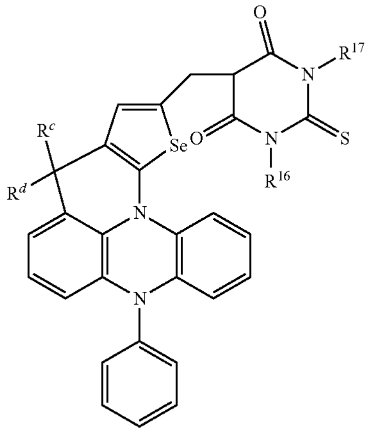

-continued

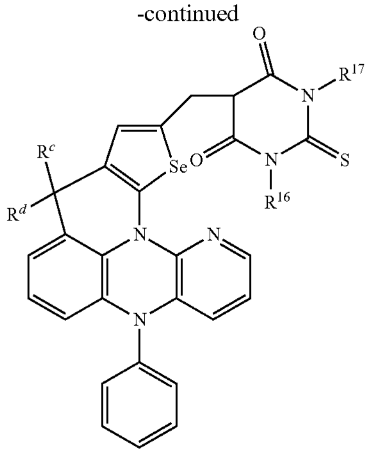

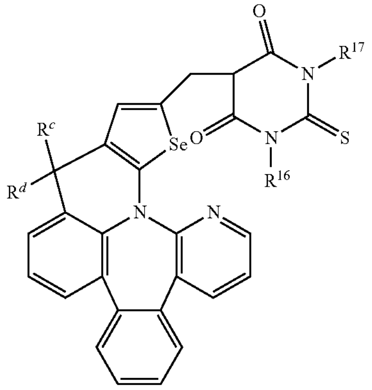

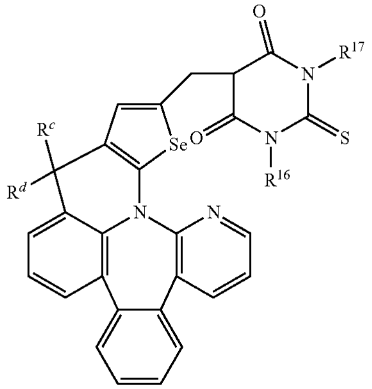

In Group 2C, at least one hydrogen of each aromatic ring or heteroaromatic ring may be present (e.g., may not be replaced) or may be replaced by a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, or any combination thereof, and $R^a$, $R^b$, $R^c$, $R^d$, $R^{16}$, and $R^{17}$ may each independently be hydrogen or a C1 to C6 alkyl group.

When the compound represented by Chemical Formula 1 is a p-type semiconductor (e.g., when a light absorbing layer includes a p-type semiconductor that includes and/or is the compound represented by Chemical Formula 1), the n-type semiconductor (e.g., which may be included in the light absorbing layer with the p-type semiconductor) may include fullerene, a fullerene derivative, a subphthalocyanine or subphthalocyanine derivative, a thiophene or thiophene derivative, or a compound represented by Chemical Formula 8.

A composition including a p-type semiconductor including the compound represented by Chemical Formula 1 and an n-type semiconductor including the following fullerene, fullerene derivative, subphthalocyanine or subphthalocyanine derivative, thiophene or thiophene derivative, or the compound represented by Chemical Formula 8 has improved absorption in the whole green wavelength region to improve the photoelectric conversion efficiency and to significantly reduce dark current of a photoelectric device and a light absorption sensor including the composition.

The compound represented by Chemical Formula 8 may include a planar core having an imide group or an anhydride group.

[Chemical Formula 8]

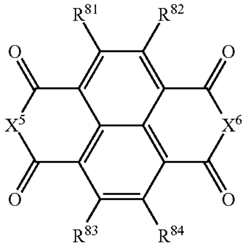

In Chemical Formula 8, $X^5$ and $X^6$ may each independently be O or $NR^a$, (wherein $R^a$ may be hydrogen, a substituted or unsubstituted C1 to C30 alkyl group, a substituted or unsubstituted C6 to C30 aryl group, a substituted or unsubstituted C3 to C30 heterocyclic group, a halogen, or a cyano group), $R^{81}$ to $R^{84}$ may each independently be hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

Examples of the fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 heterocycloalkyl group), and the like. Examples of the aryl groups and heterocyclic groups may be a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, a isobenzofuran ring, a benzimidazole ring, a imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathiin ring, a phenothiazine ring, or a phenazine ring.

The subphthalocyanine or subphthalocyanine derivative may be represented by Chemical Formula 9.

[Chemical Formula 9]

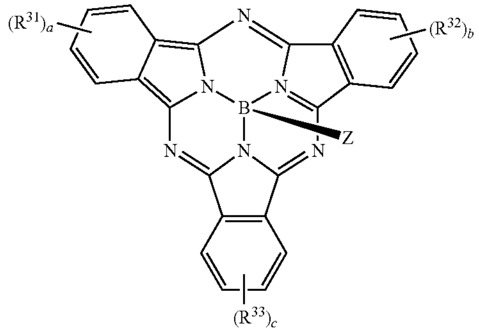

In Chemical Formula 9, $R^{31}$ to $R^{33}$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or any combination thereof, a, b, and c are integers ranging from 1 to 3, and Z may be a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one hydrogen of the alkyl group may be replaced by F, Cl, Br, or I.

The thiophene derivative may be for example represented by Chemical Formula 10 or Chemical Formula 11, but is not limited thereto.

[Chemical Formula 10]

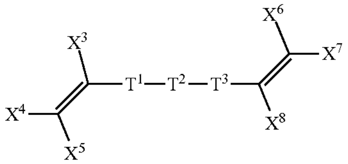

[Chemical Formula 11]

$$EWG^1—T^1—T^2—T^3—EWG^2$$

In Chemical Formula 10 and Chemical Formula 11, $T^1$, $T^2$, and $T^3$ may be aromatic rings including substituted or unsubstituted thiophene moieties, $T^1$, $T^2$, and $T^3$ may each independently be present or may be fused to each other, $X^3$ to $X^8$ may each independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or any combination thereof, and $EWG^1$ and $EWG^2$ may each independently be electron withdrawing groups.

For example, in Chemical Formula 10, at least one of $X^3$ to $X^8$ may be an electron withdrawing group, for example a cyano-containing group.

For example, specific examples of the compound represented by Chemical Formula 8 may include compounds represented by Chemical Formula 8A or 8B.

[Chemical Formula 8A]

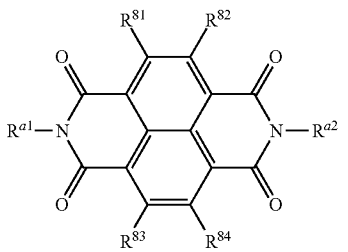

[Chemical Formula 8B]

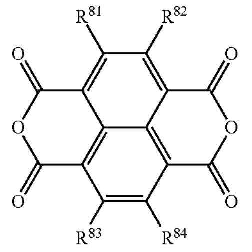

In Chemical Formula 8A and Chemical Formula 8B, $R^{81}$ to $R^{84}$, $R^{a1}$, and $R^{a2}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

For example, at least one of $R^{a1}$ or $R^{a2}$ may include an electron withdrawing group, and for example, $R^{a1}$ and $R^{a2}$ may each include an electron withdrawing group.

For example, at least one of $R^{a1}$ or $R^{a2}$ may be a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

For example, $R^{a1}$ and $R^{a2}$ may each independently be a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

For example, $R^{a1}$ and $R^{a2}$ may be the same as or different from each other, for example, may be the same.

The compound represented by Chemical Formula 8 may be, for example, one of compounds of Group 3, but is not limited thereto.

[Group 3]

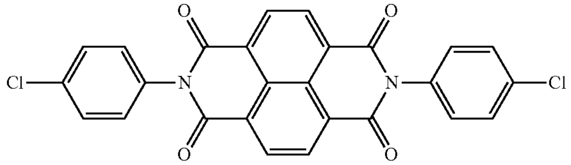

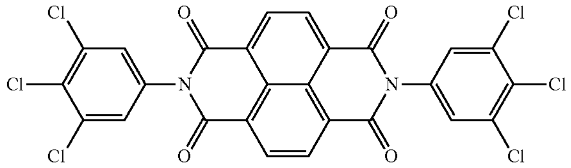

-continued

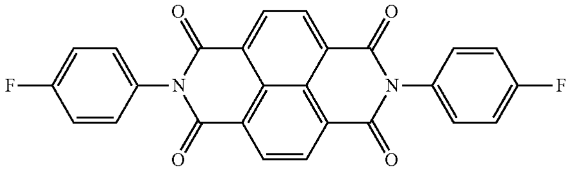

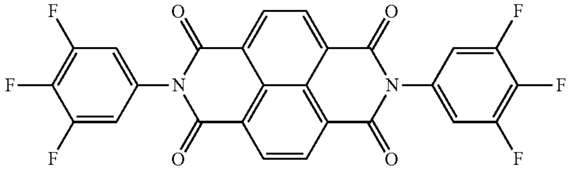

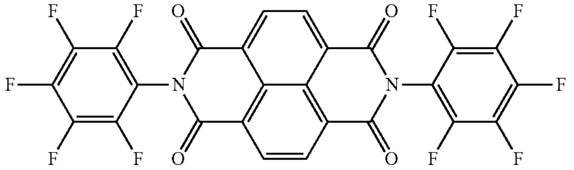

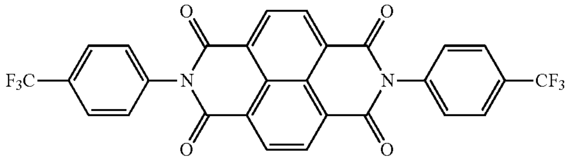

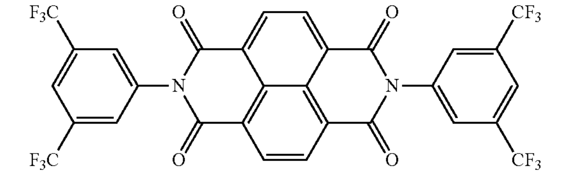

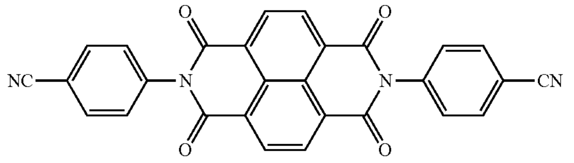

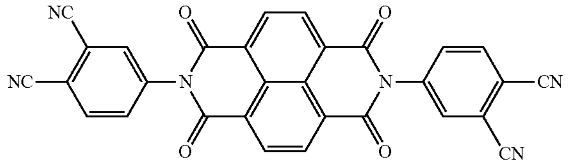

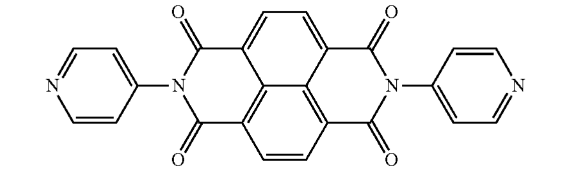

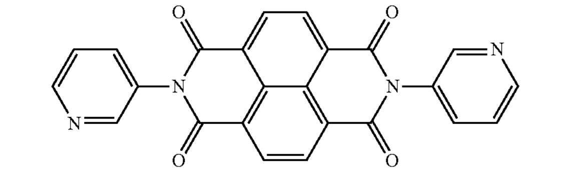

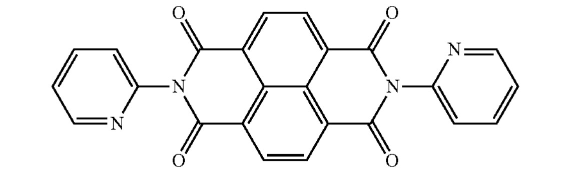

-continued

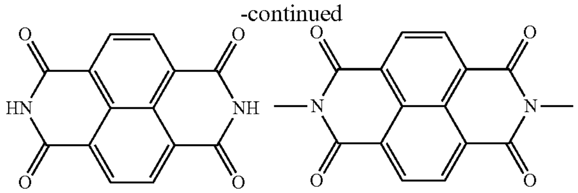

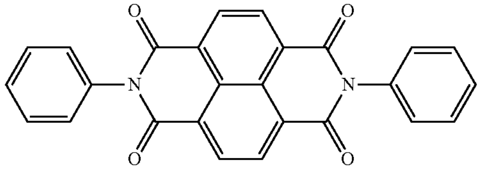

In Group 3, at least one hydrogen of each aromatic ring or heteroaromatic ring may be present (e.g., may not be replaced) or may be replaced by a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

Hereinafter, a photoelectric device including the compound according to some example embodiments is described with reference to drawings.

FIG. 1 is a cross-sectional view showing a photoelectric device according to some example embodiments.

Referring to FIG. 1, a photoelectric device 100 according to some example embodiments includes a first electrode 10 and a second electrode 20, and an active layer 30 between the first electrode 10 and the second electrode 20.

One of the first electrode 10 or the second electrode 20 is an anode and the other is a cathode. At least one of the first electrode 10 or the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 or the second electrode 20 is a non-light-transmitting electrode, it may include (e.g., may be made of), for example, an opaque conductor such as aluminum (Al).

The active layer 30 (hereinafter also referred to as a light absorbing layer) is a layer including a p-type semiconductor and an n-type semiconductor that form (e.g., establish, define, etc.) a pn junction, and absorbs external (e.g., incident) light to generate excitons and then separates the generated excitons into holes and electrons.

The active layer 30 includes the compound represented by Chemical Formula 1. The compound may be applied as a p-type semiconductor or an n-type semiconductor in the active layer 30.

As described above, when the compound represented by Chemical Formula 1 included in the active layer 30 is an n-type semiconductor, the p-type semiconductor may include the compound represented by Chemical Formula 7. Descriptions thereof are the same as described above. When used in such a combination, the external quantum efficiency of the photoelectric device may be significantly increased.

In addition, when the compound represented by Chemical Formula 1 is a p-type semiconductor, the n-type semiconductor may include fullerene, a fullerene derivative, subphthalocyanine or subphthalocyanine derivative, thiophene or a thiophene derivative, or the compound represented by Chemical Formula 8. Descriptions thereof are the same as described above. When used in such a combination, the external quantum efficiency of the photoelectric device may be significantly increased.

In some example embodiments, the active layer 30 may include a compound represented by Chemical Formula 1 and may include another one or more compounds different from the compounds represented by Chemical Formulas 7 and 8, such that the active layer 30 may not include any compounds represented by either Chemical Formula 7 or Chemical Formula 8.

In some example embodiments, the active layer 30 may include different compounds that are different example embodiments of compounds represented by Chemical Formula 1 having different LUMO energy levels and different HOMO energy levels, where one of the different example embodiments serves as a p-type semiconductor in the active layer 30 and a different one of the different example embodiments serves as an n-type semiconductor in the active layer 30, and the active layer 30 may not include any compounds represented by either Chemical Formula 7 or Chemical Formula 8. For example, the active layer 30 may include both a first compound that is a first example embodiment of a compound represented by Chemical Formula 1 (e.g., a compound represented by Chemical Formula 1 where $Ar^2$ is a cyclic group represented by Chemical Formula 5) having a LUMO energy level (e.g., in the range of about 3.5 eV to about 4.5 eV, although example embodiments are not limited thereto) and a second compound that is different from the first compound and is a second example embodiment of a compound represented by Chemical Formula 1 (e.g., a compound represented by Chemical Formula 1 where $Ar^2$ is a cyclic group represented by Chemical Formula 6F) that is different from the first example embodiment of the compound represented by Chemical Formula 1 and has a different LUMO energy level (e.g., in the range of about 2.5 eV to about 3.9 eV, although example embodiments are not limited thereto), such that the first example embodiment of the compound may be present as one of a p-type semiconductor or an n-type semiconductor in the active layer 30 and the second example embodiment of the compound may be present as another, different one of an n-type semiconductor or a p-type semiconductor in the active layer 30, where the first and second embodiments of the compound may form a pn junction.

The active layer 30 may have a maximum absorption wavelength (Amax) in a wavelength range of greater than or equal to about 500 nm and less than or equal to about 600 nm, for example, greater than or equal to about 510 nm and less than or equal to about 580 nm, or greater than or equal to about 520 nm and less than or equal to about 555 nm.

The active layer 30 has an absorption curve having a relatively small full width at half maximum (FWHM) of about 50 nm to about 150 nm, for example about 50 nm to about 120 nm, about 50 nm to about 110 nm, or about 50 nm to about 100 nm. Accordingly, the active layer 30 may have high selectivity for light in the whole green wavelength region.

The active layer 30 may include a bi-layer including a p-type layer including the aforementioned p-type semiconductor and an n-type layer including the aforementioned n-type semiconductor. In this case, a thickness ratio of the p-type layer and the n-type layer may be about 1:9 to about 9:1, for example, about 2:8 to about 8:2, about 3:7 to about 7:3, about 4:6 to about 6:4 or about 5:5.

The active layer 30 may be an intrinsic layer (I layer) in which a p-type semiconductor and an n-type semiconductor are blended to form a bulk heterojunction. The intrinsic layer (I layer) may include the p-type semiconductor and the n-type semiconductor in a volume ratio (thickness ratio) of about 1:9 to about 9:1, for example, about 2:8 to about 8:2, about 3:7 to about 7:3, about 4:6 to about 6:4, or about 5:5. By having the volume ratio in the above range, an exciton may be effectively produced, and a pn junction may be effectively formed.

The active layer 30 may further include a p-type layer and/or an n-type layer in addition to the intrinsic layer. The p-type layer may include the aforementioned p-type semiconductor, and the n-type layer may include the aforementioned n-type semiconductor. The active layer 30 may be, for example, an intrinsic layer (I layer), a p-type layer/I layer, an I layer/n-type layer, a p-type layer/I layer/n-type layer, a p-type layer/n-type layer, and the like.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90% or more.

In the photoelectric device 100, when light enters from the first electrode 10 and/or second electrode 20, and when the active layer 30 absorbs light in a desired and/or alternatively particular (or, alternatively, predetermined) wavelength region, excitons may be produced from the inside. The excitons are separated into holes and electrons in the active layer 30, and the separated holes are transported to an anode that is one of the first electrode 10 or the second electrode 20 and the separated electrons are transported to the cathode that is the other of the first electrode 10 or the second electrode 20 so as to flow a current in the photoelectric device.

Hereinafter, a photoelectric device according to some example embodiments is described with reference to FIG. 2.

Figure 2:
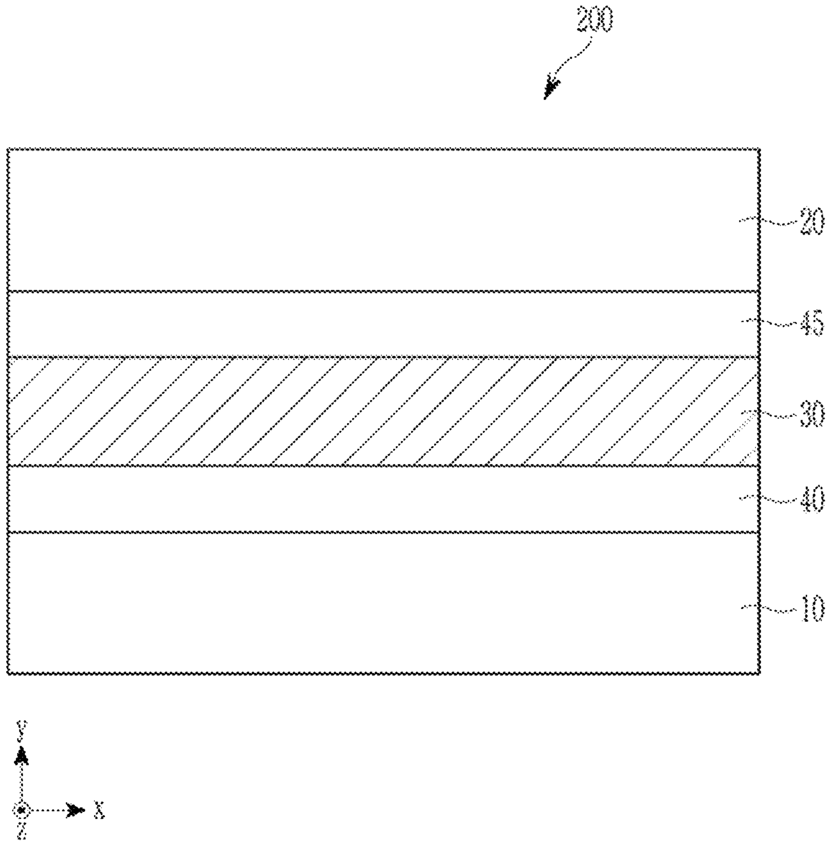
FIG. 2 is a cross-sectional view showing a photoelectric device according to some example embodiments.

FIG. 2 is a cross-sectional view showing a photoelectric device according to some example embodiments.

Referring to FIG. 2, a photoelectric device 200 according to some example embodiments includes a first electrode 10 and a second electrode 20 facing each other, and an active layer 30 between the first electrode 10 and the second electrode 20, like some example embodiments, including the example embodiments shown in FIG. 1.

However, the photoelectric device 200 according to some example embodiments, including the example embodiments shown in FIG. 2 further includes charge auxiliary layers 40 and 45 between the first electrode 10 and the active layer 30, and the second electrode 20 and the active layer 30, unlike some example embodiments, including the example embodiments shown in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole injection layer (HIL) and/or hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino] biphenyl (α-NPD), m-MTDATA, 4,4',4"-tris(N-carbazolyl)-triphenylamine (TCTA), and any combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis [N-(1-naphthyl)-N-phenyl-amino]biphenyl (α-NPD), m-MTDATA, 4,4',4"-tris(N-carbazolyl)-triphenylamine (TCTA), and any combination thereof, but is not limited thereto.

The electron injection layer (EIL) and/or electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and any combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and any combination thereof, but is not limited thereto.

Either one of the charge auxiliary layers 40 or 45 may be omitted.

The photoelectric devices 100 and 200 may be applied to a solar cell, a light absorption sensor (e.g., an image sensor), a photo detector, an optical sensor, and a light emitting element, but is not limited thereto.

Hereinafter, an example of an image sensor including the organic photoelectric device is described referring to drawings. As an example of an image sensor, also referred to herein as a light absorption sensor, an organic CMOS image sensor according to some example embodiments is described, but it will be understood that the example embodiments are not limited thereto.

Figure 3:
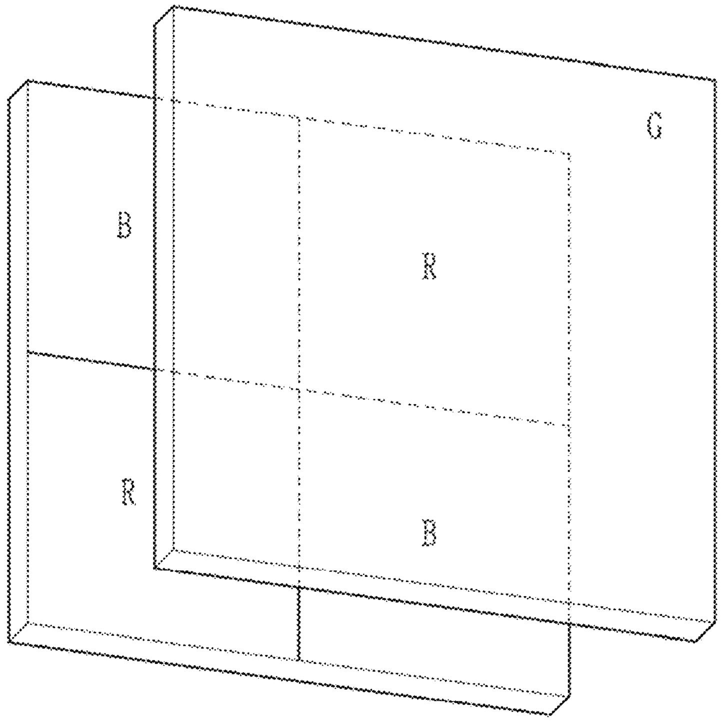
FIG. 3 is a plan view schematically illustrating an organic CMOS image sensor according to some example embodiments.
Figure 4:
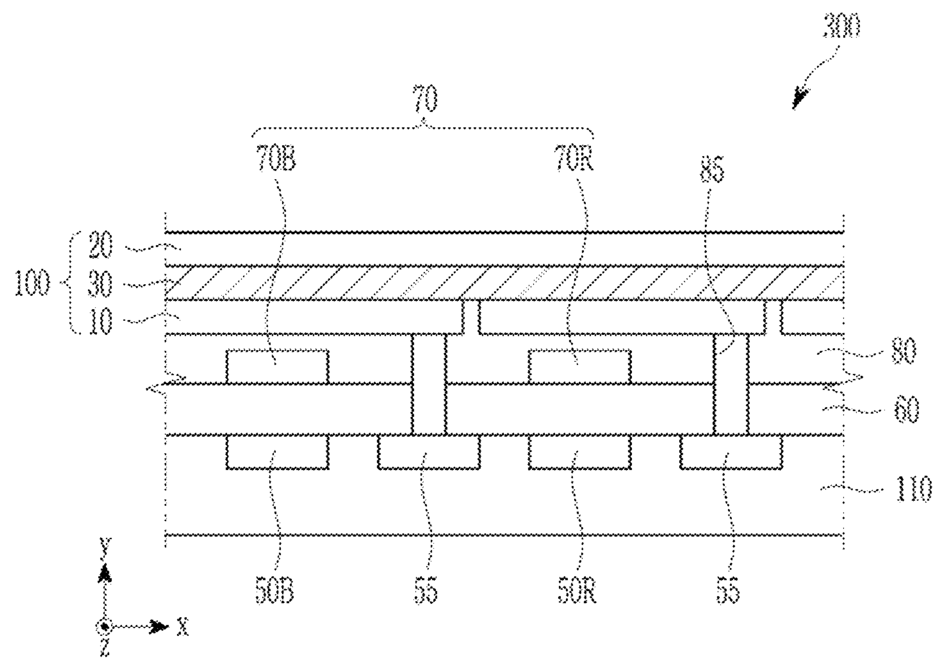
FIG. 4 is a cross-sectional view of the organic CMOS image sensor of FIG. 3.

FIG. 3 is a schematic top plan view showing an organic CMOS image sensor according to some example embodiments, and FIG. 4 is a cross-sectional view showing the organic CMOS image sensor of FIG. 3.

Referring to FIGS. 3 and 4, an organic CMOS image sensor 300 according to some example embodiments includes a semiconductor substrate 110 integrated with photo-sensing devices 50B and 50R, which may be referred to as a blue photo-sensing device 50B and a red photo-sensing device 50R, a transmission transistor (not shown), a charge storage 55, a lower insulation layer 60, a color filter layer 70, an upper insulation layer 80, and a photoelectric device 100.

The semiconductor substrate 110 may be a silicon substrate, and is integrated with the photo-sensing devices 50B and 50R, the transmission transistor (not shown), and the charge storage 55. The photo-sensing devices 50B and 50R may be photodiodes.

The photo-sensing devices 50B and 50R, the transmission transistor, and/or the charge storage 55 may be integrated in each pixel, for example may be integrated in the semiconductor substrate 110 such that the photo-sensing devices 50B and 50R are located within a volume space defined by outermost surface of the semiconductor substrate 110 and may be at least partially exposed by the semiconductor substrate 110 or may be enclosed within an interior of the semiconductor substrate 110, and as shown in the drawing, the photo-sensing devices 50B and 50R may be respectively included in a blue pixel and a red pixel and the charge storage 55 may be included in a green pixel. The blue photo-sensing device 50B may be configured to sense (e.g., selectively sense, including selectively absorbing and photoelectrically converting) blue light which is light in a blue wavelength region, and the red photo-sensing device 50R may be configured to sense (e.g., selectively sense, including selectively absorbing and photoelectrically converting) red light which is light in a red wavelength region.

The photo-sensing devices 50B and 50R may be configured to sense (e.g., selectively sense) light, the information sensed by the photo-sensing devices 50B and 50R may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and configured to selectively transmit blue light and a red filter 70R formed in the red pixel and configured to selectively transmit red light. In some example embodiments, a cyan filter and a yellow filter may be disposed instead of the blue filter 70B and red filter 70R. In some example embodiments, including the example embodiments shown in FIGS. 3 and 4, a green filter is not included, but a green filter may be further included in some example embodiments.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In some example embodiments, in FIG. 4, additional color filters may be further disposed on the photoelectric device 100. The additional color filters may include a blue filter 70B and a red filter 70R or a cyan filter and a yellow filter.

Figure 5:
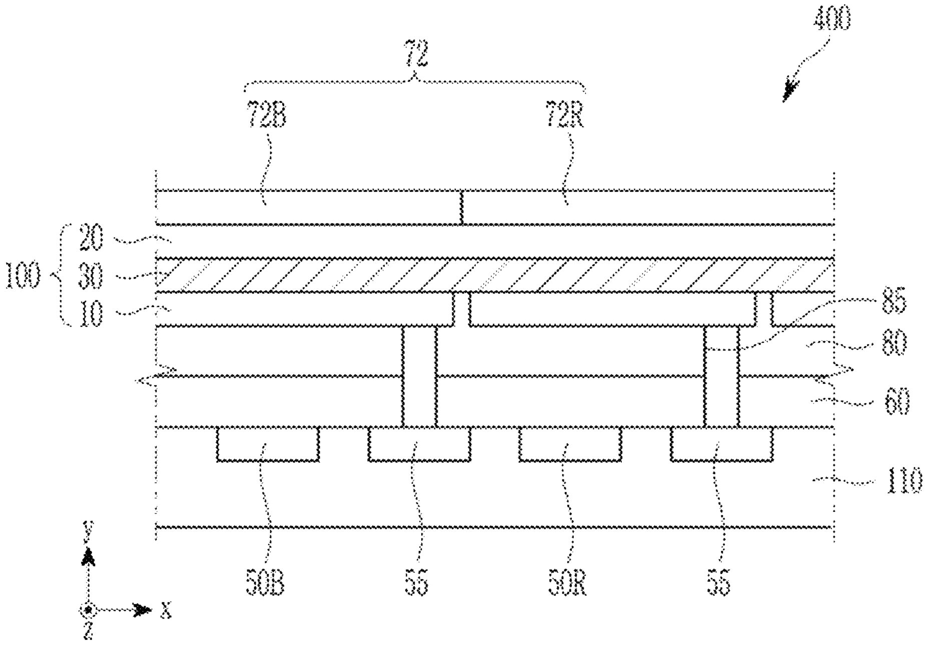
FIG. 5 is a cross-sectional view schematically illustrating an organic CMOS image sensor according to some example embodiments.

The organic CMOS image sensor with the color filters disposed on the photoelectric device is shown in FIG. 5.

FIG. 5 is a schematic cross-sectional view showing an organic CMOS image sensor according to some example embodiments. Referring to FIG. 5, an organic CMOS image sensor 400 has the same structure as FIG. 4 except that a color filter layer 72 including the blue filter 72B and the red filter 72R is disposed on the photoelectric device 100 instead of a color filter layer 70 including the blue filter 70B and the red filter 70R disposed on the lower insulating layer 70. Instead of the blue filter 72B and the red filter 72R, a cyan filter and a yellow filter may be disposed respectively.

In FIGS. 4 and 5, the photoelectric device 100 of FIG. 1 is included, but it is not limited thereto, and thus the photoelectric device 200 of FIG. 2 may be applied in the same manner.

Figure 6:
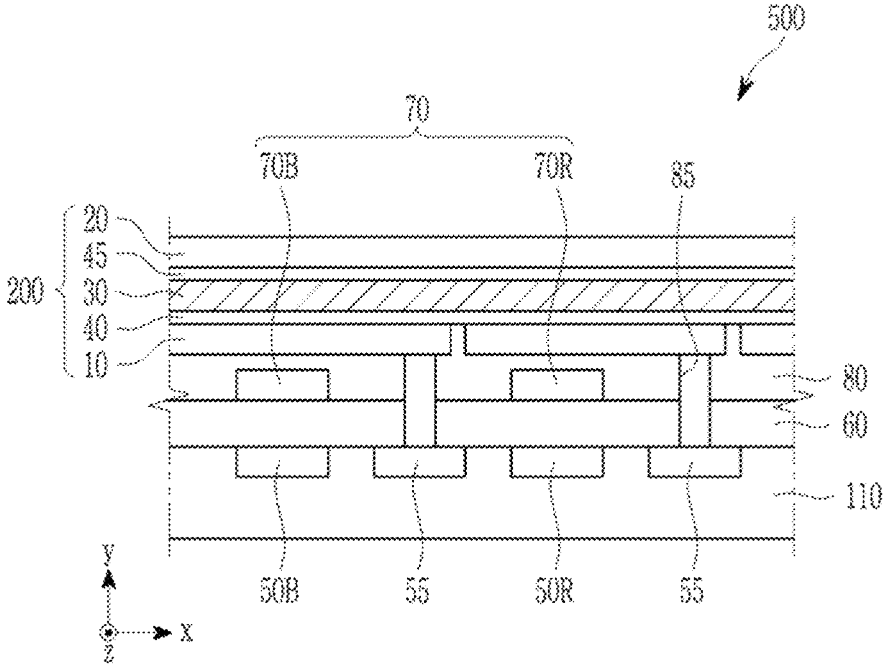
FIG. 6 is a cross-sectional view schematically illustrating an organic CMOS image sensor according to some example embodiments.

FIG. 6 is a cross-sectional view showing an organic CMOS image sensor 500 to which the photoelectric device 200 is applied.

Referring to FIG. 6, the organic CMOS image sensor 500 includes a semiconductor substrate 110 integrated with photo-sensing devices 50B and 50R, a transmission transistor (not shown), and a charge storage 55, a lower insulation layer 60, and an upper insulation layer 80, like some example embodiments, including the example embodiments shown in FIG. 4.

However, the organic CMOS image sensor 500 according to some example embodiments, including the example embodiments shown in FIG. 6, includes the photoelectric device 200, unlike some example embodiments, including the example embodiments shown in FIG. 4, which include the photoelectric device 100.

Figure 7:
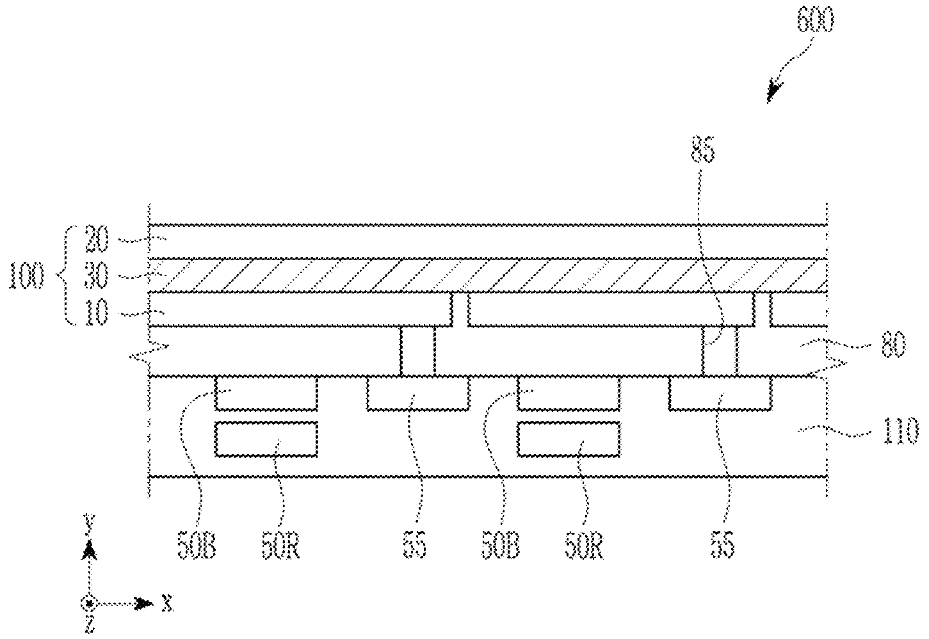
FIG. 7 is a cross-sectional view of an organic CMOS image sensor according to some example embodiments.

FIG. 7 is a schematic view showing an organic CMOS image sensor according to some example embodiments.

Referring to FIG. 7, the organic CMOS image sensor 600 includes a semiconductor substrate 110 integrated with photo-sensing devices 50B and 50R, a transmission transistor (not shown), and a charge storage 55, an insulation layer 80, and a photoelectric device 100, like some example embodiments, including the example embodiments illustrated in FIG. 5.

However, the organic CMOS image sensor 600 according to some example embodiments includes the blue photo-sensing device 50B and the red photo-sensing device 50R that are stacked in a vertical direction (e.g., perpendicular to a direction in which the upper surface of the semiconductor substrate 110 extends as shown in FIG. 7) in the semiconductor substrate 110 and does not include a color filter layer 70 and a lower insulation layer 60, unlike some example embodiments, including the example embodiments illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8A:
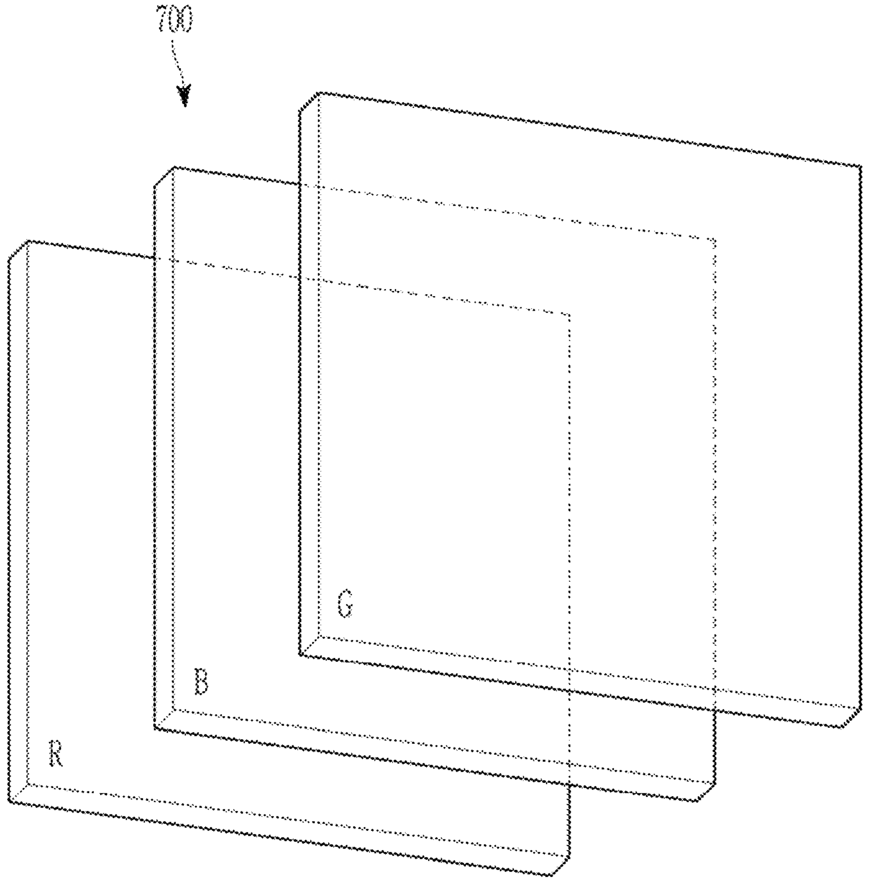
FIG. 8A is a schematic view schematically illustrating an organic CMOS image sensor according to some example embodiments.
Figure 8B:
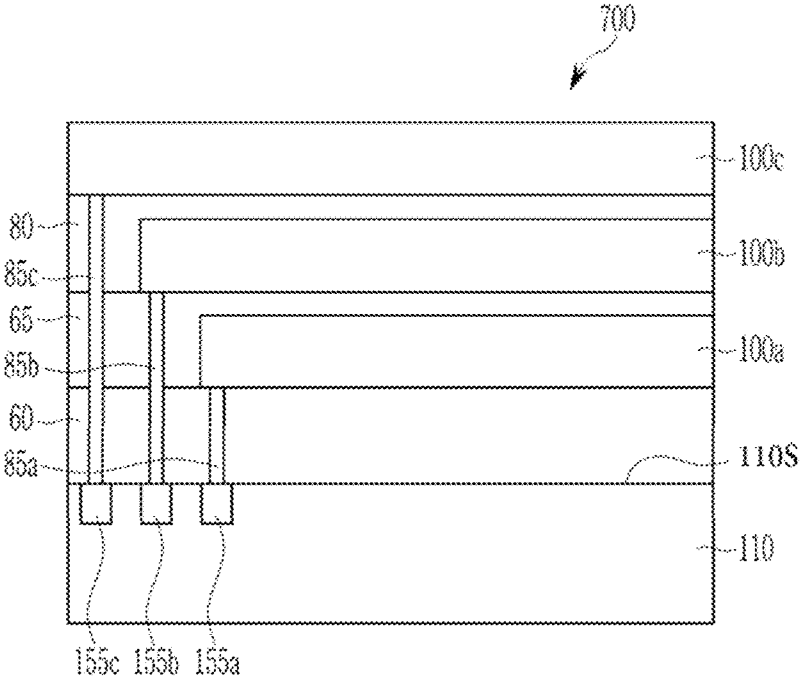
FIG. 8B is a cross-sectional view of the organic CMOS image sensor of FIG. 8A.

FIG. 8A is a schematic view showing an organic CMOS image sensor according to some example embodiments and FIG. 8B is a cross-sectional view of the organic CMOS image sensor of FIG. 8A.

Referring to FIGS. 8A and 8B, the organic CMOS image sensor 700 according to some example embodiments includes a green photoelectric device (G) configured to selectively absorb light in a green wavelength region, a blue photoelectric device (B) configured to selectively absorb light in a blue wavelength region, and a red photoelectric device configured to selectively absorb light in a red wavelength region that are stacked. For example, the organic CMOS image sensor 700 may include a green photoelectric device configured to selectively sense light in a green wavelength region, a blue photoelectric device configured to selectively sense light in a blue wavelength region, and a red photoelectric device configured to selectively sense light in a red wavelength region, where the green photoelectric device, the blue photoelectric device, and the red photoelectric device are stacked as shown in at least FIG. 8A. As shown, the photoelectric devices 100*a* to 100*c* may be stacked in a vertical direction on the semiconductor substrate 110, such that the photoelectric devices 100*a* to 100*c* at least partially overlap each other in a vertical direction that is perpendicular to an upper surface 110S of the semiconductor substrate 110, but example embodiments are not limited thereto.

The organic CMOS image sensor 700 according to some example embodiments includes a semiconductor substrate 110, a lower insulation layer 60, an intermediate insulation layer 65, an upper insulation layer 80, a first device (i.e., photoelectric device, the same below) 100*a*, a second device 100*b*, and a third device 100*c*.

The semiconductor substrate 110 may be a silicon substrate, and a transmission transistor (not shown) and charge storages 155*a*, 155*b*, and 155*c* are integrated therein.

Metal wires (not shown) and pads (not shown) are formed on the semiconductor substrate 110, and the lower insulation layer 60 is formed on the metal wires and the pads.

The first device 100*a*, the second device 100*b*, and the third device 100*c* are sequentially formed on the lower insulation layer 60.

Any one of the first, second, and third devices 100*a*, 100*b*, and 100*c* may be the photoelectric devices 100 and 200 (green photoelectric device according to example embodiments) of FIG. 1 or 2, and the other two of them (a red photoelectric device and a blue photoelectric device) may have the same structure as the photoelectric devices 100 and 200, but an active layer 30 therein selectively absorbs light in a red or blue wavelength region to photoelectrically convert the light. Detailed descriptions of the photoelectric devices 100 and 200 are the same as described above. The first electrode 10 or the second electrode 20 of the photoelectric devices 100 and 200, the red photoelectric device and the blue photoelectric device may be connected to the charge storages 155*a*, 155*b*, and 155*c*.

The active layer 30 of the first device 100*a* may selectively absorb light in any one wavelength region of red, blue, or green to photoelectrically convert the light. For example, the first device 100*a* may be a red photoelectric conversion device configured to selectively sense light in a red wavelength region. The first electrode 10 and the second electrode 20 of the first device 100*a* may be electrically connected to the first charge storage 155*a*. A “photoelectric conversion device” may be interchangeably referred to herein as a “photoelectric device.”

The intermediate insulation layer 65 may be formed on the first device 100*a* and the second device 100*b* may be formed on the intermediate insulation layer 65.

The active layer 30 of the second device 100*b* may selectively absorb light in any one wavelength region of red, blue, or green to photoelectrically convert the light. For example, the second device 100*b* may be a green photoelectric conversion device configured to selectively sense light in a green wavelength region. In another example, the second device 100*b* may be a blue photoelectric conversion device configured to selectively sense light in a blue wavelength region. The first electrode 10 and the second electrode 20 of the second device 100*b* may be electrically connected to the second charge storage 155*b*.

The upper insulation layer 80 is formed on the second device 100*b*. The lower insulation layer 60, the intermediate insulation layer 65, and the upper insulation layer 80 have a plurality of through-holes 85*a*, 85*b*, and 85*c* exposing the charge storages 155*a*, 155*b*, and 155*c*.

The third device 100*c* is formed on the upper insulation layer 80. The active layer 30 of the third device 100*c* may selectively absorb light in any one wavelength region of red, blue, and green to photoelectrically convert the light. For example, the third device 100*c* may be a blue photoelectric conversion device configured to selectively sense light in a blue wavelength region. In another example, the third device 100*c* may be a green photoelectric conversion device configured to selectively sense light in a green wavelength region. The first electrode 10 and the second electrode 20 of the third device 100*c* may be electrically connected to the third charge storage 155*c*.

A focusing lens (not shown) may be further formed on the third device 100*c*. The focusing lens may control direction of incident light and gather the light in one region. The focusing lens may have a shape of, for example, a cylinder or a hemisphere, but is not limited thereto.

In the drawing, a structure in which the first device 100*a*, the second device 100*b*, and the third device 100*c* are sequentially stacked is shown, but is not limited thereto, and the stacking order may be variously changed.

As described above, the first device 100*a*, the second device 100*b*, and the third device 100*c* that absorb light in different wavelength regions have a stacked structure, further reducing a size of the image sensor, implementing a down-sized image sensor, and simultaneously increasing sensitivity and reducing a crosstalk.

In the drawing, the green photoelectric device, the blue photoelectric device, and the red photoelectric device are sequentially stacked, but the stack order may be changed without limitation.

The green photoelectric device (G) may be the aforementioned photoelectric device 100 or photoelectric device 200, the blue photoelectric device (B) may include electrodes facing each other and an active layer therebetween and including an organic material selectively absorbing light in a blue wavelength region, and the red photoelectric device (R) may include electrodes facing each other and an active layer therebetween and including an organic material selectively absorbing light in a red wavelength region.

As described above, the green photoelectric device (G) configured to selectively absorb light in a green wavelength region, the blue photoelectric device (B) configured to selectively absorb light in a blue wavelength region, and the red photoelectric device (R) configured to selectively absorb light in a red wavelength region are stacked, and thereby a size of an image sensor may be decreased and a down-sized image sensor may be realized.

Hereinafter, a sensor-embedded display panel having an image sensor (light absorption sensor) embedded therein according to some example embodiments is described.

The sensor-embedded display panel according to some example embodiments may be a display panel capable of performing a display function and a recognition function (e.g., biometric recognition function), and may be an in-cell type display panel in which a sensor performing a recognition function (e.g., biometric recognition function) is embedded in the display panel.

Figure 9:
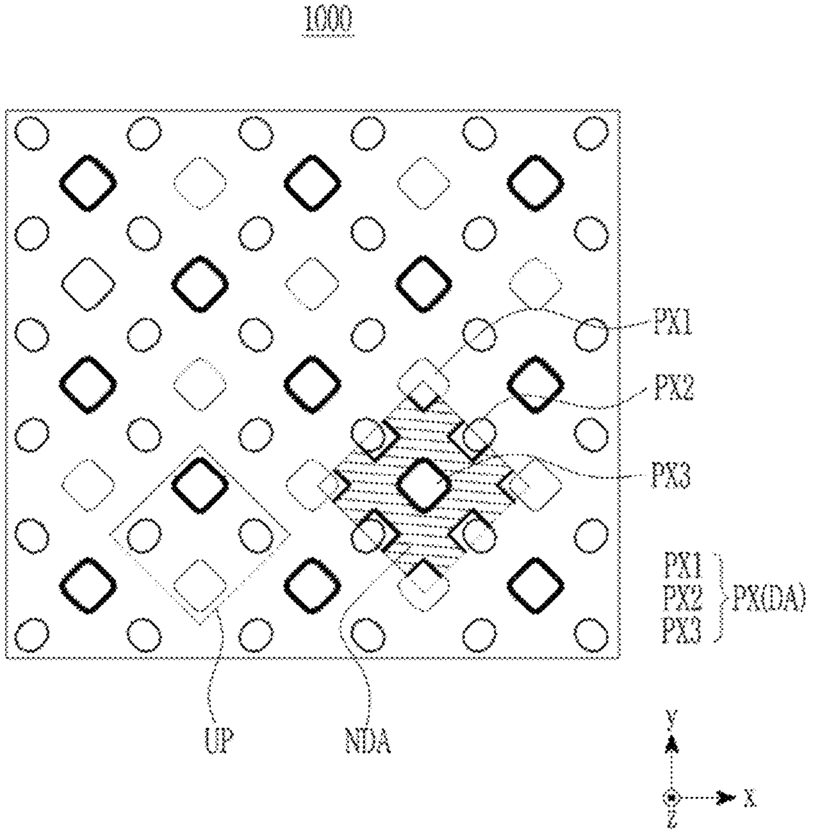
FIG. 9 is a plan view illustrating an example of a sensor-embedded display panel according to some example embodiments.
Figure 10:
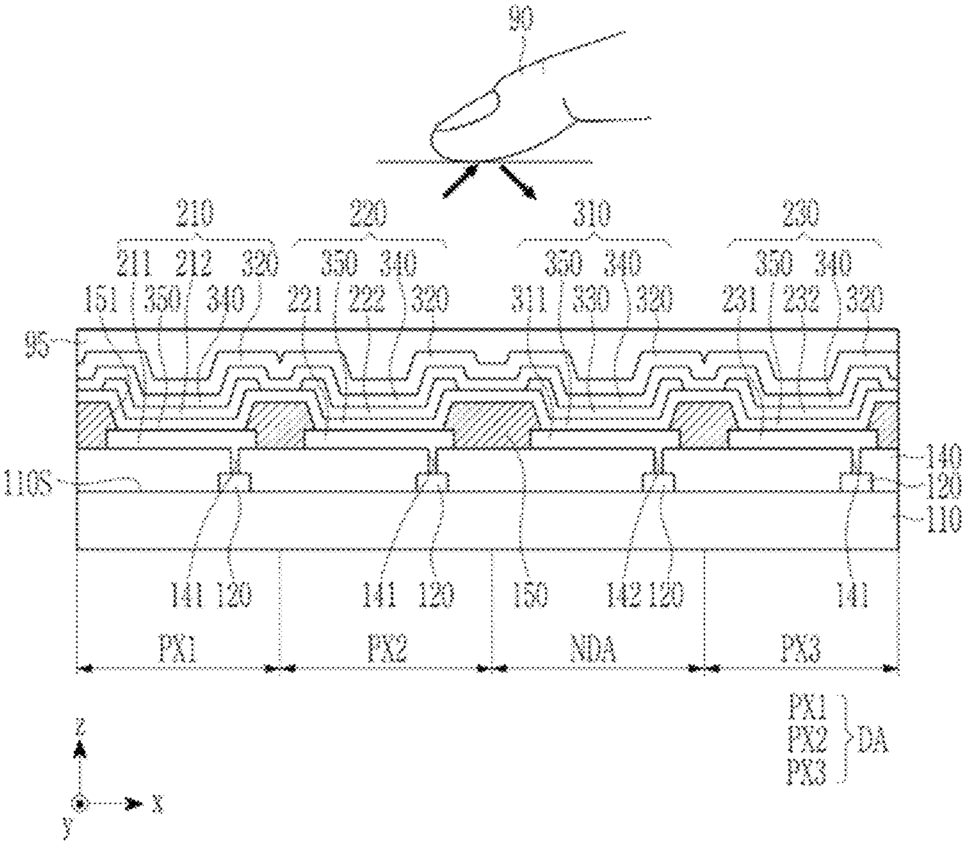
FIG. 10 is a cross-sectional view illustrating an example of a sensor-embedded display panel according to some example embodiments.

FIG. 9 is a plan view illustrating an example of a sensor-embedded display panel according to some example embodiments and FIG. 10 is a cross-sectional view illustrating an example of a sensor-embedded display panel according to some example embodiments.

Referring to FIGS. 9 and 10, a sensor-embedded display panel 1000 according to some example embodiments includes a plurality of subpixels PX’s displaying different colors. The plurality of subpixels PX’s may display at least three primary colors, for example, a first subpixel PX1, a second subpixel PX2, and a third subpixel PX3 displaying different first color, second color, and third color selected from red, green, and blue. For example, the first color, the second color, and the third color may be red, green, and blue, respectively. The first subpixel PX1 may be a red subpixel displaying red, the second subpixel PX2 may be a green subpixel displaying green, and the third subpixel PX3 may be a blue subpixel displaying blue. However, the inventive concepts are not limited thereto, and an auxiliary subpixel (not shown) such as a white subpixel may be further included. Displaying a color may refer to emitting light corresponding to the color (e.g., light in a wavelength spectrum of the color). Referring to FIG. 9, the sensor-embedded display panel 1000 may include a plurality of first subpixels PX1 configured to display a red color (e.g., light of a red wavelength spectrum) and including a first light emitting element (e.g., the first light emitting element 210 shown in FIG. 10), a plurality of second subpixels PX2 configured to display a green color (e.g., light of a green wavelength spectrum) and including a second light emitting element (e.g., the second light emitting element 220 shown in FIG. 10), and a plurality of third subpixels PX3 configured to display a blue color (e.g., light of a blue wavelength spectrum) and including a third light emitting element (e.g., the third light emitting element 230 shown in FIG. 10), where the first subpixels PX1, the second subpixels PX2, and the third subpixels PX3 are located in and/or at least partially define the display area (DA).

The plurality of subpixels PX's including the first subpixel PX1, the second subpixel PX2, and the third subpixel PX3 may constitute (e.g., may define) one unit pixel UP to be arranged repeatedly along the row and/or column. In FIG. 9, a structure including one first subpixel PX1, two second subpixels PX2, and one third subpixel PX3 in the unit pixel UP is illustrated, but the inventive concepts are not limited thereto. At least one first subpixel PX1, at least one second subpixel PX2, and at least one third subpixel PX3 may be included. In the drawing, as an example, an arrangement of a Pentile type is illustrated, but the inventive concepts are not limited thereto. The subpixels PX's may be arranged variously. An area occupied by the plurality of subpixels PX's and displaying colors by the plurality of subpixels PX's may be a display area DA displaying an image. For example, the area (e.g., in the xy plane) of the subpixels (PX) may collectively define the display area (DA) that is configured to display an image thereon (e.g., configured to display one or more colors). A portion of the area (e.g., in the xy plane) of the sensor-embedded display panel 1000 that excludes the display area (DA) (e.g., portions of the area of the sensor-embedded display panel 1000 that are between adjacent subpixels (PX) in the xy direction, xy plane, etc.) may be a non-display area (NDA) that is configured to not display an image thereon (e.g., configured to not display any color).

Each of the first subpixel PX1, the second subpixel PX2, and the third subpixel PX3 may include a light emitting element. As an example, the first subpixel PX1 may include a first light emitting element 210 capable of emitting light of a wavelength spectrum of a first color, the second subpixel PX2 may include a second light emitting element 220 capable of emitting light of a wavelength spectrum of a second color, and the third subpixel PX3 may include a third light emitting element 230 capable of emitting light having a wavelength spectrum of a third color. However, the inventive concepts are not limited thereto, and at least one of the first subpixel PX1, the second subpixel PX2, or the third subpixel PX3 may include a light emitting element that emits light of a combination of a first color, a second color, and a third color, that is, light in a white wavelength spectrum, and may display a first color, a second color, or a third color through a color filter (not shown). Herein, the terms "wavelength spectrum" and "wavelength region" may be used interchangeably.

The sensor-embedded display panel 1000 according to some example embodiments includes the light absorption sensor 310. The light absorption sensor 310 may be disposed in a non-display area NDA. The non-display area NDA may be an area other than the display area DA, in which the first subpixel PX1, the second subpixel PX2, the third subpixel PX3, and optionally auxiliary subpixels are not arranged (e.g., a portion of the total area of the sensor-embedded display panel 1000 that excludes the display area (DA), excludes the subpixels (PX), is between adjacent subpixels (PX), etc.). For example, the area (e.g., in the xy plane) of the subpixels (PX) may collectively define the display area (DA) that is configured to display an image thereon (e.g., configured to display one or more colors). A portion of the area (e.g., in the xy plane) of the sensor-embedded display panel 1000 that excludes the display area (DA) (e.g., portions of the area of the sensor-embedded display panel 1000 that are between adjacent subpixels (PX) in the xy direction, xy plane, etc.) may be a non-display area (NDA) that is configured to not display an image thereon (e.g., configured to not display any color). The light absorption sensor 310 may be disposed between at least two subpixels selected from the first subpixel PX1, the second subpixel PX2, and the third subpixel PX3 (e.g., between at least two subpixels of a first subpixel PX1 of a plurality of first subpixels PX1, a second subpixel PX2 of the plurality of second subpixels PX2, or a third subpixel PX3 of the plurality of third subpixels PX3), and may be disposed in parallel with the first, second, and third light emitting elements 210, 220, and 230 in the display area DA for example in parallel along the in-plane direction of the semiconductor substrate 110 (e.g., the xy direction as shown), which may be a direction extending parallel to an upper surface 110S of the semiconductor substrate 110.

The light absorption sensor 310 may be an optical type recognition sensor (e.g., biometric sensor). The light absorption sensor 310 may absorb light generated by reflection of light emitted from at least one of the first, second, or third light emitting elements 210, 220, or 230 disposed in the display area DA, by a recognition target 90 such as a living body, a tool, or a thing (e.g., may be configured to absorb light of a red wavelength spectrum, a green wavelength spectrum, a blue wavelength spectrum, an infrared wavelength spectrum, or any combination thereof), and then may convert it (the absorbed light) into an electrical signal. Herein, the living body may be a finger, a fingerprint, a palm, an iris, a face, and/or a wrist, but is not limited thereto. The light absorption sensor 310 may be, for example, a fingerprint sensor, an illumination sensor, an iris sensor, a distance sensor, a blood vessel distribution sensor, and/or a heart rate sensor, but is not limited thereto.

The light absorption sensor 310 may be disposed on the semiconductor substrate 110 on the same plane as the first, second, and third light emitting elements 210, 220, and 230, and may be embedded in the sensor-embedded display panel 1000. Restated, the light absorption sensor 310 may be in parallel with the first, second, and third light emitting elements 210, 220, and 230 on the semiconductor substrate 110 along an in-plane direction of the semiconductor substrate 110. As described herein, the in-plane direction of the semiconductor substrate 110 may be a direction (e.g., the xy direction as shown) that extends in parallel with at least a portion of the semiconductor substrate 110, including an upper surface 110S of the semiconductor substrate 110.

Referring to FIG. 10, the sensor-embedded display panel 1000 includes a semiconductor substrate 110; a thin film transistor 120 disposed on the semiconductor substrate 110; an insulation layer 140 disposed on thin film transistor 120; a pixel definition layer 150 disposed on the insulation layer 140; and first, second, or third light emitting elements 210, 220, and 230 and the light absorption sensor 310 disposed in a space partitioned by the pixel definition layer 150.

The semiconductor substrate 110, also referred to herein as a substrate, may be a light-transmitting substrate, for example, a glass substrate or a polymer substrate. The polymer substrate may include, for example, polycarbonate, polymethylmethacrylate, polyethyleneterephthalate, polyethylenenaphthalate, polyimide, polyamide, polyamideimide, polyethersulfone, polyorganosiloxane, styrene-ethylene-butylene-styrene, polyurethane, polyacryl, polyolefin, or any combination thereof, but is not limited thereto.

A plurality of thin film transistors 120 are formed on the semiconductor substrate 110. One or more thin film transistor 120 may be included in each subpixel PX, and may include, for example, at least one switching thin film transistor and/or at least one driving thin film transistor. The semiconductor substrate 110 on which the thin film transistor 120 is formed may be referred to as a thin film transistor substrate (TFT substrate) or a thin film transistor backplane (TFT backplane).

The insulation layer 140 may cover the semiconductor substrate 110 and the thin film transistor 120 and may be formed on the whole surface of the semiconductor substrate 110. The insulation layer 140 may be a planarization layer or a passivation layer, and may include an organic insulating material, an inorganic insulating material, an organic-inorganic insulating material, or any combination thereof. The insulation layer 140 may have a plurality of contact holes 141 for connecting the first, second, and third light emitting elements 210, 220, and 230 and the thin film transistor 120 and a plurality of contact holes 142 for electrically connecting the light absorption sensor 310 and the thin film transistor 120. The insulation layer 140 may include an organic, inorganic, or organic-inorganic insulating material, in some example embodiments, an inorganic insulating material such as silicon oxide, silicon nitride, silicon oxynitride, aluminum oxide, aluminum nitride, or aluminum oxynitride; an organic insulating material such as polyimide, polyamide, polyamideimide, or polyacrylate; or an organic-inorganic insulating material such as polyorganosiloxane or polyorganosilazane.

The pixel definition layer 150 may also be formed on the whole surface of the semiconductor substrate 110 and may be disposed between adjacent subpixels PX's to partition each subpixel PX. The pixel definition layer 150 may have a plurality of openings 151 disposed in each subpixel PX, and in each opening 151, any one of first, second, or third light emitting elements 210, 220, or 230 or the light absorption sensor 310 may be disposed. The pixel definition layer 150 be an insulation layer that may include an organic, inorganic, or organic-inorganic insulating material, in some example embodiments, an inorganic insulating material such as silicon oxide, silicon nitride, or silicon oxynitride; an organic insulating material such as polyimide; or an organic-inorganic insulating material such as polyorganosiloxane or polyorganosilazane.

The first, second and third light emitting elements 210, 220, and 230 are formed on the semiconductor substrate 110 (or thin film transistor substrate), and are repeatedly arranged along the plane direction (e.g., xy direction) of the semiconductor substrate 110 (also referred to as an in-plane direction of the semiconductor substrate 110). As described above, the first, second, and third light emitting elements 210, 220, and 230 may be included in the first subpixel PX1, the second subpixel PX2, and the third subpixel PX3, respectively. The first, second, and third light emitting elements 210, 220, and 230 may be electrically connected to separate thin film transistors 120 and may be driven independently.

The first, second and third light emitting elements 210, 220, and 230 may each independently emit one light selected from a red wavelength spectrum, a green wavelength spectrum, a blue wavelength spectrum, an infrared wavelength spectrum, and any combination thereof. For example, the first light emitting element 210 may emit light of a red wavelength spectrum, the second light emitting element 220 may emit light of a green wavelength spectrum, and the third light emitting element 230 may emit light of a blue wavelength spectrum. Herein, the red wavelength spectrum, the green wavelength spectrum, and the blue wavelength spectrum may have a maximum emission wavelength (Amax) in a wavelength region of greater than about 600 nm and less than about 750 nm, about 500 nm to about 600 nm, and greater than or equal to about 400 nm and less than about 500 nm, respectively.

The first, second, and third light emitting elements 210, 220, and 230 may be, for example, light emitting diodes, for example, an organic light emitting diode including an organic material.

The light absorption sensor 310 may be formed on the semiconductor substrate 110 (or the thin film transistor substrate), and may be randomly or regularly arranged along the plane direction (e.g., xy direction) of the semiconductor substrate 110. As described above, the light absorption sensor 310 may be disposed in the non-display area NDA, and may be connected to a separate thin film transistor 120 to be independently driven. The light absorption sensor 310 may absorb light of the same wavelength spectrum as the light emitted from at least one of the first, second, or third light emitting elements 210, 220, or 230 to convert it (the absorbed light) into an electrical signal. For example, it may absorb light of a red wavelength spectrum, a green wavelength spectrum, a blue wavelength spectrum, an infrared wavelength spectrum, or any combination thereof to convert it into an electrical signal. The light absorption sensor 310 may be, for example, a photoelectric diode, for example, an organic photoelectric diode including an organic material.

Each of the first, second, and third light emitting elements 210, 220, and 230 and the light absorption sensor 310 may include separate, respective pixel electrodes 211, 221, 231, and 311; a separate portion of a common electrode 320 facing the pixel electrodes 211, 221, 231, and 311 and to which a common voltage is applied; and separate, respective light emitting layers 212, 222, and 232 or a light absorbing layer 330, a separate portion of a first common auxiliary layer 340, and a separate portion of a second common auxiliary layer 350 between the pixel electrodes 211, 221, 231, and 311 and the common electrode 320.

The first, second, and third light emitting elements 210, 220, and 230 and the light absorption sensor 310 may be arranged in parallel along the plane direction (e.g., xy direction) of the semiconductor substrate 110, and the common electrode 320, the first common auxiliary layer 340, and the second common auxiliary layer 350 which are formed on the whole surface may be shared. For example, as shown in at least FIG. 10, the light absorbing layer 330 of the light absorption sensor 310 and the light emitting layers 212, 222, and 232 of the first, second, and third light emitting elements 210, 220, and 230 may at least partially overlap with each other (e.g., partially or completely overlap each other) in the in-plane direction (e.g., xy direction) of the semiconductor substrate 110, which may be understood to be a horizontal direction that extends in parallel to an in-plane direction of the semiconductor substrate 110 as shown in FIG. 10 and/or a horizontal direction that extends in parallel to an upper surface 110S of the semiconductor substrate 110 as shown in FIG. 10, and the light absorbing layer 330 and the light emitting layers 212, 222, and 232 may be at least partially positioned on the same plane (e.g., an xy plane extending in the xy directions that intersects each of the light absorbing layer 330 and the light emitting layers 212, 222, and 232).

The common electrode 320 is continuously formed as a single piece of material that extends on the upper portion of the light emitting layers 212, 222, and 232 and the light absorbing layer 330, and is substantially formed on the whole surface of the semiconductor substrate 110. The common electrode 320 may apply a common voltage to the first, second, and third light emitting elements 210, 220, and 230 and the light absorption sensor 310. As shown, the first, second, and third light emitting elements 210, 220, and 230 and the light absorption sensor 310 may include separate portions of a single common electrode 320 that is a single piece of material that extends on each of the respective light emitting layers 212, 222, and 232 and the light absorbing layer 330 and between the first, second, and third light emitting elements 210, 220, and 230 and the light absorption sensor 310.

The first common auxiliary layer 340 is disposed between the light emitting layers 212, 222, and 232 and light absorbing layer 330 and the common electrode 320 and may be continuously formed as a single piece of material that extends on the upper portions of the light emitting layers 212, 222, and 232 and the light absorbing layer 330 and on the lower portions of the common electrode 320. As shown, the first, second, and third light emitting elements 210, 220, and 230 and the light absorption sensor 310 may include separate portions of a single first common auxiliary layer 340 that is a single piece of material that extends on each of the respective light emitting layers 212, 222, and 232 and the light absorbing layer 330 and between the first, second, and third light emitting elements 210, 220, and 230 and the light absorption sensor 310.

The first common auxiliary layer 340 is a charge auxiliary layer (e.g., electron auxiliary layer) that facilitates injection and/or movement of charges (e.g., electrons) from the common electrode 320 to the light emitting layers 212, 222, and 232. For example, the LUMO energy level of the first common auxiliary layer 340 may be disposed between the LUMO energy levels of the light emitting layers 212, 222, and 232 and the work function of the common electrode 320, and the work function of the common electrode 320, the LUMO energy level of the first common auxiliary layer 340, and the LUMO energy levels of the light emitting layers 212, 222, and 232 may become shallow in sequence. On the other hand, the LUMO energy level of the first common auxiliary layer 340 may be shallower than the LUMO energy level of the light absorbing layer 330 and the work function of the common electrode 320, respectively.

The first common auxiliary layer 340 may include an organic material, an inorganic material, an organic-inorganic material, or any combination thereof satisfying the LUMO energy level, for example a halogenated metal such as LiF, NaCl, CsF, RbCl, and RbI; a lanthanide metal such as Yb; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (beryllium bis (benzoquinolin-10-olate), ADN (9,10-di(naphthalene-2-yl) anthracene), BmPyPhB (1,3-bis[3,5-di(pyridin-3-yl)phenyl] benzene), or any combination thereof, but is not limited thereto. The first common auxiliary layer 340 may be one layer or two or more layers.

The second common auxiliary layer 350 may be disposed between the light emitting layers 212, 222, and 232 and the light absorbing layer 330 and the semiconductor substrate 110, and may be disposed between the light emitting layers 212, 222, and 232 and the light absorbing layer 330 and the pixel electrodes 211, 221, 231, and 311. The second common auxiliary layer 350 may be continuously formed as a single piece of material that extends on the lower portions of the light emitting layers 212, 222, and 232 and the light absorbing layer 330 and on the upper portions of pixel electrodes 211, 221, 231, and 311. As shown, the first, second, and third light emitting elements 210, 220, and 230 and the light absorption sensor 310 may include separate portions of a single second common auxiliary layer 350 that is a single piece of material that extends under each of the respective light emitting layers 212, 222, and 232 and the light absorbing layer 330 and between the first, second, and third light emitting elements 210, 220, and 230 and the light absorption sensor 310.

The second common auxiliary layer 350 is a charge auxiliary layer (e.g., hole auxiliary layer) that facilitates injection and/or movement of charges (e.g., holes) from the pixel electrodes 211, 221, and 231 to the light emitting layers 212, 222, and 232. For example, the HOMO energy level of the second common auxiliary layer 350 may be disposed between the HOMO energy level of the light emitting layers 212, 222, and 232 and the work functions of the pixel electrodes 211, 221, and 231, and the work functions of the pixel electrodes 211, 221, and 231, the HOMO energy level of the second common auxiliary layer 350, and the HOMO energy levels of the light emitting layers 212, 222, and 232 may be sequentially deepened.

The second common auxiliary layer 350 may include an organic material, an inorganic material, an organic-inorganic material, or any combination thereof satisfying the HOMO energy level, for example a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris(N-(2-naphthyl)-N-phenylamino)-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-1-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h]quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalene-I-yl)-N,N'-diphenyl-benzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto. The second common auxiliary layer 350 may be one layer or two or more layers.

Each of the first, second, and third light emitting elements 210, 220, 230, and the light absorption sensor 310 includes a separate pixel electrode 211, 221, 231, or 311 facing the common electrode 320. One of the pixel electrodes 211, 221, 231, and 311 or the common electrode 320 is an anode and the other is a cathode. For example, the pixel electrodes 211, 221, 231, and 311 may be an anode and the common electrode 320 may be a cathode. The pixel electrodes 211, 221, 231, and 311 are separated for each subpixel PX, and may be electrically connected to a separate thin film transistor 120 to be independently driven.

The pixel electrodes 211, 221, 231, and 311 and the common electrode 320 may each be a light-transmitting electrode or a reflective electrode, and for example, at least one of the pixel electrodes 211, 221, 231, and 311 or the common electrode 320 may be a light-transmitting electrode.

The light-transmitting electrode may be a transparent electrode or a semi-transmissive electrode. The transparent electrode may have a light transmittance of greater than or equal to about 85%, greater than or equal to about 90%, or greater than or equal to about 95% and the semi-transmissive electrode may have a light transmittance of greater than or equal to about 30% and less than about 85%, about 40% to about 80%, or about 40% to about 75%. The transparent electrode and the semi-transmissive electrode may include, for example, at least one of an oxide conductor, a carbon conductor, or a metal thin film. The oxide conductors may include, for example, one or more selected from indium tin oxide (ITO), indium zinc oxide (IZO), zinc tin oxide (ZTO), aluminum tin oxide (ATO), and aluminum zinc oxide (AZO), the carbon conductor may include one or more selected from graphene and carbon nanostructures, and the metal thin film may be a very thin film including aluminum (AI), magnesium (Mg), silver (Ag), gold (Au), magnesium-silver (Mg—Ag), magnesium-aluminum (Mg-AI), an alloy thereof, or any combination thereof.

The reflective electrode may include a reflective layer having a light transmittance of less than or equal to about 5% and/or a reflectance of greater than or equal to about 80%, and the reflective layer may include an optically opaque material. The optically opaque material may include a metal, a metal nitride, or any combination thereof, for example silver (Ag), copper (Cu), aluminum (Al), gold (Au), titanium (Ti), chromium (Cr), nickel (Ni), an alloy thereof, a nitride thereof (e.g., TiN), or any combination thereof, but is not limited thereto. The reflective electrode may be formed of a reflective layer or may have a stacked structure of a reflective layer/transmissive layer or a transmissive layer/reflective layer/transmissive layer, and the reflective layer may be one layer or two or more layers.

For example, when the pixel electrodes 211, 221, 231, and 311 are light-transmitting electrodes and the common electrode 320 is a reflective electrode, the sensor-embedded display panel 1000 may be a bottom emission type display panel that emits light toward the semiconductor substrate 110. For example, when the pixel electrodes 211, 221, 231, and 311 are reflective electrodes and the common electrode 320 are light-transmitting electrode, the sensor-embedded display panel 1000 may be a top emission type display panel that emits light to the opposite side of the semiconductor substrate 110. For example, when the pixel electrodes 211, 221, 231, and 311 and the common electrode 320 are light-transmitting electrodes, respectively, the sensor-embedded display panel 1000 may be a both side emission type display panel.

For example, the pixel electrodes 211, 221, 231, and 311 may be reflective electrodes and the common electrode 320 may be a semi-transmissive electrode. In this case, the sensor-embedded display panel 1000 may have a microcavity structure. In the microcavity structure, reflection may occur repeatedly between the reflective electrode and the semi-transmissive electrode separated by a particular (or, alternatively, predetermined) optical length (e.g., a distance between the semi-transmissive electrode and the reflective electrode) and light of a particular (or, alternatively, predetermined) wavelength spectrum may be enhanced to improve optical properties.

For example, among the light emitted from the light emitting layers 212, 222, and 232 of the first, second, and third light emitting elements 210, 220, and 230, light of a particular (or, alternatively, predetermined) wavelength spectrum may be repeatedly reflected between the semi-transmissive electrode and the reflective electrode and then may be modified. Among the modified light, light having a wavelength spectrum corresponding to a resonance wavelength of a microcavity may be enhanced to exhibit amplified light emission characteristics in a narrow wavelength region. Accordingly, the sensor-embedded display panel 1000 may express colors with high color purity.

For example, among the light incident on the light absorption sensor 310, light of a particular (or, alternatively, predetermined) wavelength spectrum may be repeatedly reflected between the semi-transmissive electrode and the reflective electrode to be modified. Among the modified light, light having a wavelength spectrum corresponding to the resonance wavelength of a microcavity may be enhanced to exhibit photoelectric conversion characteristics amplified in a narrow wavelength region. Accordingly, the light absorption sensor 310 may exhibit high photoelectric conversion characteristics in a narrow wavelength region.

Each of the first, second, and third light emitting elements 210, 220, and 230 includes light emitting layers 212, 222, and 232 between the pixel electrodes 211, 221, and 231 and the common electrode 320. Each of the light emitting layer 212 included in the first light emitting element 210, the light emitting layer 222 included in the second light emitting element 220, and the light emitting layer 232 included in the third light emitting element 230 may emit light in the same or different wavelength spectra and may emit light in, for example a red wavelength spectrum, a green wavelength spectrum, a blue wavelength spectrum, an infrared wavelength spectrum, or any combination thereof.

For example, when the first light emitting element 210, the second light emitting element 220, and the third light emitting element 230 are a red light emitting elements, a green light emitting element, and a blue light emitting element, respectively, the light emitting layer 212 may be a red light emitting layer that emits light in a red wavelength spectrum, the light emitting layer 222 included in the second light emitting element 220 may be a green light emitting layer that emits light in a green wavelength spectrum, and the light emitting layer 232 included in the third light emitting element 230 may be a blue light emitting layer that emits light in a blue wavelength spectrum. Herein, the red wavelength spectrum, the green wavelength spectrum, and the blue wavelength spectrum may have a maximum emission wavelength in a wavelength region of greater than or equal to about 600 nm and less than about 750 nm, about 500 nm to about 600 nm, and greater than or equal to about 400 nm and less than about 500 nm, respectively.

For example, when at least one of the first light emitting element 210, the second light emitting element 220, or the third light emitting element 230 is a white light emitting element, the light emitting layer of the white light emitting element may emit light of a full visible light wavelength spectrum, for example, light in a wavelength spectrum of greater than or equal to about 380 nm and less than about 750 nm, about 400 nm to about 700 nm, or about 420 nm to about 700 nm.

The light emitting layers 212, 222, and 232 may include at least one host material and a fluorescent or phosphorescent dopant, and at least one of the at least one host material or the fluorescent or phosphorescent dopant may be an organic material. The organic material may include, for example, a low molecular weight organic material, such as a depositable organic material.

For example, the light emitting layers 212, 222, and 232 may include perylene; rubrene; 4-(dicyanomethylene)-2-methyl-6-[p-(dimethylamino)styryl]-4H-pyran; coumarin or a derivative thereof; carbazole or a derivative thereof; TPBi (2,2',2"-(1,3,5-benzinetriyl)-tris(1-phenyl-1-H-benzimidazole); TBADN (2-t-butyl-9,10-di(naphth-2-yl)anthracene); AND (9,10-di(naphthalene-2-yl)anthracene); CBP (4,4'-bis(N-carbazolyl)-1,1'-biphenyl); TCTA (4,4',4"-tris(carbazol-9-yl)-triphenylamine); TPBi (1,3,5-tris(N-phenylbenzimidazol-2-yl)benzene); TBADN (3-tert-butyl-9,10-di(naphth-2-yl)anthracene); DSA (distyrylarylene); CDBP (4,4'-bis(9-carbazolyl)-2,2'-dimethylbiphenyl); MADN (2-methyl-9,10-bis(naphthalen-2-yl)anthracene); TCP (1,3,5-tris(carbazol-9-yl)benzene); Alq3 (tris(8-hydroxyquinolino)lithium); an organometallic compound including Pt, Os, Ti, Zr, Hf, Eu, Tb, Tm, Rh, Ru, Re, Be, Mg, Al, Ca, Mn, Co, Cu, Zn, Ga, Ge, Pd, Ag, and/or Au; a derivative thereof; or any combination thereof, but is not limited thereto.

The first, second, and third light emitting elements 210, 220, and 230 may be, for example, a quantum dot light emitting diode including quantum dots, or a perovskite light emitting diode including perovskite.

The quantum dot may include, for example, a Group II-VI semiconductor compound, a Group III-V semiconductor compound, a Group IV-VI semiconductor compound, a Group IV semiconductor element or compound, a Group 1-III-VI semiconductor compound, a Group I-II-IV-VI semiconductor compound, a Group II-Ill-V semiconductor compound, or any combination thereof. The Group II-IV semiconductor compound may be, for example, selected from a binary element semiconductor compound selected from CdSe, CdTe, ZnS, ZnSe, ZnTe, ZnO, HgS, HgSe, HgTe, MgSe, MgS, or a mixture thereof; a ternary element semiconductor compound selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, or a mixture thereof; and a quaternary element semiconductor compound selected from HgZnTeS, CdZnSeS, CdZnSeTe, CdZnSTe, CdHgSeS, CdHgSeTe, CdHgSTe, HgZnSeS, HgZnSeTe, HgZnSTe, or a mixture thereof, but is not limited thereto. The Group III-V semiconductor compound may be, for example, selected from a binary element semiconductor compound selected from GaN, GaP, GaAs, GaSb, AlN, AlP, AlAs, AlSb, InN, InP, InAs, InSb, or a mixture thereof; a ternary element semiconductor compound selected from GaNP, GaNAs, GaNSb, GaPAs, GaPSb, AlNP, AlNAs, AlNSb, AlPAs, AlPSb, InNP, InNAs, InNSb, InPAs, InPSb, or a mixture thereof; and a quaternary element semiconductor compound selected from GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, or a mixture thereof, but is not limited thereto. The Group IV-VI semiconductor compound may be, for example, selected from a binary element semiconductor compound selected from SnS, SnSe, SnTe, PbS, PbSe, PbTe, or a mixture thereof; a ternary element semiconductor compound selected from SnSeS, SnSeTe, SnSTe, PbSeS, PbSeTe, PbSTe, SnPbS, SnPbSe, SnPbTe, or a mixture thereof; and a quaternary element semiconductor compound selected from SnPbSSe, SnPbSeTe, SnPbSTe, or a mixture thereof, but is not limited thereto. The Group IV semiconductor element or compound may be, for example, selected from a semiconductor element such as Si, Ge, or a mixture thereof; and a binary element compound selected from SiC, SiGe, or a mixture thereof, but is not limited thereto. The Group I-III-VI semiconductor compound may be, for example, $CuInSe_2$, $CuInS_2$, CuInGaSe, CuInGaS, or a mixture thereof, but is not limited thereto. The Group I-II-IV-VI semiconductor compound may be, for example, CuZnSnSe, CuZnSnS, or a mixture thereof, but is not limited thereto. The Group II-III-V semiconductor compound may be, for example, InZnP, but is not limited thereto.

The perovskite may be $CH_3NH_3PbBr_3$, $CH_3NH_3PbI_3$, $CH_3NH_3SnBr_3$, $CH_3NH_3SnI_3$, $CH_3NH_3Sn_{1x}Pb_xBr_3$, $CH_3NH_3Sn_{1x}Pb_xI_3$, $HC(NH_2)_2PbI_3$, $HC(NH_2)_2SnI_3$, $(C_4H_9NH_3)_2PbBr_4$, $(C_6H_5CH_2NH_3)_2PbBr_4$, $(C_6H_5CH_2NH_3)_2PbI_4$, $(C_6H_5C_2H_4NH_3)_2PbBr_4$, $(C_6H_{13}NH_3)_2(CH_3NH_3)_{n1}PbnI_{3n+1}$ (x, n, 1x, and n1 being any positive integer), or any combination thereof, but is not limited thereto.

The light absorption sensor 310 includes a light absorbing layer 330 between the pixel electrode 311 and the common electrode 320. The light absorbing layer 330 is disposed in parallel with the light emitting layers 212, 222, and 232 of the first, second, and third light emitting elements 210, 220, and 230 along the plane direction (e.g., xy direction) of the semiconductor substrate 110. The light absorbing layer 330 and the light emitting layers 212, 222, and 232 may be disposed on the same plane.

The light absorbing layer 330 may absorb light of a particular (or, alternatively, predetermined) wavelength spectrum and convert it into an electrical signal. The light absorbing layer 330 may absorb light generated by reflection of the aforementioned light emitted from at least one of the first, second, or third light emitting elements 210, 220, or 230, by the recognition target 90 and may convert it into an electrical signal. The light absorbing layer 330 may absorb light of a red wavelength spectrum, a green wavelength spectrum, a blue wavelength spectrum, an infrared wavelength spectrum, or any combination thereof.

For example, the light absorbing layer 330 may selectively absorb light of a red wavelength spectrum having a maximum absorption wavelength belonging to greater than about 600 nm and less than about 750 nm, and may absorb light generated by reflection of the light emitted from the red light emitting element among the first, second, and third light emitting elements 210, 220, and 230, by the recognition target 90.

For example, the light absorbing layer 330 may selectively absorb light of a green wavelength spectrum having a maximum absorption wavelength belonging to about 500 nm to about 600 nm, and may absorb light generated by reflection of the light emitted from the green light emitting element among the first, second and third light emitting elements 210, 220, and 230, by the recognition target 90.

For example, the light absorbing layer 330 may selectively absorb light in a blue wavelength spectrum having a maximum absorption wavelength belonging to greater than or equal to about 380 nm and less than about 500 nm, and may absorb light generated by reflection of the light emitted from the blue light emitting element among the first, second, and third light emitting elements 210, 220, and 230, by the recognition target 90.

For example, the light absorbing layer 330 may absorb light of a red wavelength spectrum, a green wavelength spectrum, and a blue wavelength spectrum, that is, light of a full visible wavelength spectrum of greater than or equal to about 380 nm and less than about 750 nm. The light absorbing layer 330 may absorb light generated by reflection of a combination of light emitted from the light emitting elements 210, 220, and 230, by the recognition target 90.

The light absorbing layer 330 may include a p-type semiconductor and/or an n-type semiconductor for photoelectric conversion of the absorbed light. The p-type semiconductor and the n-type semiconductor may form a pn junction, generate excitons by receiving light from the outside, and then separate the generated excitons into holes and electrons. Each of the p-type semiconductor and the n-type semiconductor may be one or two or more, and one of the p-type semiconductor or the n-type semiconductor may be the compound represented by Chemical Formula 1.

In example embodiments, the light absorbing layer 330 may include the compound represented by Chemical Formula 1 as an n-type semiconductor and the compound represented by Chemical Formula 7 as a p-type semiconductor.

The p-type semiconductor may be represented by Chemical Formula 7A or Chemical Formula 7B.

In example embodiments, the light absorbing layer 330 includes the compound represented by Chemical Formula 1 as a p-type semiconductor, and includes fullerene, a fullerene derivative, subphthalocyanine or a subphthalocyanine derivative, thiophene or a thiophene derivative, or a compound represented by Chemical Formula 8 as a n-type semiconductor. These are as described above.

The light absorbing layer 330 may be disposed in parallel with the light emitting layers 212, 222, and 232 along the plane direction (e.g., xy direction) of the semiconductor substrate 110 as described above, and may be disposed on the same plane as the light emitting layers 212, 222, and 232.

The compound represented by Chemical Formula 1 may have an energy level capable of forming effective electrical matching with the first common auxiliary layer 340 as a p-type semiconductor or an n-type semiconductor of the light absorbing layer 330. For example, a difference between the LUMO energy level of the first common auxiliary layer 340 and the LUMO energy level of the compound may be less than or equal to about 1.2 eV, and within the above range, less than or equal to about 1.1 eV, less than or equal to about 1.0 eV, less than or equal to about 0.8 eV, less than or equal to about 0.7 eV, less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, charges (e.g., electrons) generated in the light absorbing layer 330 may pass through the first common auxiliary layer 340 and may be effectively moved and/or extracted to the common electrode 320.

The light absorbing layer 330 may be an intrinsic layer (I layer) in which a p-type semiconductor and the n-type semiconductor are mixed in a bulk heterojunction form. In this case, the p-type semiconductor and the n-type semiconductor may be mixed in a volume ratio (thickness ratio) of about 1:9 to about 9:1, and within the above range, for example, about 2:8 to about 8:2, about 3:7 to about 7:3, about 4:6 to about 6:4, or about 5:5. By having the volume ratio in the above range, an exciton may be effectively produced, and a pn junction may be effectively formed.

The light absorbing layer 330 may include a p-type layer and/or an n-type layer instead of the intrinsic layer (I layer) or further include a p-type layer and/or an n-type layer on and/or under the intrinsic layer (I layer). The p-type layer may include, for example, a p-type semiconductor and the n-type layer may include an n-type semiconductor. The light absorbing layer 330 may be, for example, an l layer, a p-type layer/n-type layer, a p-type layer/I layer, an l layer/n-type layer, or a p-type layer/I layer/n-type layer, but is not limited thereto.

The light emitting layers 212, 222, and 232 and the light absorbing layer 330 may each independently have a thickness of about 5 nm to about 300 nm, which may be about 10 nm to about 250 nm, about 20 nm to about 200 nm, or about 30 nm to about 180 nm within the above range. The difference between the thicknesses of the light emitting layers 212, 222, and 232 and the light absorbing layer 330 may be less than or equal to about 20 nm, within the above range, less than or equal to about 15 nm, less than or equal to about 10 nm, or less than or equal to about 5 nm. The light emitting layers 212, 222, and 232 and the light absorbing layer 330 may substantially have the same thickness.

An encapsulation layer 95 may be formed on the first, second, and third light emitting elements 210, 220, and 230 and the light absorption sensor 310. The encapsulation layer 95 may include, for example, a glass plate, a metal thin film, an organic film, an inorganic film, an organic-inorganic film, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, oxides, nitrides and/or oxynitrides, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 95 may have one or two or more layers.

As described above, the sensor-embedded display panel 1000 according to some example embodiments, including the example embodiments shown in FIGS. 9 and 10 includes the first, second, and third light emitting elements 210, 220, and 230 for displaying colors by emitting light of a particular (or, alternatively, predetermined) wavelength spectrum, and the light absorption sensor 310 that absorbs the light generated by reflection of the light by the recognition target 90 and converts it into an electrical signal in the same plane on the semiconductor substrate 110, and thereby the display function and the recognition function (e.g., biometric recognition function) may be performed together. Accordingly, high performance slim-type sensor-embedded display panel 1000 may be implemented without increasing the thickness, unlike the conventional display panel in which a sensor is manufactured as a separate module and then is attached to the outside of the display panel or formed on the lower portion of the display panel.

In addition, since the light absorption sensor 310 uses the light emitted from the first, second, and third light emitting elements 210, 220, and 230, a recognition function (e.g., a biometric recognition function) may be performed without a separate light source. Therefore, since there is no need to provide a separate light source outside the display panel, it is possible to prevent a decrease of the aperture ratio of the display panel due to the area occupied by the light source, and at the same time to save the power consumed by the separate light source, improving power consumption of the sensor-embedded display panel 1000.

In addition, as described above, the first, second, and third light emitting elements 210, 220, and 230 and the light absorption sensor 310 share the common electrode 320, the first common auxiliary layer 340, and the second common auxiliary layer 350, and thereby the structure and process may be simplified compared with the case of forming the first, second, and third light emitting elements 210, 220, and 230 and the light absorption sensor 310 through separate processes.

In addition, as described above, the light absorption sensor 310 may be an organic photoelectric diode including an organic light absorbing layer. Accordingly, it may have a light absorption that is twice or more higher than that of an inorganic diode such as a silicon photodiode and thus may have a high-sensitivity sensing function.

In addition, as described above, the light absorbing layer 330 of the light absorption sensor 310 includes the compound represented by Chemical Formula 1, thereby selectively increasing the sensitivity to light in the green wavelength spectrum and improving color separation characteristics without mixing the absorption spectrum. Accordingly, the sensor-embedded display panel 1000 may additionally implement an anti-spoofing effect in addition to the aforementioned effect, and thus the color separation characteristics of the light reflected by the recognition target 90 may be improved, thereby further increasing the detail of the shape of the recognition target 90 and the color of the reflected light (e.g., skin color) may be selectively recognized, thereby further enhancing the accuracy of the biometric recognition function.

In addition, as described above, the organic material included in the light absorbing layer 330 of the light absorption sensor 310 has a sublimation temperature difference within a particular (or, alternatively, predetermined) range with the organic materials of the light emitting layers 212, 222, and 232 of the first, second and third light emitting elements 210, 220, and 230, and thus deposition may be performed in the same process, thereby simplifying the process and increasing process stability.

Also, as described above, since the light absorption sensor 310 may be disposed anywhere in the non-display area NDA (e.g., anywhere in a portion of the sensor-embedded display panel 1000 that does not vertically overlap (e.g., in the z direction) with any light emitting elements and thus is not configured to emit light and/or display color), a desired quantity of the light absorption sensors 310 may be disposed at one or more desired locations in the sensor-embedded display panel 1000. Therefore, for example, by randomly or regularly disposing, arranging, and/or distributing light absorption sensors 310 on the entire area of the sensor-embedded display panel 1000, the biometric recognition function may be performed on any part of the screen of the electronic device such as a mobile device, and the biometric recognition function may be selectively performed at a specific location alone where the biometric recognition function is required according to the user's selection.

Hereinafter, another example of the sensor-embedded display panel 1000 according to some example embodiments is described.

Figure 11:
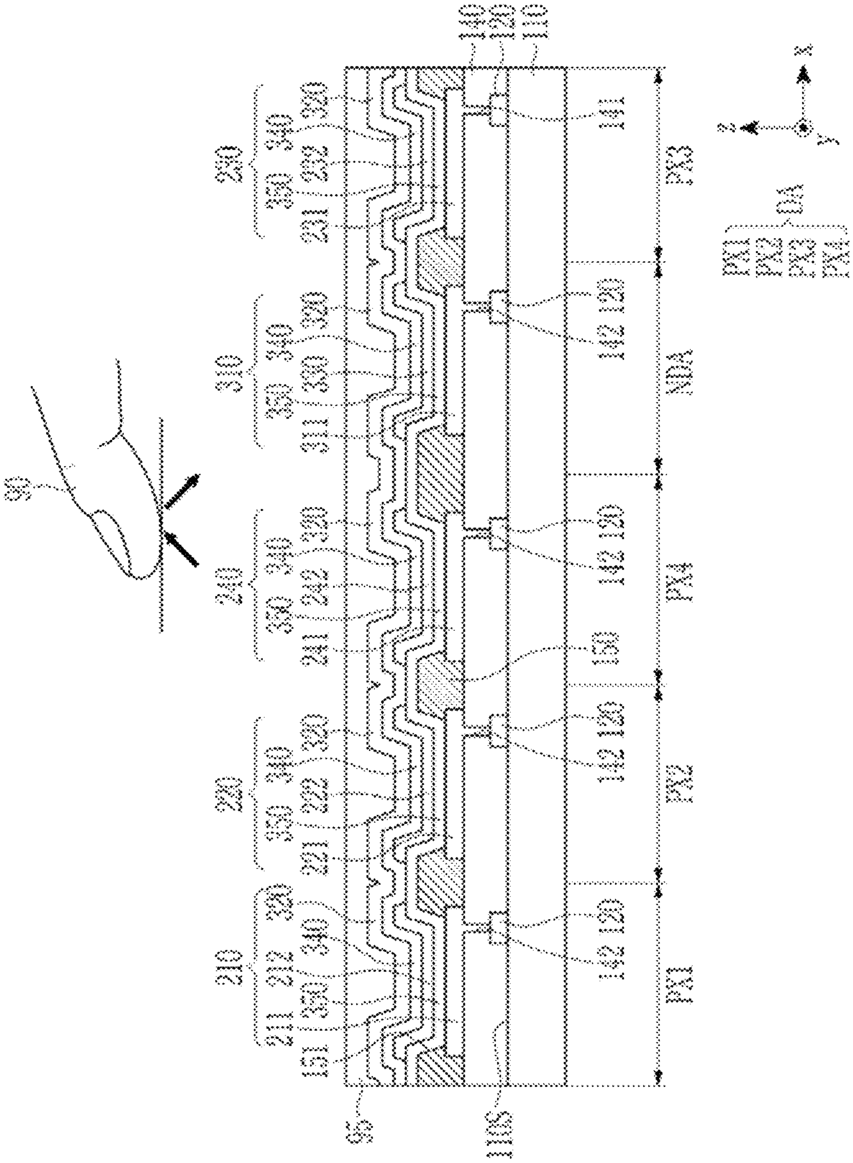
FIG. 11 is a cross-sectional view illustrating another example of a sensor-embedded display panel according to some example embodiments.

FIG. 11 is a cross-sectional view illustrating another example of a sensor-embedded display panel according to some example embodiments.

Referring to FIG. 11, a sensor-embedded display panel 1000 according to some example embodiments includes a plurality of subpixels PX displaying different colors, that is, a first subpixel PX1, a second subpixel PX2, and a third subpixel PX3 displaying a first color, a second color, and a third color selected from red, green, and blue, and the first subpixel PX1, the second subpixel PX2, and the third subpixel PX3 include a first light emitting element 210, a second light emitting element 220, and a third light emitting element 230, respectively, like some example embodiments, including the example embodiments illustrated in FIGS. 9 and 10.

However, unlike some example embodiments, including the example embodiments illustrated in FIGS. 9 and 10, the sensor-embedded display panel 1000 according to some example embodiments may include the fourth light emitting element 240 that emits light in an infrared wavelength spectrum. For example, the fourth light emitting element 240 may be included in the fourth subpixel PX4 adjacent to the first subpixel PX1, the second subpixel PX2, and/or the third subpixel PX3, or may be included in a non-display area, NDA. The fourth subpixel PX4 may form one unit pixel UP together with the first subpixel PX1, the second subpixel PX2, and the third subpixel PX3, and the unit pixel UP may be arranged repeatedly along rows and/or columns.

Descriptions of the first subpixel PX1, the second subpixel PX2, the third subpixel PX3, the first light emitting element 210, the second light emitting element 220, and the third light emitting element 230 are the same as described above.

The fourth light emitting element 240 is disposed on the semiconductor substrate 110 and may be disposed on the same plane as the first, second, and third light emitting elements 210, 220, and 230 and the light absorption sensor 310. For example, as shown in at least FIG. 10, the light absorbing layer 330 of the light absorption sensor 310 and the light emitting layers 212, 222, and 232 of the first, second, and third light emitting elements 210, 220, and 230 may at least partially overlap with each other (e.g., partially or completely overlap each other) in the in-plane direction (e.g., xy direction) of the semiconductor substrate 110, which may be understood to be a horizontal direction that extends in parallel to an in-plane direction of the semiconductor substrate 110 as shown in FIG. 10 and/or a horizontal direction that extends in parallel to an upper surface 110S of the semiconductor substrate 110 as shown in FIG. 10, and the light absorbing layer 330 and the light emitting layers 212, 222, and 232 may be at least partially positioned on the same plane (e.g., an xy plane extending in the xy directions that intersects each of the light absorbing layer 330 and the light emitting layers 212, 222, and 232). The fourth light emitting element 240 may be electrically connected to a separate thin film transistor 120 and driven independently. The fourth light emitting element 240 may have a structure in which the pixel electrode 241, the second common auxiliary layer 350, the light emitting layer 242, the first common auxiliary layer 340, and the common electrode 320 are sequentially stacked. Among them, the common electrode 320, the first common auxiliary layer 340, and the second common auxiliary layer 350 may be shared with the first, second, and third light emitting elements 210, 220, and 230, and the light absorption sensor 310. The light emitting layer 242 may emit light of an infrared wavelength spectrum, which may have for example a maximum emission wavelength in a range of greater than or equal to about 750 nm, about 750 nm to about 20 μm, about 780 nm to about 20 μm, about 800 nm to about 20 μm, about 750 nm to about 15 μm, about 780 nm to about 15 μm, about 800 nm to about 15 μm, about 750 nm to about 10 μm, about 780 nm to about 10 μm, about 800 nm to about 10 μm, about 750 nm to about 5 μm, about 780 nm to about 5 μm, about 800 nm to about 5 μm, about 750 nm to about 3 μm, about 780 nm to about 3 μm, about 800 nm to about 3 μm, about 750 nm to about 2 μm, about 780 nm to about 2 μm, about 800 nm to about 2 μm, about 750 nm to about 1.5 μm, about 780 nm to about 1.5 μm, or about 800 nm to about 1.5 μm.

The light absorption sensor 310 may absorb light generated by reflection of light emitted from at least one of the first, second, third, or fourth light emitting elements 210, 220, 230, or 240, by a recognition target 90 such as a living body or a tool, and then convert it into an electrical signal. For example, the light absorption sensor 310 may absorb light in an infrared wavelength spectrum generated by reflection of light emitted from the fourth light emitting element 240, by the recognition target 90, and then convert it into an electrical signal. In this case, the light absorbing layer 330 of the light absorption sensor 310 may include an organic material, an inorganic material, an organic-inorganic material, or any combination thereof that selectively absorbs light in the infrared wavelength spectrum. For example, the light absorbing layer 330 may include a quantum dot, a quinoid metal complex compound, a polymethine compound, a cyanine compound, a phthalocyanine compound, a merocyanine compound, a naphthalocyanine compound, an immonium compound, a diimmonium compound, a triarylmethane compound, a dipyrromethene compound, an anthraquinone compound, a diquinone compound, a naphthoquinone compound, an anthraquinone compound, a squarylium compound, a rylene compound, a perylene compound, a squaraine compound, a pyrylium compound, a thiopyrylium compound, a diketopyrrolopyrrole compound, a boron dipyrromethene compound, a nickel-dithiol complex compound, a croconium compound, a derivative thereof, or any combination thereof, but is not limited thereto.

The sensor-embedded display panel 1000 according to some example embodiments includes the fourth light emitting element 240 that emits light in the infrared wavelength spectrum and the light absorption sensor 310 that absorbs light in the infrared wavelength spectrum. Therefore, in addition to the recognition function (biometric recognition function), the sensitivity of the light absorption sensor 310 may be improved even in a low-illumination environment, and the detection capability of a 3D image may be further increased by widening a dynamic range for detailed division of black and white contrast. Accordingly, the sensing capability of the sensor-embedded display panel 1000 may be further improved. In particular, since light in the infrared wavelength spectrum may have a deeper penetration depth due to its long wavelength characteristics and information located at different distances may be effectively obtained, images or changes in blood vessels such as veins, iris and/or face, etc., in addition to fingerprints may be effectively detected, and the scope of application may be further expanded.

In some example embodiments, the light absorption sensor 310 may be provided separately from (e.g., independently of) a sensor-embedded display panel 1000 and/or from any light emitting elements, for example as a separate component of an electronic device. For example, an electronic device, such as the electronic device 2000 shown in FIG. 13, may include a plurality of light absorption sensors 310, as a separate at least one additional device 1340, to serve as a camera for the electronic device separately from any light emitting elements and/or display panels of the electronic device 2000.

In some example embodiments, one or both of the first common auxiliary layer 340 and/or the second common auxiliary layer 350 may be absent from the sensor-embedded display panel 1000, and the light absorbing layer 330 may be understood to be between (e.g., directly between) a pair of electrodes (e.g., pixel electrode 211 and a portion of the common electrode 320). In some example embodiments, the common electrode 320 may be replaced by a plurality of separate pixel electrodes that are each included in a separate one of the light emitting elements 210, 220, 230, and/or 240 and/or the light absorption sensor 310 and may face a separate pixel electrode 211, 221, 231, and/or 311, such that the light absorbing layer 330 may be understood to be between (e.g., directly between) a pair of electrodes that include the pixel electrode 311 and a separate electrode included in the light absorption sensor 310.

The aforementioned sensor-embedded display panel 1000 may be applied to (e.g., included in) electronic devices such as various display devices. Electronic devices such as display devices may be applied to, for example, mobile phones, video phones, smart phones, mobile phones, smart pads, smart watches, digital cameras, tablet PCs, laptop PCs, notebook computers, computer monitors, wearable computers, televisions, digital broadcasting terminals, e-books, personal digital assistants (PDAs), portable multimedia player (PMP), enterprise digital assistant (EDA), head mounted display (HMD), vehicle navigation, Internet of Things (IoT), Internet of all things (IoE), drones, door locks, safes, automatic teller machines (ATM), security devices, medical devices, or automotive electronic components, but are not limited thereto.

Figure 12:
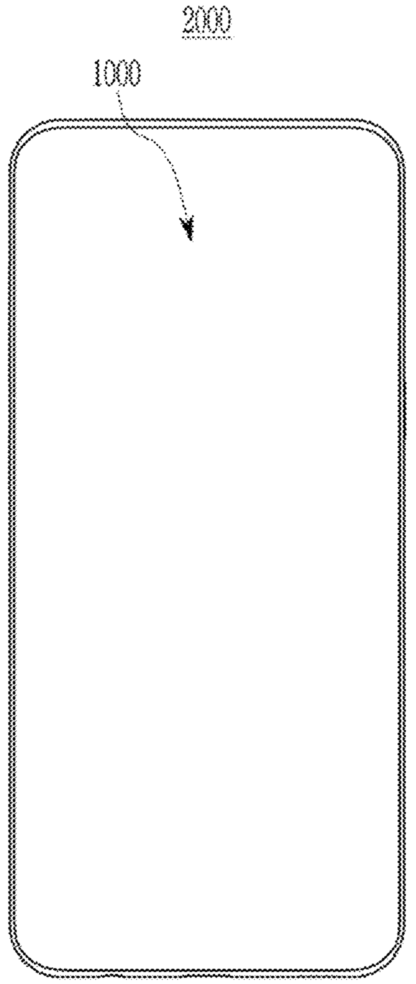
FIG. 12 is a schematic view illustrating an example of a smart phone as an electronic device according to an example.

FIG. 12 is a schematic view illustrating an example of a smart phone as an electronic device according to some example embodiments.

Referring to FIG. 12, the electronic device 2000 may include the aforementioned sensor-embedded display panel 1000, the sensor-embedded display panel 1000 having the light absorption sensor 310 disposed on the whole or a part of its area, and thus a biometric recognition function may be performed on any part of the screen, and according to the user's selection, the biometric recognition function may be selectively performed at a specific location alone where the biometric recognition function is required.

An example of a method of recognizing the recognition target 90 in an electronic device 2000 such as a display device may include, for example, driving the first, second, and third light emitting elements 210, 220, and 230 of the sensor-embedded display panel 1000 (or the first, second, third, and fourth light emitting elements 210, 220, 230, and 240) and the light absorption sensor 310 to detect the light reflected by the recognition target 90 among the light emitted from the first, second, and third light emitting elements 210, 220, and 230 (or the first, second, third and fourth light emitting elements 210, 220, 230, and 240), in the light absorption sensor 310; comparing the image of the recognition target 90 stored in advance with the image of the recognition target 90 detected by the light absorption sensor 310; and judging the consistency of the compared images and if they match according to the determination that recognition of the recognition target 90 is complete, turning off the light absorption sensor 310, permitting user's access to the display device, and driving the sensor-embedded display panel 1000 to display an image.

Figure 13:
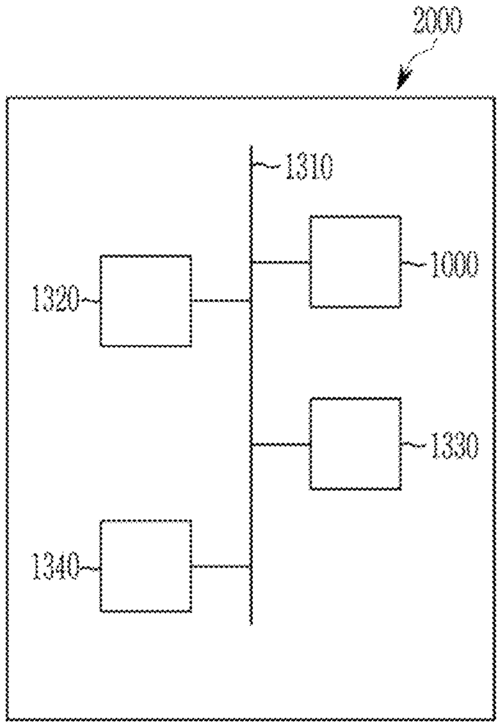
FIG. 13 is a schematic view illustrating an example of a configuration view of an electronic device according to some example embodiments.

FIG. 13 is a schematic view illustrating an example of a configuration diagram of an electronic device according to some example embodiments.

Referring to FIG. 13, in addition to the aforementioned constituent elements (e.g., the sensor-embedded display panel 1000), the electronic device 2000 may further include a bus 1310, a processor 1320, a memory 1330, and at least one additional device 1340. Information of the aforementioned sensor-embedded display panel 1000, processor 1320, memory 1330, and at least one additional device 1340 may be transmitted to each other through the bus 1310. In some example embodiments, the at least one additional device 1340 may be omitted. In some example embodiments, the sensor-embedded display panel 1000 may be replaced by a display device including, for example, exclusively light emitting elements and no light absorption sensors, while the at least one additional device 1340 may include one or a plurality (e.g., an array) of photosensors according to any of the example embodiments which may serve as a biometric sensor, a camera, or the like.

The processor 1320 may include one or more articles (e.g., units, instances, etc.) of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. As an example, the processing circuitry may include a non-transitory computer readable storage device. The processor 1320 may control, for example, a display operation of the sensor-embedded display panel 1000 or a sensor operation of the light absorption sensor 310.

The memory 1330 may be a non-transitory computer readable storage medium, such as, for example, as a solid state drive (SSD) and may store an instruction program (e.g., program of instructions), and the processor 1320 may perform a function related to the sensor-embedded display panel 1000 by executing the stored instruction program.

The at least one additional device 1340 may include one or more communication interfaces (e.g., wireless communication interfaces, wired interfaces), user interfaces (e.g., keyboard, mouse, buttons, etc.), power supply and/or power supply interfaces, or any combination thereof.

The units and/or modules described herein may be implemented using hardware constituent elements and software constituent elements. The units and/or modules described herein may include, may be included in, and/or may be implemented by one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. For example, the hardware constituent elements may include microphones, amplifiers, band pass filters, audio-to-digital converters, and processing devices. The processing device may be implemented using one or more hardware devices configured to perform and/or execute program code by performing arithmetic, logic, and input/output operations. The processing device may include a processor, a controller and an arithmetic logic unit, a digital signal processor, a microcomputer, a field programmable array, a programmable logic unit, a microprocessor, or any other device capable of responding to and executing instructions. The processing device may access, store, operate, process, and generate data in response to execution of an operating system (OS) and one or more software running on the operating system.

The software may include a computer program, a code, an instruction, or any combination thereof, and may transform a processing device for a special purpose by instructing and/or configuring the processing device independently or collectively to operate as desired. The software and data may be implemented permanently or temporarily as signal waves capable of providing or interpreting instructions or data to machines, parts, physical or virtual equipment, computer storage media or devices, or processing devices. The software may also be distributed over networked computer systems so that the software may be stored and executed in a distributed manner. The software and data may be stored by one or more non-transitory computer readable storage devices.

The method according to the foregoing embodiments may be recorded in a non-transitory computer readable storage device including program instructions for implementing various operations of the aforementioned example embodiments. The storage device may also include program instructions, data files, data structures, and the like alone or in combination. The program instructions recorded in the storage device may be specially designed for some example embodiments or may be known to those skilled in computer software and available for use. Examples of non-transitory computer-readable storage devices may include magnetic media such as hard disks, floppy disks, and magnetic tapes; optical media such as CD-ROM discs, DVDs and/or blue-ray discs; magneto-optical media such as optical disks; and a hardware device configured to store and execute program instructions such as ROM, RAM, flash memory, and the like. The aforementioned device may be configured to operate as one or more software modules to perform the operations of the aforementioned example embodiments.

Hereinafter, some example embodiments are illustrated in more detail with reference to examples. However, the present scope of the inventive concepts are not limited to these examples.

SYNTHESIS EXAMPLES

Synthesis Example 1-1: Synthesis of Compound Represented by Chemical Formula 1-1

[Chemical Formula 1-1]

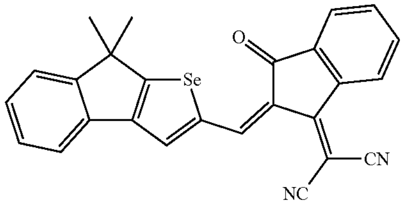

[Reaction Scheme 1-1]

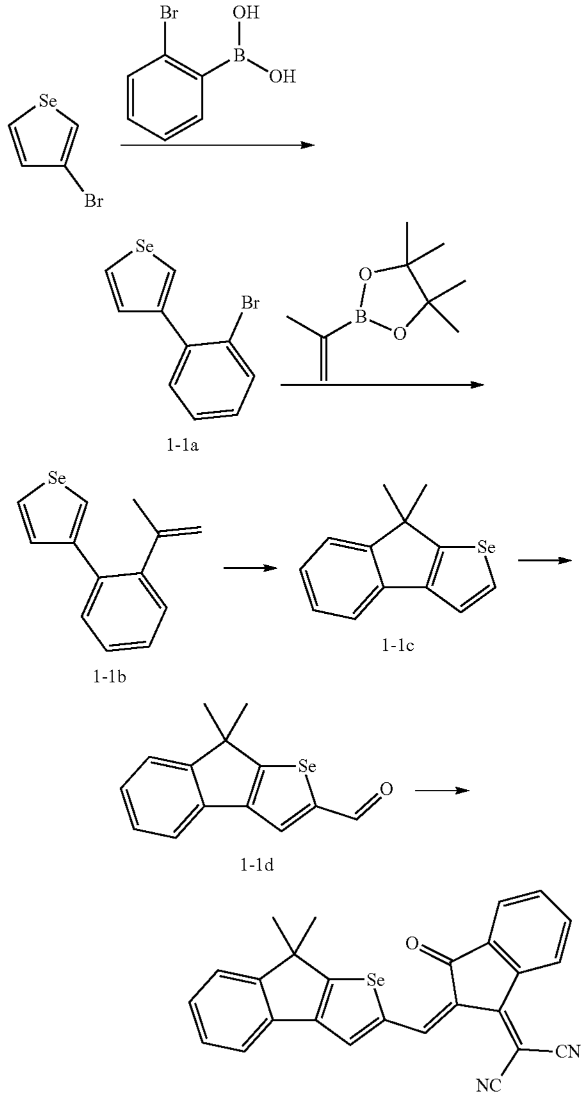

1-1a 1-1b 1-1c 1-1d 1-1

(i) Synthesis of Compound 1-1a 32 g (151.0 mmol) of 3-bromoselenophene, 25 g (126 mmol) of 2-bromophenyl boronic acid, and 7.7 g (6 mmol) of tetrakis(triphenylphosphine)palladium (0) were dissolved in 500 ml of toluene and 100 ml of a $K_2CO_3$ 2N aqueous solution and then, reacted at 90° C. for 24 hours. The resultant is extracted with diethyl ether at room temperature (24° C.), and a product therefrom is separated and purified through silica gel column chromatography (ethyl acetate: hexane=1:8 in a volume ratio), obtaining 35 g (Yield: 97%) of Compound 1-1a.

(ii) Synthesis of Compound 1-1b 35 g (125 mmol) of Compound 1-1a, 28 g (150 mmol) of Isopropenylboronic acid pinacol ester, 7.7 g (6 mmol) of tetrakis(triphenylphosphine)palladium (0), 1.4 g (6 mmol) of palladium (II) acetate, and 2.6 g (6 mmol) of Sphos are dissolved in 500 ml of toluene and 100 ml of a $K_2CO_3$ 2N solution and then, reacted at 90° C. for 24 hours. The resultant is extracted with diethyl ether at room temperature (24° C.), and a product therefrom is separated and purified through silica gel column chromatography (ethyl acetate: hexane=1:8 in a volume ratio), obtaining 5 g (Yield 16%) of Compound 1-1b.

(iii) Synthesis of Compound 1-1c 4.0 g (16.2 mmol) of Compound 1-1 b is dissolved in 200 ml of dichloromethane, and 20 ml (80.9 mmol) of a solution of 4.0 M HCl in dioxane is added dropwise thereto. The mixture is stirred for 24 hours while increasing a temperature from 0° C. to room temperature. 250 ml of water is added thereto and then, extracted with dichloromethane. An extract therefrom is dried by adding anhydrous magnesium sulfate thereto and then, separated and purified through silica gel column chromatography (hexane:dichloromethane=5:1 in a volume ratio), obtaining 1.3 g (Yield: 33%) of Compound 1-1c.

(iv) Synthesis of Compound 1-1d 5.0 ml of phosphoryl chloride is added to 5.0 ml of N,N-dimethylformamide at −15° C. and then, stirred at room temperature (24° C.) for 2 hours. The resultant is slowly added dropwise to a mixture of 100 ml of dichloromethane and 1.3 g of Compound 1-1c at −15° C. and then, stirred at room temperature for 30 minutes and concentrated under a reduced pressure. Subsequently, 150 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and then, dried by adding anhydrous magnesium sulfate thereto. A product obtained therefrom is separated and purified through silica gel column chromatography (hexane:ethyl acetate=4:1 in a volume ratio), obtaining 1.1 g (Yield: 77%) of Compound 1-1d.

(iv) Synthesis of Compound Represented by Chemical Formula 1-1

1.1 g (2.8 mmol) of Compound 1-1d is suspended in ethanol, 0.66 g (3.4 mmol) of 3-(dicyanomethylidene)indan-1-one is added thereto and then, reacted at 50° C. for 2 hours, obtaining 1.4 g (Yield: 92%) of a compound represented by Chemical Formula 1-1. The compound represented by Chemical Formula 1-1 is purified through sublimation up to purity of 99.9%.

$^1$H-NMR (500 MHz, Chloroform-d): δ 9.1 (s, 1H), 8.7 (d, 1H), 8.2 (s, 1H), 7.9 (d, 1H), 7.8 (q, 2H), 7.6 (d, 1H), 7.4 (d, 1H), 7.35 (t, 1H), 7.28 (t, 1H), 1.6 (s, 6H).

Synthesis Example 1-2: Synthesis of Compound Represented by Chemical Formula 1-2

[Chemical Formula 1-2]

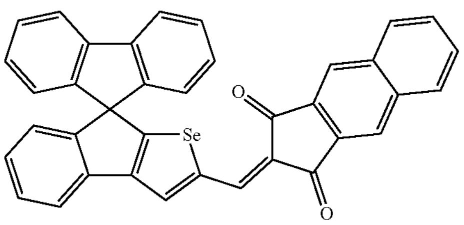

[Reaction Scheme 1-2]

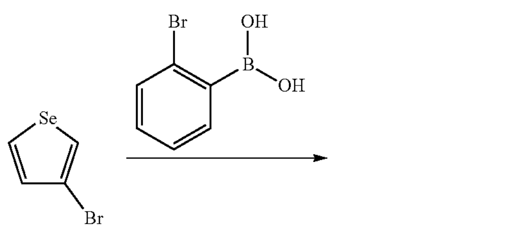

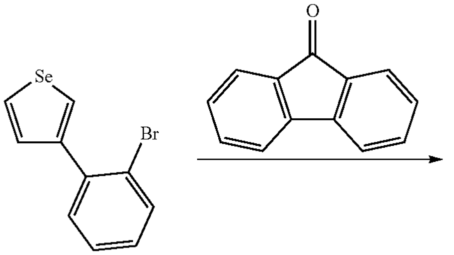

1-2a

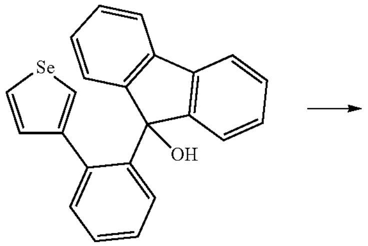

1-2b

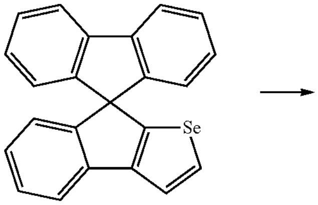

1-2c

-continued

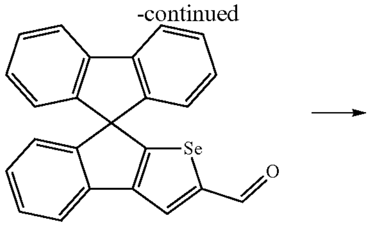

1-2d

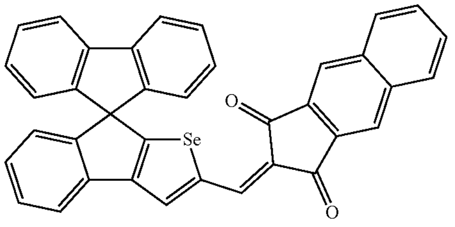

1-2

(i) Synthesis of Compound 1-2a 7.3 g (35 mmol) of 3-bromoselenophene, 7 g (35 mmol) of 2-bromophenyl boronic acid, and 2 g (1.7 mmol) of tetrakis(triphenylphosphine)palladium (0) are dissolved in 100 ml of toluene and 50 ml of a $K_2CO_3$ 2N aqueous solution and then, reacted at 90° C. for 24 hours. A product extracted therefrom with diethyl ether at room temperature (24° C.) is separated and purified through silica gel column chromatography (ethyl acetate:hexane=1:8 in a volume ratio), obtaining 3 g (Yield: 30%) of Compound 1-2a.

(ii) Synthesis of Compound 1-2b 3.0 g (10 mmol) of Compound 1-2a and 2 g (12 mmol) of fluoren-9-one are dissolved in 50 ml of diethyl ether and then, stirred at 0° C. for one hour. Subsequently, 5 ml (12 mmol) of a 2.5 M n-BuLi solution is added dropwise thereto. While the temperature is increased from 0° C. to room temperature, the mixture is stirred for one hour. The resultant is added to 100 ml of water and then, extracted with dichloromethane. An extract therefrom is dried by adding anhydrous magnesium sulfate thereto and then, separated and purified through silica gel column chromatography (hexane:dichloromethane=5:1 in a volume ratio), obtaining 2 g (Yield: 50%) of Compound 1-2b.

(iii) Synthesis of Compound 1-2c 2 g (5 mmol) of Compound 1-2b is dissolved in 100 ml of dichloromethane, and 6.5 ml (26 mmol) of a solution of 4.0 M HCl in dioxane is added thereto. While the temperature is increased from 0° C. to room temperature, the mixture is stirred for 24 hours. 100 ml of water is added thereto and then, extracted with dichloromethane. An extract therefrom is dried with anhydrous magnesium sulfate and then, separated and purified through silica gel column chromatography (hexane:dichloromethane=5:1 in a volume ratio), obtaining 0.8 g (Yield: 42%) of Compound 1-2c.

(iv) Synthesis of Compound 1-2d 1.5 ml of phosphoryl chloride is added dropwise to 1.2 ml of N,N-dimethylformamide at −15° C. and then, stirred at room temperature (24° C.) for 2 hours. The resultant is slowly added dropwise to a mixture of 50 ml of dichloromethane and 0.6 g of Compound 1-2c at −15° C. and then, stirred at room temperature for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. An organic layer extracted therefrom with dichloromethane is washed with an aqueous sodium chloride solution and then, dried by adding anhydrous magnesium sulfate thereto. A product therefrom is separated and purified through silica gel column chromatography (hexane:ethyl acetate=4:1 in a volume ratio), obtaining 0.5 g (Yield: 77%) of Compound 1-2d.

(iv) Synthesis of Compound Represented by Chemical Formula 1-2

0.5 g (1.2 mmol) of Compound 1-2d is suspended in ethanol, and 0.3 g (1.5 mmol) of 1H-cyclopenta[b]naphthalene-1,3(2H)-dione is added thereto and then, reacted at 50° C. for 2 hours, obtaining 0.6 g (Yield: 85%) of a compound represented by Chemical Formula 1-2. The obtained compound represented by Chemical Formula 1-2 is purified through sublimation to purity of 99.9%.

$^1$H-NMR (500 MHz, Chloroform-d): δ 8.44 (s, 1H), 8.35 (s, 1H), 8.32 (s, 1H), 8.27 (s, 1H), 8.06 (m, 2H), 7.87 (d, 2H), 7.70 (d, 1H), 7.65 (m, 2H), 7.43 (t, 2H), 7.37 (t, 1H), 7.17 (t, 2H), 7.07 (t, 1H), 6.86 (d, 2H), 6.74 (d, 1H).

Synthesis Example 1-3: Synthesis of Compound Represented by Chemical Formula 1-3

[Chemical Formula 1-3]

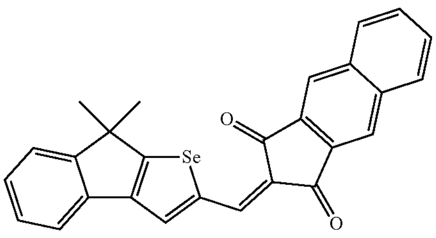

A compound represented by Chemical Formula 1-3 is obtained in the same method as in Synthesis Example 1-1 except that 1H-cyclopenta[b]naphthalene-1,3(2H)-dione is used instead of the 3-(dicyanomethylidene)indan-1-one in the step (iv) of Synthesis Example 1-1. The compound represented by Chemical Formula 1-3 is purified through sublimation to purity of 99.9%.

Synthesis Example 1-4: Synthesis of Compound Represented by Chemical Formula 1-4

[Chemical Formula 1-4]

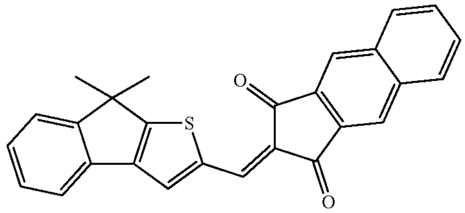

A compound represented by Chemical Formula 1-4 is obtained in the same method as in Synthesis Example 1-1 except that 2-bromothiophene is used instead of the 3-bromoselenophene in the step (i) of Synthesis Example 1-1, and 1H-cyclopenta[b]naphthalene-1,3(2H)-dione is used instead of the 3-(dicyanomethylidene)indan-1-one in the step (iv) of Synthesis Example 1-1. The compound represented by Chemical Formula 1-4 is purified through sublimation to purity of 99.9%.

Comparative Synthesis Example 1-1C: Synthesis of Compound Represented by Chemical Formula 1-1C

[Chemical Formula 1-1C]

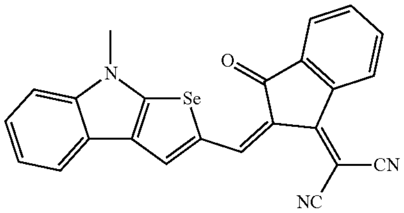

[Reaction Scheme 1-1C]

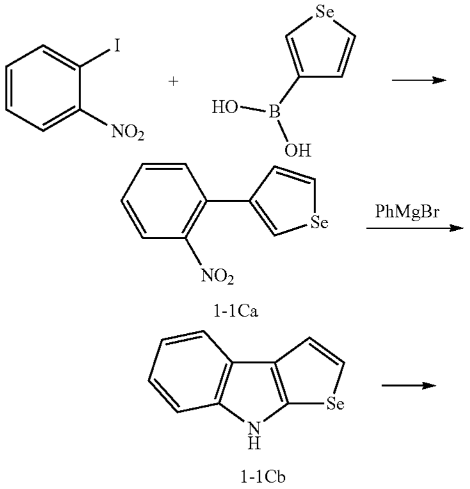

-continued

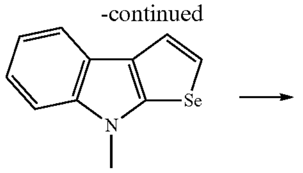

1-1Cc

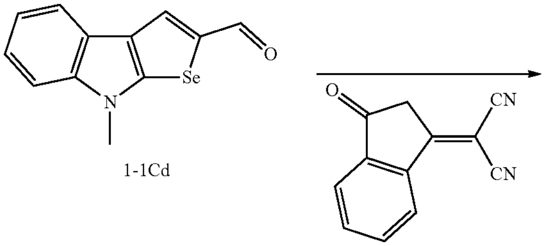

1-1Cd

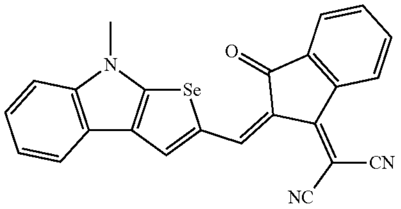

1-1C

(i) Synthesis of Compound 1-1 Ca 2.5 g (10.0 mmol) of 1-iodo-2-nitrobenzene, 2.28 g (13 mmol) of selenophene-3-yl boronic acid, and 0.58 g (0.5 mmol) of tetrakis(triphenylphosphine)palladium (0) are reacted in 50 ml of dimethyl formamide (DMF) and 50 ml of water and then, reacted at 90° C. for 12 hours. The resultant is extracted with diethyl ether at room temperature (24° C.), and a product therefrom is separated and purified through silica gel column chromatography (ethyl acetate: hexane=1:8 in a volume ratio), obtaining 2.2 g (Yield: 87.3%) of Compound 1-1 Ca, 3-(2-nitrophenyl)selenophene.

(ii) Synthesis of Compound 1-1 Cb 5.0 g (19.8 mmol) of 3-(2-nitrophenyl)selenophene is dissolved in 250 ml of dry THE and then, cooled to 0° C., and 19.19 ml (59.5 mmol) of PhMgBr (1.0 M in a THE solution) is slowly added thereto. An internal temperature of the solution is controlled not to exceed 3° C. during the addition over 10 minutes. The mixture is reacted at 0° C. for 5 minutes, and 50 ml of a $NH_4Cl$ saturated aqueous solution is added thereto. After adding 500 ml of water thereto, an organic layer therefrom is washed with an aqueous sodium chloride solution, three times extracted with ethyl acetate, and dried with anhydrous magnesium sulfate. A product therefrom is separated and purified through silica gel column chromatography (ethyl acetate:hexane=1:5 in a volume ratio), obtaining 3.5 g (Yield: 80.2%) of Compound 1-1Cb, 8H-selenopheno[2,3-b]indole.

(iii) Synthesis of Compound 1-1 Cc 3.0 g (13.6 mmol) of the 8H-selenopheno[2,3-b]indole and 7.65 g (136.3 mmol) of potassium hydroxide are dissolved in 50 ml of dimethyl sulfoxide, and 13.2 g (40.9 mmol) of iodomethane is added dropwise thereto. The mixture is stirred at 30° C. for 5 hours. 250 ml of water is added thereto and then, extracted with dichloromethane. An extract therefrom is dried by adding anhydrous magnesium sulfate thereto and then, separated and purified through silica gel column chromatography (hexane:dichloromethane=5:1 in a volume ratio), obtaining 2.80 g (Yield: 87.7%) of Compound 1-1 Cc, 8-methyl-8H-selenopheno[2,3-b]indole.

(iv) Synthesis of Compound 1-1 Cd 2.4 ml of phosphoryl chloride is added dropwise to 15.0 ml of N,N-dimethylformamide at −15° C. and then, stirred at room temperature (24° C.) for 2 hours. The resultant is slowly added dropwise to a mixture of 100 ml of dichloromethane and 1.3 g of Compound 1-1Cc at −15° C. and then, stirred at room temperature for 30 minutes and concentrated under a reduced pressure. Subsequently, 150 ml of water is added thereto, an aqueous sodium hydroxide solution is added thereto until pH becomes 14 and then, stirred at room temperature (24° C.) for 2 hours. An organic layer extracted therefrom with dichloromethane is washed with an aqueous sodium chloride solution and dried by adding anhydrous magnesium sulfate thereto. A product obtained therefrom is separated and purified through silica gel column chromatography (hexane:ethyl acetate=4:1 in a volume ratio), obtaining 1.4 g (Yield: 76.9%) of Compound 1-1 Cd, 8-methyl-8H-selenopheno[2,3-b]indole-2-carbaldehyde.

(iv) Synthesis of Compound Represented by Chemical Formula 1-1C 0.75 g (2.86 mmol) of Compound 1-1Cd is suspended in ethanol, and 0.59 g (3.00 mmol) of 3-(dicyanomethylidene)indan-1-one is added thereto and then, reacted at 50° C. for 2 hours, obtaining 1.05 g (Yield: 83.4%) of Compound 1-1C. The compound represented by Chemical Formula 1-1C is purified through sublimation to purity of 99.9%.

Comparative Synthesis Example 1-4C: Synthesis of Compound Represented by Chemical Formula 1-4C

[Chemical Formula 1-4C]

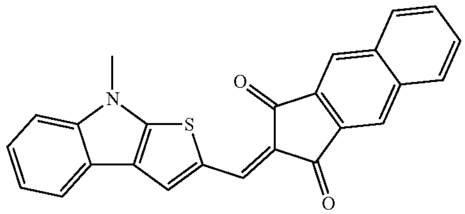

[Reaction Scheme 1-4C]

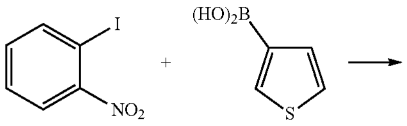

-continued

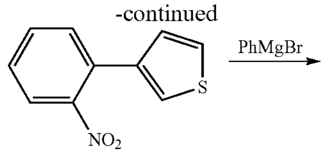

1-4Ca

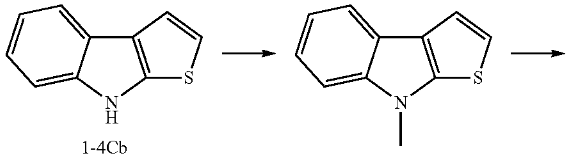

1-4Cb 1-4Cc

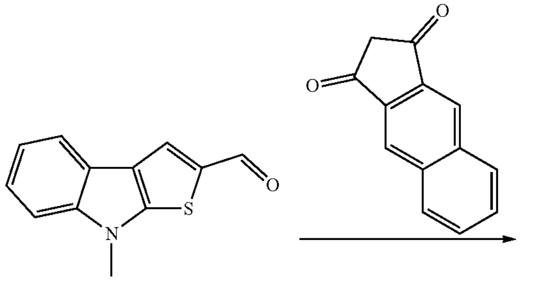

1-4Cd

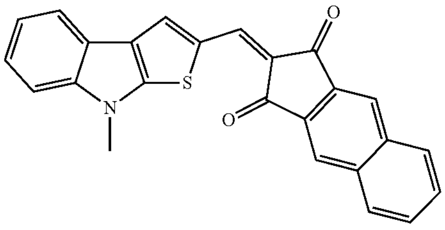

1-4C (i) Synthesis of Compound 1-4Ca 2.5 g (10.0 mmol) of 1-iodo-2-nitrobenzene, 2.28 g (13 mmol) of thiophen-3-yl boronic acid, and 0.58 g (0.5 mmol) of tetrakis(triphenylphosphine)palladium (0) are dissolved in 50 ml of dimethyl formamide (DMF) and 50 ml of water and then, reacted at 90° C. for 12 hours. The resultant is extracted with diethyl ether at room temperature (24° C.), and a product obtained therefrom is separated and purified through silica gel column chromatography (ethyl acetate: hexane=1:8 in a volume ratio), obtaining 2.2 g (Yield: 87.3%) of Compound 1-4Ca, 3-(2-nitrophenyl)thiophene. This process is repeated for several times to obtain more Compound 1-4Ca.

(ii) Synthesis of Compound 1-4Cb 5.0 g (19.8 mmol) of 3-(2-nitrophenyl)thiophene is dissolved in 250 ml of dry THF and then, cooled to 0° C., and 19.19 ml (59.5 mmol) of PhMgBr (1.0 M in a THE solution) is slowly added dropwise thereto. During the addition over 10 minutes, an internal temperature of the mixture is controlled not to exceed 3° C. After reacting them at 0° C. for 5 minutes, 50 ml of a $NH_4Cl$ saturated aqueous solution is added thereto. 500 ml of water is added thereto, and an organic layer therefrom is washed with an aqueous sodium chloride solution, three times extracted with ethyl acetate, and dried by adding anhydrous magnesium sulfate thereto. A product therefrom is separated and purified through silica gel column chromatography (ethyl acetate:hexane=1:5 in a volume ratio), obtaining 3.5 g (Yield: 80.2%) of Compound 1-4Cb, 8H-thiopheno[2,3-b]indole.

(iii) Synthesis of Compound 1-4Cc 3.0 g (13.6 mmol) of 8H-thiopheno[2,3-b]indole and 7.65 g (136.3 mmol) of potassium hydroxide are dissolved in 50 ml of dimethyl sulfoxide, and 13.2 g (40.9 mmol) of iodomethane is added thereto. The mixture is stirred at 30° C. for 5 hours. 250 ml of water is added thereto and then, extracted with dichloromethane. An extract therefrom is dried with anhydrous magnesium sulfate and separated and purified through silica gel column chromatography (hexane: dichloromethane=5:1 in a volume ratio), obtaining 2.80 g (Yield: 87.7%) of Compound 1-4Cc, 8-methyl-8H-thiopheno[2,3-b]indole.

(iv) Synthesis of Compound 1-4Cd 2.4 ml of phosphoryl chloride is added to 15.0 ml of N,N-dimethylformamide at −15° C. and then, stirred at room temperature (24° C.) for 2 hours. The resultant is slowly added dropwise to a mixture of 100 ml of dichloromethane and 1.3 g of Compound 1-4Cc at −15° C. and then, stirred at room temperature for 30 minutes and concentrated under a reduced pressure. 150 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and then, dried by adding anhydrous magnesium sulfate thereto. A product therefrom is separated and purified through silica gel column chromatography (hexane:ethyl acetate=4:1 in a volume ratio), obtaining 1.4 g (Yield: 76.9%) of Compound 1-4Cd, 8-methyl-8H-thiopheno[2,3-b]indole-2-carbaldehyde.

(iv) Synthesis of Compound Represented by Chemical Formula 1-4C 0.75 g (2.86 mmol) of Compound 1-4Cd is suspended in ethanol, and 0.59 g (3.00 mmol) of 1H-cyclopenta[b]naphthalene-1,3(2H)-dione is added thereto and then, reacted at 50° C. for 2 hours, obtaining 1.05 g (Yield: 83.4%) of Compound 1-4C. The compound represented by Chemical Formula 1-4C is purified through sublimation to purity of 99.9%.

$^1$H-NMR (500 MHz, Methylene Chloride-$d_2$): δ 8.8 (d, −2H), 8.3 (s, 1H), 8.2 (m, 2H), 8.0 (d, 1H), 7.8 (m, 2H), 7.5 (m, 2H), 7.2 (d, 1H), 6.7 (s, 1H), 3.7 (s, 3H).

Synthesis Example 2-1: Synthesis of Compound Represented by Chemical Formula 2-1

[Chemical Formula 2-1]

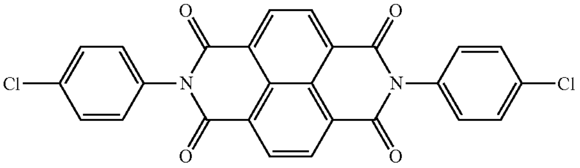

A mixture of 1,4,5,8-naphthalenetetracarboxylic dianhydride (1 eq.) and 4-chloroaniline (2.2 eq.) is dissolved in a dimethyl formamide (DMF) solvent and then, put in a two-necked and round-bottomed flask and stirred at 180° C. for 24 hours. Subsequently, after lowering the temperature to room temperature, methanol is added thereto, and a product therefrom is filtered, obtaining a powder-type material. The material is several times washed with methanol and purified through recrystallization with ethyl acetate and dimethylsulfoxide (DMSO). The obtained product is dried in an oven under vacuum at 80° C. for 24 hours, obtaining a compound represented by Chemical Formula 2-1. A yield thereof is 50% or more.

$^1$H NMR (300 MHz, $CDCl_3$ with Hexafluoro isopropanol): δ=8.85 (s, 4H), 7.63 (s, 4H), 7.60 (s, 4H).

Synthesis Example 2-2: Preparation of Compound Represented by Chemical Formula 2-2

[Chemical Formula 2-2]

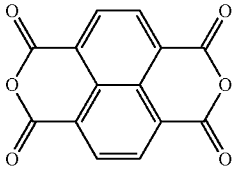

A compound represented by Chemical Formula 2-2 (Tokyo Chemical Industry Co., Ltd.) is prepared through sublimation/purification and may be used as an n-type compound in an active layer of a photoelectric device including the compound represented by Chemical Formula 1 as a p-type compound.

Synthesis Example 2-3

Fullerene ($C_{60}$, nanom purple ST, Frontier Carbon Corp.) is prepared and may be used as n-type compound in an active layer of a photoelectric device including the compound represented by Chemical Formula 1 as a p-type compound.

Synthesis Example 3-1

[Chemical Formula 3-1]

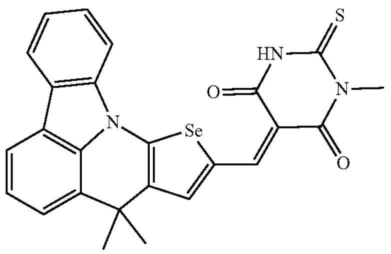

[Reaction Scheme 3-1]

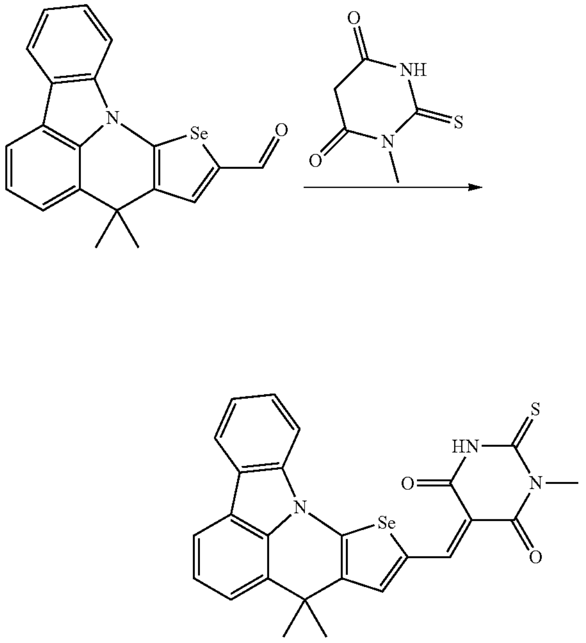

3-1

4,4-dimethyl-4H-selenopheno[3',2':5,6]pyrido[3,2,1-jk]carbazole-2-carbaldehyde (Compound 3-1a) is synthesized in the same method as Compound 1-1D in Synthesis Example 1-1 of US Patent Publication No. 2021-0234103. 2.00 g (5.55 mmol) of 4,4-dimethyl-4H-selenopheno[3',2':5,6]pyrido[3,2,1-jk]carbazole-2-carbaldehyde is suspended in ethanol, and 1.05 g (6.66 mmol) of 1-methyl-2-thioxodihydropyrimidine-4,6(1H,5H)-dione is added thereto and then, reacted at 50° C. for 24 hours, obtaining 2.4 g of a compound represented by Chemical Formula 3-1. A yield thereof is 86%. The obtained compound is purified through sublimation to purity of 99.9%.

$^1$H-NMR (500 MHz, Methylene Chloride-d2): δ 8.95 (s, 1H), 8.77 (s, 1H), 8.65 (s, 2H), 8.18 (s, 2H), 8.06 (d, 2H), 7.92 (d, 2H), 7.83 (d, 2H), 7.62 (d, 2H), 7.44 (t, 2H), 7.36 (m, 6H), 3.76 (s, 3H), 3.71 (s, 3H), 1.68 (s, 12H).

Synthesis Example 3-2

[Chemical Formula 3-2]

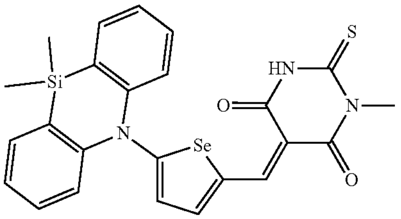

[Reaction Scheme 3-2]

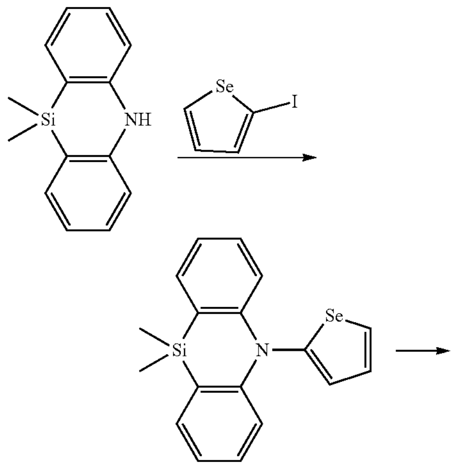

3-2a

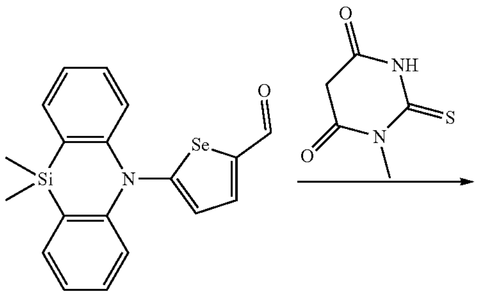

3-2b

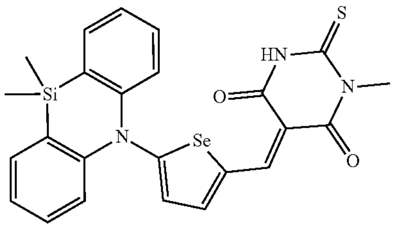

3-2

(i) Synthesis of Compound 3-2a 7.01 g (27.3 mmol) of 2-iodoselenophene and 5.59 g (24.8 mmol) of 10,10-dimethyl-5,10-dihydrodibenzo[b,e][1,4] azasiline are heated under reflux in 150 ml of anhydrous toluene for 2 hours under presence of 5 mol % of tris (dibenzylideneacetone)dipalladium (0) ($Pd(dba)_2$), 5 mol % of tri-t-butylphosphine ($P(t\text{-}Bu)_3$), and 7.15 g (74.4 mmol) of sodium t-butoxide (NaOtBu). A product therefrom is separated and purified through silica gel column chromatography (toluene:hexane=1:4 in a volume ratio), obtaining 8.0 g of Compound 3-2a, 10,10-dimethyl-5-(selenophen-2-yl)-5,1 0-dihydrodibenzo[b,e][1,4]azasiline. A yield thereof is 80%.

(ii) Synthesis of Compound 3-2b 1.11 ml of phosphoryl chloride is added dropwise to 3.19 ml of N,N-dimethylformamide at −15° C. and then, stirred at room temperature (24° C.) for 2 hours. Subsequently, the resultant is slowly added dropwise to a mixture of 200 ml of dichloromethane and 3.19 g of Compound 3-2a at −15° C. and then, stirred at room temperature (24° C.) for 30 minutes and concentrated under a reduced pressure. 100 ml of water is added thereto, and an aqueous sodium hydroxide solution is added thereto until pH becomes 14 and then, stirred at room temperature (24° C.) for 2 hours. Subsequently, an organic layer extracted with dichloromethane therefrom is washed with an aqueous sodium chloride solution and then, dried by adding anhydrous magnesium sulfate thereto. A product therefrom is separated and purified through silica gel column chromatography (hexane:ethylacetate=4:1 in a volume ratio), obtaining 2.20 g of Compound 3-2b, 5-(10, 10-dimethyldibenzo[b,e][1,4]azasilin-5(10H)-yl)selenoo-phene-2-carbaldehyde. A yield thereof is 73%.

(iii) Synthesis of Compound Represented by Chemical Formula 3-2

1.77 g (4.64 mmol) of Compound 3-2b is suspended in ethanol, and 0.89 g (5.57 mmol) of 1-methyl-2-thioxodihy-dropyrimidine-4,6(1H,5H)-dione are added thereto and then, reacted at 50° C. for 2 hours, obtaining 2.0 g of a compound represented by Chemical Formula 3-2. A yield thereof is 83%. The compound is purified through sublimation to purity of 99.9%. The compound may be used as p-type compound in an active layer of a photoelectric device including the compound represented by Chemical Formula 1 as a p-type compound.

$^1$H-NMR (500 MHz, DMSO-d6): δ12.1 (d, 1H), 8.29 (d, 1H), 8.22 (dd, 1H), 7.89 (dd, 2H), 7.76 (d, 2H), 7.61 (q, 2H), 7.48 (q, 2H), 6.59 (t, 1H), 3.48 (d, 3H), 0.41 (s, 12H).

Evaluation I: Sublimation Temperature and Reorganization Energy of Compounds

The sublimation temperatures of the compounds according to Synthesis Example 1-1 and Synthesis Example 1-2 are evaluated. The sublimation temperature is evaluated by thermogravimetric analysis (TGA), and is evaluated by a temperature at which the weight of the sample decreases by 10% compared to the initial weight by increasing the temperature under a high vacuum of 10 Pa or less. The results are shown in Table 1.

TABLE 1

| | $T_{s(10)}$(° C.) |
|---|---|
| Synthesis Example 1-1 | 196 |
| Synthesis Example 1-2 | 271 |

* $T_{s(10)}$(° C.): a temperature at which a weight of the sample decreased by 10% relative to the initial weight Referring to Table 1, the sublimation temperatures of the compounds according to Synthesis Examples 1-1 and 1-2 are low, which indicates that the compounds according to Synthesis Examples 1-1 and 1-2 have improved deposition stability.

The reorganization energies of the compounds according to Synthesis Examples 1-1, 1-3, and 1-4 and Comparative Synthesis Example 1-4C are calculated at the DFT B3LYP/DGDZVP level using the Gaussian 09 program. The results are shown in Table 2.

TABLE 2

| | Reorganization Energy (eV) |
|---|---|
| Synthesis Example 1-1 | 0.18 |
| Synthesis Example 1-3 | 0.22 |
| Synthesis Example 1-4 | 0.21 |
| Comparative Synthesis Example 1-4C | 0.24 |

Referring to Table 2, the reorganization energies of the compounds according to the synthesis examples are lower than that of the comparative synthesis example, which indicate that the stability of the molecule and the packing property during the deposition process are improved.

Evaluation II: Energy Level and Energy Bandgap of Compounds

The compounds according to Synthesis Example 1-1 and Synthesis Example 1-2 are respectively deposited on a glass substrate, and the deposited thin films are measured with respect to energy levels. A HOMO energy level is obtained by irradiating UV light into the thin films and measuring an amount of photoelectrons emitted according to the energy with AC-2 (Hitachi) or AC-3 (Riken Keiki Co., Ltd.). An energy bandgap is obtained by using a UV-Vis spectrometer (Shimadzu Corp.). Then, a LUMO energy level is calculated by using the energy bandgap and the HOMO energy level. The results are shown in Table 3.

TABLE 3

| | HOMO (eV) | LUMO (eV) | Energy bandgap (eV) |
|---|---|---|---|
| Synthesis Example 1-1 | 6.05 | 4.04 | 2.01 |
| Synthesis Example 1-2 | 6.08 | 3.89 | 2.19 |

* HOMO, LUMO: absolute value

Table 4 shows the energy levels of the compounds according to Synthesis Examples 1-3 and 1-4, calculated according to Discrete Fourier Transform (DFT).

TABLE 4

| | HOMO (eV) | LUMO (eV) | Energy bandgap (eV) |
|---|---|---|---|
| Synthesis Example 1-3 | 5.96 | 2.98 | 2.98 |
| Synthesis Example 1-4 | 6.01 | 2.95 | 3.06 |

* HOMO, LUMO: absolute value

Referring to Tables 3 and 4, the compounds according to Synthesis Examples 1-1 to 1-4 may be used as p-type semiconductors or n-type semiconductors.

EXAMPLES

Example 1-1: Manufacture of Photoelectric Device

Al (10 nm), ITO (100 nm), and Al (8 nm) are sequentially deposited on a glass substrate to form a first electrode (lower electrode) having an Al/ITO/Al structure. Subsequently, N,N'-bis(3-methylphenyl)-N,N'-diphenyl-[1,1-biphenyl]-4,4'-diamine is deposited on the first electrode to form a 170 nm-thick hole auxiliary layer (HOMO: 5.6 eV, LUMO: 2.1 eV). On hole auxiliary layer, the compound represented by Chemical Formula 1-1 obtained in Synthesis Example 1-1 (p-type semiconductor, HOMO: 6.05 eV, LUMO: 4.04 eV) is deposited to be 10 nm thick, and then, the compound obtained in Synthesis Example 2-1 (n-type semiconductor, HOMO: 6.19 eV, LUMO: 3.20 eV) is deposited to be 40 nm thick, forming a bi-layered light absorbing layer ($\lambda_{max}$=545 nm). On the light absorbing layer, 4,7-diphenyl-1,10-phenanthroline is deposited to form a 36 nm-thick electron auxiliary layer (HOMO: 6.1 eV, LUMO: 3.0 eV). Then, magnesium and silver are deposited on the electron auxiliary layer to form a 16 nm-thick Mg:Ag (in a volume ratio of 1:10) upper electrode to manufacture a photoelectric device.

Example 1-2: Manufacture of Photoelectric Device

A photoelectric device is manufactured according to the same method as Example 1-1 except that the compound represented by Chemical Formula 1-2 according to Synthesis Example 1-2 (p-type semiconductor) is used instead of the compound represented by Chemical Formula 1-1 according to Synthesis Example 1-1 (p-type semiconductor).

Comparative Example 1-1C: Manufacture of Photoelectric Device

A photoelectric device is manufactured according to the same method as Example 1-1 except that the compound represented by Chemical Formula 1-4C according to Comparative Synthesis Example 1-4C (p-type semiconductor) is used instead of the compound represented by Chemical Formula 1-1 according to Synthesis Example 1-1 (p-type semiconductor).

Example 2-1: Manufacture of Photoelectric Device

Al (10 nm), ITO (100 nm), and Al (8 nm) are sequentially deposited on a glass substrate to form a lower electrode having an Al/ITO/Al structure. Then, N,N'-bis(3-methylphenyl)-N,N'-diphenyl-[1,1-biphenyl]-4,4'-diamine is deposited on the first electrode to form a 170 nm-thick hole auxiliary layer (HOMO: 5.6 eV, LUMO: 2.1 eV). On hole auxiliary layer, the compound obtained in Synthesis Example 3-1 (p-type semiconductor, HOMO: 5.66 eV, LUMO: 3.70 eV) is deposited to be 10 nm thick, and then, the compound obtained in Synthesis Example 1-1 (n-type semiconductor, HOMO: 6.05 eV, LUMO: 4.04 eV) is deposited to be 40 nm thick, forming a bi-layered light absorbing layer ($\lambda_{max}$=545 nm). On the light absorbing layer, 4,7-diphenyl-1,10-phenanthroline is deposited to form a 36 nm-thick electron auxiliary layer (HOMO: 6.1 eV, LUMO: 3.0 eV). Then, magnesium and silver are deposited on the electron auxiliary layer to form a 16 nm-thick Mg:Ag (in a volume ratio of 1:10) upper electrode to manufacture a photoelectric device.

Example 2-2: Manufacture of Photoelectric Device

A photoelectric device is manufactured according to the same method as Example 2-1 except that the compound represented by Chemical Formula 1-2 according to Synthesis Example 1-2 (n-type semiconductor) is used instead of the compound represented by Chemical Formula 1-1 according to Synthesis Example 1-1 (n-type semiconductor).

Comparative Example 2-1C: Manufacture of Photoelectric Device

A photoelectric device is manufactured according to the same method as Example 1-1 except that the compound represented by Chemical Formula 2-3 (n-type semiconductor) is used instead of the compound represented by Chemical Formula 1-1 according to Synthesis Example 1-1 (n-type semiconductor).

[Chemical Formula 2-3]

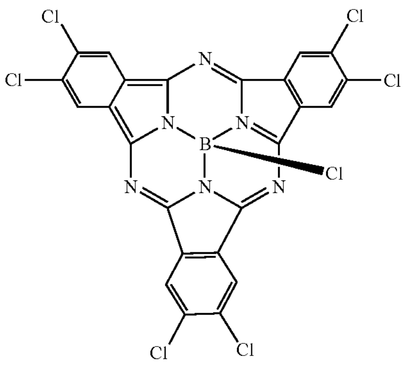

Evaluation III

After the photoelectric devices according to Example 1-1, Example 1-2 and Comparative Example 1-2C were left at 85° C. for one hour, external quantum efficiency (EQE) is evaluated. The external quantum efficiency (EQE) is evaluated by using incident photon to current efficiency (IPCE) at a wavelength of 450 nm (blue, B), 530 nm (green, G), and 630 nm (red, R). The results are shown in Table 5.

TABLE 5

| | EQE (3 V, %), 85° C. 1 h | | | Ratio of external quantum efficiencies | |
|---|---|---|---|---|---|
| | EQE(B) | EQE(G) | EQE(R) | EQE(G)/EQE(B) | EQE(G)/EQE(R) |
| Example 1-1 | 0.5 | 19.8 | 0.0 | 39.6 | ∞ |
| Example 1-2 | 1.0 | 15.4 | 0.0 | 15.4 | ∞ |
| Comparative Example 1-1C | 2.2 | 10.1 | 2.1 | 4.6 | 4.8 |

The external quantum efficiency (EQE) of the photoelectric devices according to Example 2-1 and Comparative Example 2-1 C is evaluated. The external quantum efficiency is evaluated at room temperature (25° C.). The external quantum efficiency (EQE) is evaluated by using incident photon to current efficiency (IPCE) at a wavelength of 450 nm (blue, B), 530 nm (green, G), and 630 nm (red, R). The results are shown in Table 6.

TABLE 6

| | EQE (3 V, %) | | | Ratio of external quantum efficiency | |
|---|---|---|---|---|---|
| | EQE(B) | EQE(G) | EQE(R) | EQE(G)/EQE(B) | EQE(G)/EQE(R) |
| Example 2-1 | 0.8 | 19.1 | 12.3 | 23.9 | 1.6 |
| Comparative Example 2-1C | 0.5 | 2.5 | 1.3 | 5 | 1.9 |

Referring to Tables 5 and 6, the photoelectric devices according to the examples exhibit improved photoelectric conversion efficiency at a green wavelength spectrum and in addition, higher photoelectric conversion efficiency (ratios of external quantum efficiencies) at a green wavelength relative to photoelectric conversion efficiency at a blue wavelength or a red wavelength and thus high wavelength selectivity at a green wavelength, compared with the sensors according to the comparative examples.

Evaluation IV

The photoelectric devices according to Example 1-1, Example 1-2, Comparative Example 1-2C, Example 2-1, and Comparative Example 2-1C are evaluated with respect to a dark current under a reverse bias voltage at room temperature and after left at 85° C. for 1 h.

The dark current is evaluated with dark current density, which is obtained by using a current-voltage evaluating equipment (Keithley K4200 parameter analyzer) and dividing the dark current by a unit pixel area (0.04 $cm^2$), and the dark current density is evaluated from a current flowing when a reverse bias voltage of −3 V is applied to the photoelectric devices. The results are shown in Tables 7 and 8.

TABLE 7

| | Dark currert ($mA/cm^2$) | |
|---|---|---|
| | room temperature | 85° C., 1 h |
| Example 1-1 | $8.6 \times 10^{-6}$ | $1.4 \times 10^{-6}$ |
| Example 1-2 | $1.3 \times 10^{-5}$ | $1.5 \times 10^{-6}$ |
| Comparative Example 1-2C | $5.2 \times 10^{-4}$ | $1.6 \times 10^{-4}$ |

TABLE 8

| | Dark currert ($mA/cm^2$) | |
|---|---|---|
| | room temperature | 85° C., 1 h |
| Example 2-1 | $9.3 \times 10^{-6}$ | $3.1 \times 10^{-6}$ |
| Comparative Example 2-1C | $6.4 \times 10^{-4}$ | unmeasurable |

In Table 8, "unmeasurable" means that the device is damaged during annealing at 85° C. and thus measurement was not possible.

Referring to Tables 7 and 8, the photoelectric devices according to the examples exhibit a lower dark current than the photoelectric devices according to the comparative example when the reverse bias voltage is applied thereto.

While the inventive concepts has been described in connection with what is presently considered to be practical example embodiments, it is to be understood that the inventive concepts are not limited to such example embodiments, but, on the contrary, are intended to cover various modifications and equivalent arrangements included within the spirit and scope of the appended claims.

DESCRIPTION OF SYMBOLS

10: first electrode
20: second electrode
30: active layer
40, 45: charge auxiliary layer
100, 200: photoelectric device
300, 400, 500, 600, 700: organic CMOS image sensor

310: semiconductor substrate
70B, 72B: blue filter 70R, 72R: red filter
70, 72: color filter layer
85: through-hole
60: lower insulation layer
80: upper insulation layer
50B, 50R: photo-sensing device
55: charge storage
90: recognition target
95: encapsulation layer
110: substrate
120: thin film transistor
140: insulation layer
141, 142: contact hole
150: pixel definition layer
210, 220, 230: light emitting element
310: light absorbing sensor
211, 221, 231, 311: pixel electrode
212, 222, 232: light emitting layer
320: common electrode
330: light absorbing layer
340: first common auxiliary layer
350: second common auxiliary layer
1000: sensor-embedded display panel
2000: electronic device

The invention claimed is:

1. A compound represented by Chemical Formula 1:

[Chemical Formula 1]

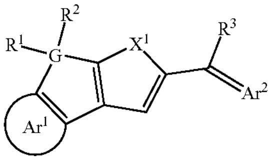

wherein, in Chemical Formula 1,

G is C, Si, or Ge, $R^1$ and $R^2$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, or a cyano group (—CN), wherein $R^1$ and $R^2$ are each independently present or are linked to each other to provide a first spiro structure, $X^1$ is O, S, Se, Te, S(═O), S(═O)$_2$, SiR$^a$R$^b$, GeR$^e$R$^d$, or CR$^e$R$^f$, wherein $R^a$, $R^b$, $R^e$, $R^d$, $R^e$, and $R^f$ are each independently hydrogen, deuterium, a substituted or unsubstituted C1 to C20 alkyl group, or a substituted or unsubstituted C6 to C20 aryl group, wherein $R^a$, $R^b$, $R^e$, $R^d$, $R^e$, and $R^f$ are each independently present or at least one pair of $R^a$ and $R^b$, $R^e$ and $R^d$, or $R^e$ and $R^f$ is linked to each other to provide a second spiro structure, $R^3$ is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, pentafluorosulfanyl group (—SF$_5$), a hydroxyl group, a hydrazine group, a hydrazone group, a carboxyl group or a salt thereof, a sulfonic acid group or a salt thereof, a phosphoric acid group or a salt thereof, —SiR$^a$R$^b$R$^e$ wherein $R^a$, $R^b$, and $R^e$ are each independently hydrogen or a substituted or unsubstituted C1 to C10 alkyl group, or any combination thereof, $Ar^2$ is a substituted or unsubstituted C6 to C30 hydrocarbon cyclic group including at least one functional group of C═O, C═S, C═Se, C═Te, or C═CR$^a$R$^b$, wherein $R^a$ and $R^b$ are each independently hydrogen, a substituted or unsubstituted C1 to C10 alkyl group, a cyano group or a cyano-containing group; a substituted or unsubstituted C2 to C30 heterocyclic group including at least one functional group of C═O, C═S, C═Se, C═Te, or C═CR$^a$R$^b$, wherein $R^a$ and $R^b$ are each independently hydrogen, a substituted or unsubstituted C1 to C10 alkyl group, a cyano group, or a cyano-containing group; or a fused ring thereof, and $Ar^1$ is one of moieties represented by Chemical Formula 2:

[Chemical Formula 2]

(1)

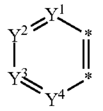

(2)

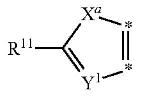

(3)

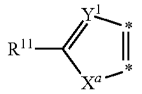

(4)

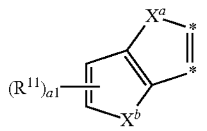

(5)

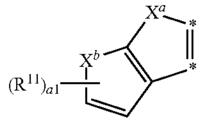

(6)

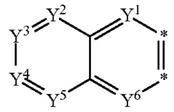

(7)

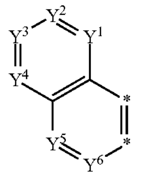

(8)

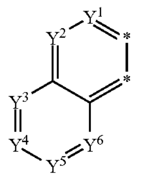

-continued (9)

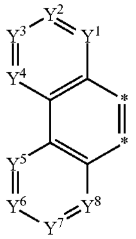

(10)

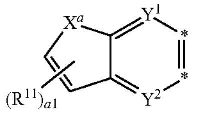

(11)

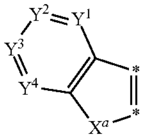

(12)

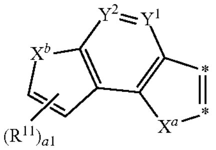

(13)

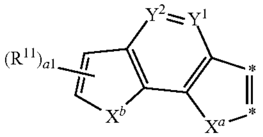

(14)

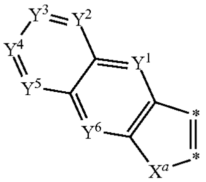

(15)

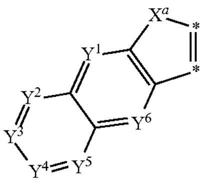

(16)

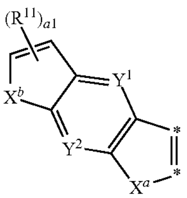

(17)

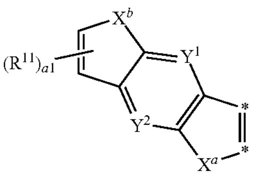

-continued (18)

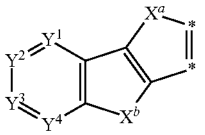

(19)

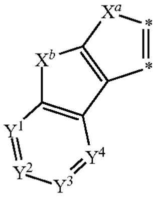

wherein, in Chemical Formula 2, $Y^1$ to $Y^8$ are each independently N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $CR^p$'s are linked to each other to provide a substituted or unsubstituted C6 to C30 arene group, a substituted or unsubstituted C3 to C30 heteroarene group, or a condensed ring thereof, $X^a$ and $X^b$ are each independently O, S, Se, Te, S(=O), $S(=O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are each independently hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ are each independently present or at least one pair of $R^b$ and $R^c$, $R^d$ and $R^e$, or $R^f$ and $R^g$ is linked to each other to provide a third spiro structure, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 2, and

* indicates a linking point that is linked to a pentagonal ring of Chemical Formula 1.

2. The compound of claim 1, wherein in Chemical Formula 1, $X^1$ is O, S, Se, or Te.

3. The compound of claim 1, wherein in Chemical Formula 1, $Ar^1$ is one of moieties represented by Chemical Formula 2A:

[Chemical Formula 2A]

(1)

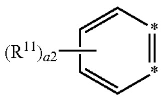

(2)

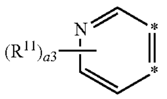

(3)

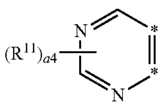

-continued (4)

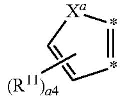

(5)

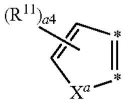

wherein, in Chemical Formula 2A, $X^a$ is O, S, Se, Te, S(=O), $S(=O)_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are each independently hydrogen, a substituted or unsubstituted C1 to C10 alkyl group or a substituted or unsubstituted C6 to C10 aryl group, and $R^a$, $R^b$, $R^c$, $R^d$, $R^e$, $R^f$, and $R^g$ are each independently present or at least one pair of $R^b$ and $R^c$, $R^d$ and $R^e$, or $R^f$ and $R^g$ is linked to each other to provide a fourth spiro structure, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a2 is an integer from 0 to 4, a3 is an integer from 0 to 3, a4 is an integer from 0 to 2, and

* indicates a linking point that is linked to a pentagonal ring of Chemical Formula 1.

4. A compound represented by Chemical Formula 1:

[Chemical Formula 1]

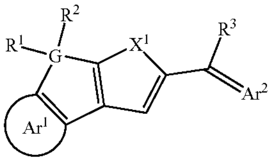

wherein, in Chemical Formula 1,

G is C, Si, or Ge, $R^1$ and $R^2$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, or a cyano group (—CN), wherein $R^1$ and $R^2$ are each independently present or are linked to each other to provide a first spiro structure, $X^1$ is O, S, Se, Te, S(=O), $S(=O)_2$, $SiR^aR^b$, $GeR^cR^d$, or $CR^eR^f$, wherein $R^a$, $R^b$, $R^c$, $R^d$, $R^e$, and $R^f$ are each independently hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ are each independently present or at least one pair of $R^a$ and $R^b$, $R^c$ and $R^d$, or $R^e$ and $R^f$ is linked to each other to provide a second spiro structure, $R^3$ is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, pentafluorosulfanyl group (—$SF_5$), a hydroxyl group, a hydrazine group, a hydrazone group, a carboxyl group or a salt thereof, a sulfonic acid group or a salt thereof, a phosphoric acid group or a salt thereof, —$SiR^aR^bR^e$ wherein $R^a$, $R^b$, and $R^e$ are each independently hydrogen or a substituted or unsubstituted C1 to C10 alkyl group, or any combination thereof, $Ar^1$ is a substituted or unsubstituted benzene ring, a substituted or unsubstituted naphthalene ring, a substituted or unsubstituted anthracene ring, a substituted or unsubstituted indene ring, a substituted or unsubstituted phenanthrene ring, a substituted or unsubstituted fluorene ring, a substituted or unsubstituted acenaphthylene ring, a substituted or unsubstituted thiophene ring, a substituted or unsubstituted selenophene ring, a substituted or unsubstituted tellurophene ring, a substituted or unsubstituted pyridine ring, a substituted or unsubstituted pyrimidine ring, a substituted or unsubstituted pyrazine ring, a substituted or unsubstituted indole ring, a substituted or unsubstituted quinoline ring, a substituted or unsubstituted isoquinoline ring, a substituted or unsubstituted quinoxaline ring, a substituted or unsubstituted quinazoline ring, a substituted or unsubstituted carbazole ring, a substituted or unsubstituted phenazine ring, or a substituted or unsubstituted phenanthroline ring, and $Ar^2$ is a substituted or unsubstituted C6 to C30 hydrocarbon cyclic group including at least one functional group of C=O, C=S, C=Se, C=Te, or $C=CR^aR^b$, wherein $R^a$ and $R^b$ are each independently hydrogen, a substituted or unsubstituted C1 to C10 alkyl group, a cyano group or a cyano-containing group; a substituted or unsubstituted C2 to C30 heterocyclic group including at least one functional group of C=O, C=S, C=Se, C=Te, or $C=CR^aR^b$, wherein $R^a$ and $R^b$ are each independently hydrogen, a substituted or unsubstituted C1 to C10 alkyl group, a cyano group, or a cyano-containing group; or a fused ring thereof.

5. The compound of claim 1, wherein in Chemical Formula 1, $Ar^1$ is a C6 to C30 arene group substituted with an amine group, a C3 to C30 heteroarene group substituted with an amine group, or a condensed ring thereof.

6. The compound of claim 1, wherein in Chemical Formula 1, $Ar^1$ is a C6 to C30 arene group unsubstituted with an electron withdrawing group represented by $Ar^2$, a C3 to C30 heteroarene group unsubstituted with the electron withdrawing group represented by $Ar^2$, or condensed rings thereof.

7. The compound of claim 1, wherein

Chemical Formula 1 includes one or more spiro structures, the one or more spiro structures including at least one of the first spiro structure, the second spiro structure, or the third spiro structure, and in Chemical Formula 1, each spiro structure of the one or more spiro structures is a substituted or unsubstituted C5 to C30 hydrocarbon cyclic group or a substituted or unsubstituted C2 to C30 heterocyclic group.

8. The compound of claim 1, wherein

Chemical Formula 1 includes one or more spiro structures, the one or more spiro structures including at least one of the first spiro structure, the second spiro structure, or the third spiro structure, and in Chemical Formula 1, each spiro structure of the one or more spiro structures comprises a moiety represented by Chemical Formula 3:

[Chemical Formula 3]

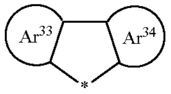

wherein, in Chemical Formula 3, $Ar^{33}$ and $Ar^{34}$ are each independently a substituted or unsubstituted C6 to C30 arene group, a substituted or unsubstituted C3 to C30 heteroarene group, or a condensed ring thereof, and

* indicates a linking point that is linked to Chemical Formula 1.

9. The compound of claim 1, wherein

Chemical Formula 1 includes one or more spiro structures, the one or more spiro structures including at least one of the first spiro structure, the second spiro structure, or the third spiro structure, and each spiro structure of the one or more spiro structures in Chemical Formula 1 comprises one of moieties represented by Chemical Formula 4:

[Chemical Formula 4]

(1)

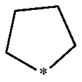

(2)

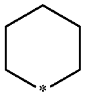

(3)

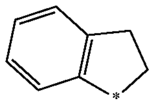

(4)

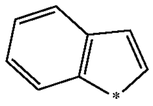

(5)

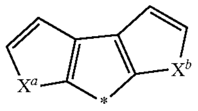

(6)

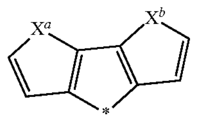

(7)

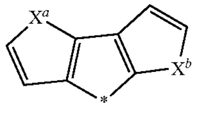

-continued (8)

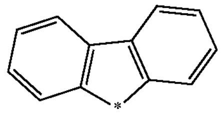

(9)

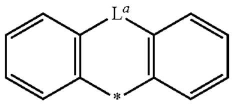

(10)

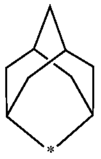

wherein, in Chemical Formula 4, $X^a$ and $X^b$ are each independently —O—, —S—, —Se—, —Te—, —S(═O)—, —$S(═O)_2$—, —$NR^{a1}$—, —$BR^{a2}$—, —$SiR^bR^e$—, —$SiR^{bb}R^{cc}$—, —$GeR^dR^e$—, or —$GeR^{dd}R^{ee}$—, wherein $R^{a1}$, $R^{a2}$, $R^b$, $R^c$, $R^d$, and $R^e$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and each pair of $R^{bb}$ and $R^{cc}$ or $R^{dd}$ and $R^{ee}$ is linked to each other to provide a ring structure, $L^a$ is —O—, —S—, —Se—, —Te—, —$NR^{a1}$—, —$BR^{a2}$—, —$SiR^bR^e$—, —$GeR^dR^e$—, —$(CR^fR^g)_{n1}$—, —(C($R^p$)═N))—, or a single bond, wherein $R^{a1}$, $R^{a2}$, $R^b$, $R^c$, $R^d$, $R^e$, $R^f$, $R^g$, and $R^p$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and n1 of —$(CR^fR^g)_{n1}$— is 1 or 2, at least one hydrogen of each ring is not replaced or is replaced by at least one substituent of deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and

* indicates a linking point that is linked to Chemical Formula 1.

10. The compound of claim 9, wherein in Chemical Formula 4, at least one CH present in an aromatic ring of at least one of moieties (3), (4), (5), (6), (7), (8), or (9) is replaced by N.

11. The compound of claim 1, wherein in Chemical Formula 1, $Ar^2$ is a cyclic group represented by Chemical Formula 5:

[Chemical Formula 5]

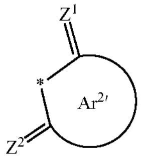

wherein, in Chemical Formula 5, $Ar^{2'}$ is a substituted or unsubstituted C6 to C30 aryl group or a substituted or unsubstituted C3 to C30 heteroaryl group, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, and

* indicates a linking point that is linked to Chemical Formula 1.

12. The compound of claim 1, wherein in Chemical Formula 1, $Ar^2$ is a cyclic group represented by any one of Chemical Formulas 6A to 6G:

[Chemical Formula 6A]

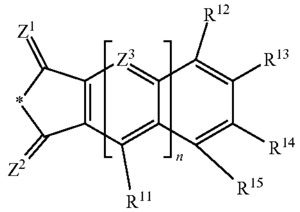

wherein, in Chemical Formula 6A, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $Z^3$ is N or $CR^c$, wherein $R^c$ is hydrogen, deuterium, or a substituted or unsubstituted C1 to C10 alkyl group, $R^{11}$, $R^{12}$, $R^{13}$, $R^{14}$, and $R^{15}$ are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, wherein $R^{11}$, $R^{12}$, $R^{13}$, $R^{14}$, and $R^{15}$ are each independently present or a pair of $R^{12}$ and $R^{13}$ or a pair of $R^{14}$ and $R^{15}$ is linked to each other to provide an aromatic ring, n is 0 or 1, and

* indicates a linking point that is linked to Chemical Formula 1,

[Chemical Formula 6B]

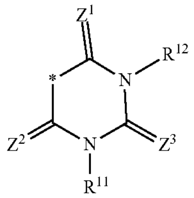

wherein, in Chemical Formula 6B, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $Z^3$ is O, S, Se, Te, or $C(R^a)(CN)$, wherein $R^a$ is hydrogen, a cyano group (—CN), or a C1 to C10 alkyl group, $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* indicates a linking point that is linked to Chemical Formula 1,

[Chemical Formula 6C]

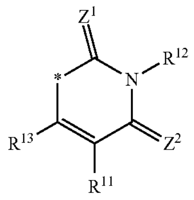

wherein, in Chemical Formula 6C, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $R^{11}$, $R^{12}$, and $R^{13}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or any combination thereof, and

* indicates a linking point that is linked to Chemical Formula 1,

[Chemical Formula 6D]

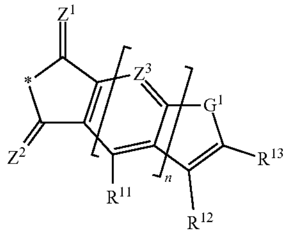

wherein, in Chemical Formula 6D, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $Z^3$ is N or $CR^c$, wherein $R^c$ is hydrogen or a substituted or unsubstituted C1 to C10 alkyl group, $G^1$ is O, S, Se, Te, $SiR^xR^y$ and $GeR^zR^w$, wherein $R^x$, $R^y$, $R^z$ and $R^w$ are each independently hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, wherein $R^{12}$ and $R^{13}$ are each independently present or are linked to each other to provide a fused aromatic ring, n is 0 or 1, and

* indicates a linking point that is linked to Chemical Formula 1,

[Chemical Formula 6E]

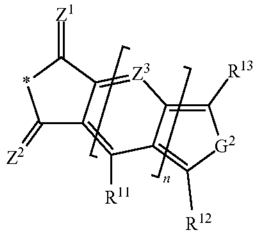

wherein, in Chemical Formula 6E, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $Z^3$ is N or $CR^c$, wherein $R^e$ is hydrogen or a substituted or unsubstituted C1 to C10 alkyl group, $G^2$ is O, S, Se, Te, $SiR^xR^y$, or $GeR^zR^w$, wherein $R^x$, $R^y$, $R^z$ and $R^w$ are each independently hydrogen, deuterium, a halogen, a cyano group, a substituted or unsubstituted C1 to C20 alkyl group, or a substituted or unsubstituted C6 to C20 aryl group, $R^{11}$, $R^{12}$, and $R^{13}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or any combination thereof, wherein $R^{12}$ and $R^{13}$ are each independently present or a pair of $R^{12}$ and $R^{13}$ is linked to each other to provide an aromatic ring, n is 0 or 1, and

* indicates a linking point that is linked to Chemical Formula 1,

[Chemical Formula 6F]

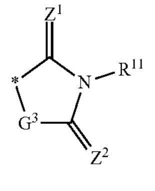

wherein, in Chemical Formula 6F, $Z^1$ and $Z^2$ are each independently O, S, Se, Te, or $CR^aR^b$, wherein $R^a$ and $R^b$ are each independently hydrogen, a substituted or unsubstituted C1 to C10 alkyl group, a cyano group, or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or any combination thereof, $G^3$ is O, S, Se, Te, $SiR^xR^y$, or $GeR^zR^w$, wherein $R^x$, $R^y$, $R^z$, and $R^w$ are each independently hydrogen, deuterium, a halogen, a cyano group, a substituted or unsubstituted C1 to C20 alkyl group, or a substituted or unsubstituted C6 to C20 aryl group, and

* indicates a linking point that is linked to Chemical Formula 1,

[Chemical Formula 6G]

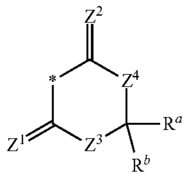

wherein, in Chemical Formula 6G, $R^a$ and $R^b$ are each independently hydrogen, a substituted or unsubstituted C1 to C10 alkyl group, a cyano group, or a cyano-containing group, $Z^1$ to $Z^4$ are each independently O, S, Se, Te, or $CR^cR^d$, wherein $R^e$ and $R^d$ are each independently hydrogen, a substituted or unsubstituted C1 to C10 alkyl group, a cyano group, or a cyano-containing group, and

* indicates a linking point that is linked to Chemical Formula 1.

13. The compound of claim 1, wherein the compound represented by Chemical Formula 1 has a sublimation temperature of equal to or greater than about 100° C. and less than or equal to about 390° C.

14. A photoelectric device, comprising:

a first electrode and a second electrode facing each other, and a light absorbing layer between the first electrode and the second electrode, wherein the light absorbing layer includes the compound represented by Chemical Formula 1 of claim 1.

15. The photoelectric device of claim 14, wherein the light absorbing layer is configured to absorb light of a red wavelength spectrum, a green wavelength spectrum, a blue wavelength spectrum, an infrared wavelength spectrum, or any combination thereof, wherein the light absorbing layer includes a p-type semiconductor and an n-type semiconductor, wherein one of the p-type semiconductor or the n-type semiconductor includes the compound represented by Chemical Formula 1.

16. The photoelectric device of claim 15, wherein the n-type semiconductor includes the compound represented by Chemical Formula 1, and the p-type semiconductor includes a compound represented by Chemical Formula 7:

[Chemical Formula 7]

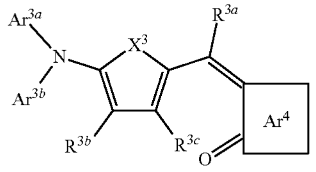

wherein, in Chemical Formula 7, $X^3$ is O, S, Se, Te, S(=O), S(=O)$_2$, Si$R^aR^b$, Ge$R^cR^d$, or C$R^eR^f$, wherein $R^a$, $R^b$, $R^c$, $R^d$, $R^e$, and $R^f$ are each independently hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ are each independently present or at least one pair of $R^a$ and $R^b$, $R^c$ and $R^d$, or $R^e$ and $R^f$ is linked to each other to provide a spiro structure, $Ar^{3a}$ and $Ar^{3b}$ are each independently a substituted or unsubstituted C6 to C30 aryl group or a substituted or unsubstituted C3 to C30 heteroaryl group, wherein $Ar^{3a}$ and $Ar^{3b}$ are each independently present or are linked to each other to provide a fused ring, $Ar^4$ is a substituted or unsubstituted C6 to C30 arene group, a substituted or unsubstituted C3 to C30 heteroarene group, or a fused ring of two or more thereof, and $R^{3a}$, $R^{3b}$, and $R^{30c}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ are each independently present or are linked to each other to provide a ring, and $Ar^{3b}$ and $R^{3b}$ are optionally linked to each other to provide a fused ring.

17. The photoelectric device of claim 16, wherein the compound represented by Chemical Formula 7 is represented by Chemical Formula 7A or Chemical Formula 7B:

[Chemical Formula 7A]

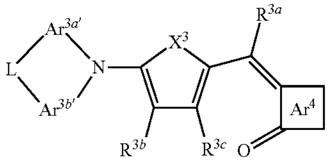

[Chemical Formula 7B]

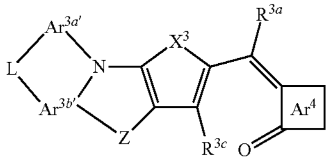

wherein, in Chemical Formula 7A and Chemical Formula 7B, $X^3$ is O, S, Se, Te, S(=O), S(=O)$_2$, Si$R^aR^b$, Ge$R^cR^d$, or C$R^eR^f$, wherein $R^a$, $R^b$, $R^c$, $R^d$, $R^e$, and $R^f$ are each independently hydrogen, deuterium, a substituted or unsubstituted C1 to C20 alkyl group, or a substituted or unsubstituted C6 to C20 aryl group, wherein $R^a$, $R^b$, $R^c$, $R^d$, $R^e$, and $R^f$ are each independently present or at least one pair of $R^a$ and $R^b$, $R^c$ and $R^d$, or $R^e$ and $R^f$ is linked to each other to provide a spiro structure, $Ar^{3a'}$ and $Ar^{3b'}$ are each independently a substituted or unsubstituted C6 to C30 arene group or a substituted or unsubstituted C3 to C30 heteroarene group, $Ar^4$ is a substituted or unsubstituted C6 to C30 arene group, a substituted or unsubstituted C3 to C30 heteroarene group, or a fused ring of two or more thereof, L and Z are each independently a single bond, O, S, Se, Te, S(=O), S(=O)$_2$, C$R^fR^g$, Si$R^hR^i$, Ge$R^jR^k$, N$R^l$, a substituted or unsubstituted C1 to C30 alkylene group, a substituted or unsubstituted C3 to C30 cycloalkylene group, a substituted or unsubstituted C6 to C30 arylene group, or any combination thereof, wherein $R^f$, $R^g$, $R^h$, $R^i$, $R^j$, $R^k$, and $R^l$ are each independently hydrogen, deuterium, a substituted or unsubstituted C1 to C20 alkyl group, or a substituted or unsubstituted C6 to C20 aryl group, and $R^{3a}$, $R^{3b}$, and $R^{3e}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein $R^{3b}$ and $R^{3c}$ are each independently present or are linked to each other to provide a ring.

18. The photoelectric device of claim 15, wherein the p-type semiconductor includes the compound represented by Chemical Formula 1, and the n-type semiconductor includes a compound represented by Chemical Formula 8:

[Chemical Formula 8]

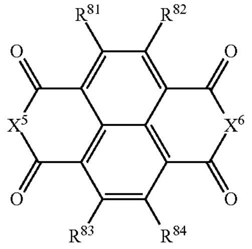

wherein, in Chemical Formula 8, $X^5$ and $X^6$ are each independently O or N$R^a$, wherein $R^a$ is hydrogen, a substituted or unsubstituted C1 to C30 alkyl group, a substituted or unsubstituted C6 to C30 aryl group, a substituted or unsubstituted C3 to C30 heterocyclic group, a halogen, or a cyano group, and $R^{81}$ to $R^{84}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

19. A light absorption sensor comprising the photoelectric device of claim 14.

20. A sensor-embedded display panel, comprising a substrate, a light emitting element on the substrate and including a light emitting layer, and a light absorption sensor disposed on the substrate and comprising a light absorbing layer, the light absorbing layer being arranged in parallel with the light emitting layer along an in-plane direction of the substrate such that the light absorbing layer and the light emitting layer at least partially overlap in the in-plane direction, wherein the light absorbing layer is configured to absorb light of a red wavelength spectrum, a green wavelength spectrum, a blue wavelength spectrum, an infrared wavelength spectrum, or any combination thereof, the light absorbing layer includes a p-type semiconductor and an n-type semiconductor, and one of the p-type semiconductor or the n-type semiconductor comprises the compound of claim 1 that is the compound represented by Chemical Formula 1.

21. The sensor-embedded display panel of claim 20, wherein the n-type semiconductor includes the compound represented by Chemical Formula 1, and the p-type semiconductor includes a compound represented by Chemical Formula 7

[Chemical Formula 7]

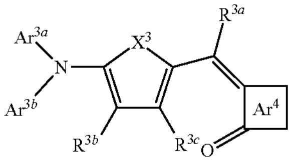

wherein, in Chemical Formula 7, $X^3$ is O, S, Se, Te, S(=O), S(=O)$_2$, SiR$^a$R$^b$, GeR$^e$R$^d$, or CR$^e$R$^f$, wherein R$^a$, R$^b$, R$^e$, R$^d$, R$^e$, and R$^f$ are each independently hydrogen, deuterium, a substituted or unsubstituted C1 to C20 alkyl group, or a substituted or unsubstituted C6 to C20 aryl group, wherein R$^a$, R$^b$, R$^e$, R$^d$, R$^e$, and R$^f$ are each independently present or at least one pair of R$^a$ and R$^b$, R$^e$ and R$^d$, or R$^e$ and R$^f$ is linked to each other to provide a spiro structure, Ar$^{3a}$ and Ar$^{3b}$ are each independently a substituted or unsubstituted C6 to C30 aryl group or a substituted or unsubstituted C3 to C30 heteroaryl group, wherein Ar$^{3a}$ and Ar$^{3b}$ are each independently present or are linked to each other to provide a fused ring, $Ar^4$ is a substituted or unsubstituted C6 to C30 arene group, a substituted or unsubstituted C3 to C30 heteroarene group, or a fused ring of two or more thereof, R$^{3a}$, R$^{3b}$, and R$^{3c}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, wherein R$^{3b}$ and R$^{3c}$ are each independently present or are linked to each other to provide a ring, and Ar$^{3b}$ and R$^{3b}$ are optionally linked to each other to provide a fused ring.

22. The sensor-embedded display panel of claim 20, wherein the p-type semiconductor includes the compound represented by Chemical Formula 1, and the n-type semiconductor includes a compound represented by Chemical Formula 8:

[Chemical Formula 8]

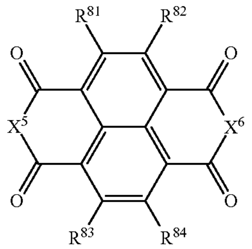

wherein, in Chemical Formula 8, $X^5$ and $X^6$ are each independently O or NR$^a$, wherein R$^a$ is hydrogen, a substituted or unsubstituted C1 to C30 alkyl group, a substituted or unsubstituted C6 to C30 aryl group, a substituted or unsubstituted C3 to C30 heterocyclic group, a halogen, or a cyano group, and $R^{81}$ to $R^{84}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

23. An electronic device comprising the photoelectric device of claim 14.

* * * * *